US008637236B2

(12) United States Patent
Minassian et al.

(10) Patent No.: US 8,637,236 B2

(45) **Date of Patent: *Jan. 28, 2014**

(54) MECP2E1 GENE

(75) Inventors: Berge A. Minassian, Toronto (CA); John B. Vincent, Toronto (CA)

(73) Assignees: The Hospital for Sick Children, Toronto (CA); Centre for Addiction and Mental Health, Toronto (CA)

( * ) Notice: Subject to any disclaimer, the term of this patent is extended or adjusted under 35 U.S.C. 154(b) by 225 days.

This patent is subject to a terminal disclaimer.

(21) Appl. No.: 12/657,559

(22) Filed: Jan. 21, 2010

(65) Prior Publication Data

US 2010/0203526 A1 Aug. 12, 2010

Related U.S. Application Data

(63) Continuation-in-part of application No. 11/352,153, filed on Feb. 9, 2006, now Pat. No. 7,670,773, which is a continuation of application No. PCT/CA2005/000198, filed on Feb. 17, 2005.

(60) Provisional application No. 60/544,311, filed on Feb. 17, 2004.

(51) Int. Cl.
*C12Q 1/68* (2006.01)

(52) U.S. Cl.
USPC .......... 435/6

(58) Field of Classification Search
None
See application file for complete search history.

(56) References Cited

U.S. PATENT DOCUMENTS

| | | | |
|---|---|---|---|
| 6,709,817 | B1 | 3/2004 | Zoghbi et al. |
| 7,670,773 | B2 | 3/2010 | Minassian et al. |
| 2002/0137067 | A1 | 9/2002 | Beaudet et al. |
| 2003/0082606 | A1 | 5/2003 | Lebo et al. |
| 2005/0227229 | A1 | 10/2005 | Lebo et al. |
| 2006/0194257 | A1 | 8/2006 | Minassian et al. |
| 2009/0098565 | A1 | 4/2009 | Minassian et al. |

FOREIGN PATENT DOCUMENTS

| | | |
|---|---|---|
| JP | 2001292775 | 10/2001 |
| WO | WO 2005/078099 A1 | 8/2005 |

OTHER PUBLICATIONS

Bloecker, H., et al., Accession No. BX538060, GENBANK Database, [online] Jun. 17, 2003, [retrieved on May 17, 2006] retrieved from the Internet http://www.ncbi.nlm.nih.gov/entrez/viewer.fcgi?db=nucleotide&val=31874178.

Bloecker, H., et al., Accession No. CAD97991, GENPEPT Database, [online] Jun. 17, 2003, [retrieved on May 17, 2006] retrieved from the Internet http://www.ncbi.nlm.nih.gov/entrez/viewer.fcgi?db=protein&val=31874179.

Kass, S.U., et al., Accession No. AF051768, GENBANK Database [online] Jan. 5, 1999 [retrieved on May 17, 2006] retrieved from the Internet http://www.ncbi.nlm.nih.gov/entrez/viewer.fcgi?db=nucleotide&val=4105998.

Kass, S.U., et al., Accession No. AAD02651, GENPEPT Database, [online] Jan. 5, 1999 [retrieved on May 17, 2006] retrieved from the Internet http:/www.ncbi.nlm.nih.gov/entrez/viewer.fcgi?db=protein&val=4105999.

Coenraads, M., "Researchers Confirm Novel Form of the Rett Syndrome Protein," Rett Syndrome Research Foundation: Press Releases: Mar. 22, 2004, pp. 1-2, [retrieved on May 17, 2006] Retrieved from the Internet http://www.rsrf.org/about_rsrf/1.5.2.html.

Chen, R. Z., et al., "Deficiency of Methyl-CpG Binding Protein-2 in CNS Neurons Results in a Rett-like Phenotype in Mice," *Nature Genetics*, 27: 327-331 (Mar. 2001).

Kriaucionis, S., et al., "The Major Form of MeCP2 has a Novel N-terminus Generated by Alternative Splicing," *Nucleic Acids Research*, 32(5): 1818-1823 (Mar. 2004).

Evans, J. C., et al., "Variation in Exon 1 Coding Region and Promotor of *MECP2* in Rett Syndrome and Controls," *European Journal of Human Genetics*, 13: 124-126 (2005, month not available).

Kim, S., et al., "Novel de novo Nonsense Mutation of MECP2 in a Patient with Rett Syndrome," Human Mutation, Mutation in Brief #307 Online (Mar. 2000).

Erlandson, A., et al., "Multiplex Ligation-Dependent Probe Amplification (MLPA) Detects Large Deletions in the MECP2 Gene of Swedish Rett Syndrome Patients," *Genetic Testing*, 7(4): 329-332 (2003, month not available).

Bienvenu, T., et al., "MECP2 Mutations Account for most Cases of Typical Forms of Rett Syndrome," *Human Molecular Genetics*, 9(9): 1377-1384 (Mar. 2000).

Nicolao, P., et al., "DHPLC Analysis of the MECP2 Gene in Italian Rett Patients," *Human Mutation*, 18: 132-140 (May 2001).

Mnatzakanian, G. N., et al., "A Previously Unidentified MECP2 Open Reading Frame Defines a New Protein Isofoint Relevant to Rett Syndrome," *Nature Genetics*, 36(4): 339-341 (Mar. 2004).

Vacca, M., et al., "Mutation Analysis of the MECP2 Gene in British and Italian Rett Syndrome Females," *J. Mol. Med.*, 78: 648-655 (2001, month not available).

Cheadle, J. P., et al., "Long-Read Sequence Analysis of the *MECP2* Gene in Rett Syndrome Patients: Correlation of Disease Severity with Mutation Type and Location," *Human Molecular Genetics*, 9(7): 1119-1129 (2000, month not available).

Bourdon, V., et al., "A Detailed Analysis of the *MECP2* Gene: Prevalence of Recurrent Mutations and Gross DNA Rearrangements in Rett Syndrome Patients," *Hum. Genet*, 108: 43-50 (2001, month not available).

(Continued)

*Primary Examiner* — Ileana Popa

(74) *Attorney, Agent, or Firm* — Foley & Lardner LLP

(57) ABSTRACT

The invention is a novel MECP2E1 splice variant and its corresponding polypeptide. The invention also includes methods of using these nucleic acid sequences and proteins in medical diagnosis and treatment of neuropsychiatric disorders or development disorders.

12 Claims, 6 Drawing Sheets
(1 of 6 Drawing Sheet(s) Filed in Color)

(56) References Cited

OTHER PUBLICATIONS

Charman, T., et al., "Dimensional Phenotypic Analysis and Functional Categorisation of Mutations Reveal Novel Genotype-Phenotype Associations in Rett Syndrome," *European Journal of Human Genetics*, 13: 1121-1130 (Aug. 2005).

Christodoulou, J., et al., "RettBASE: The IRSA *MECP2* Variation Database—A New Mutation Database in Evolution," *Human Mutation*, 21: 466-472 (2003, month not available).

Amir, R. E., et al., "Rett Syndrome is Caused by Mutations in X-Linked *MECP2*, Encoding Methyl-CpG-Binding Protein 2," *Nature Genetics*, 23: 185-188 (Oct. 1999).

Willard, H. F. and Hendrich, B.D., "Breaking the Silence in Rett Syndrome," *Nature Genetics*, 23: 127-128 (Oct. 1999).

Buyse, I. M. and Hendrich, B.D., "Diagnostic Testing for Rett Syndrome by DHPLC and Direct Sequencing Analysis of the *MECP2* Gene: Identification of Several Novel Mutations and Polymorphisms," *Am. J. Hum. Genet.*, 67: 1428-1436 (Oct. 2000).

Thistlethwaite, W. A., et al., "Rapid Genotyping of Common *MeCP2* Mutations with an Electronic DNA Microchip Using Serial Differential Hybridization," *Journal of Molecular Diagnostics*, 5(2): 121-126 (May 2003).

Hammer, S., et al., "The Phenotypic Consequences of *MECP2* Mutations Extend Beyond Rett Syndrome," *Mental Retardation and Developmental Disabilities Research Reviews*, 8: 94-98 (2002, month not available).

Meloni, I., et al., "A Mutation in the Rett Syndrome Gene, *MECP2*, Causes X-Linked Mental Retardation and Progressive Spasticity in Males," *Am. J. Hum. Genet.*, 67: 982-985 (Sep. 2000).

Samaco, R. C., et al., "Multiple Pathways Regulate MeCP2 Expression in Normal Brain Development and Exhibit Defects in Autism-Spectrum Disorders," *Human Molecular Genetics*, 13(6): 629-639 (Jan. 2004).

Beyer, K. S., et al., "Mutation Analysis of the Coding Sequence of the *MECP2* Gene in Infantile Autism," *Hum. Genet.*, 111: 305-309 (Aug. 2002).

Shi, J., et al., Detection of Heterozygous Deletions and Duplications in the MECP2 Gene in Rett Syndrome by Robust Dosage PCR (RD-PCR), Human Mutation, Mutation in Brief #809 Online, 7 pages (Feb. 2005).

Fyfe, S., et al., "InterRett and RettBASE: International Rett Syndrome Association Databases for Rett Syndrome," *Journal of Child Neurology*, 18: 709-713 (Oct. 2003).

Archer, H. L., et al., "Gross Rearrangements of the MECP2 Gene Are Found in Both Classical and Atypical Rett Syndrome Patients," *J. Med. Genet.*, 43: 451-456 (2006, month not available).

Van Esch, H., et al., "Duplication of the *MECP2* Region is a Frequent Cause of Severe Mental Retardation and Progressive Neurological Systems in Males," *Am. J. Hum. Genet.*, 77: 442-453 (Jul. 2005).

Boulanger, S., et al., "Evaluation of the Multiplex Ligation-Dependent Probe Amplification (MLPA) Technology in the Diagnosis of Rett Syndrome," *Am. J. Hum. Genet.*, 73 (5): 572 (Nov. 2003).

Aber, K. M., et al., "Methly-CpG-Binding Protein 2 is Localized in the Postsynaptic Compartment: An Immunchemical Study Of Subcellular Fractions," *Neuroscience*, 116: 77-80 (2003, month not available).

Bienvenu, T., et al., "ARX, A Novel Prd-class-homeobox Gene Highly Expressed in the Telencephalon, Is Mutated in X-linked Mental Retardation," *Hum. Mol. Gen.*, 11(8): 981-991 (2002, month not available).

Brown, L.Y. and Brown, S. A., "Alanine Tracts: The Expanding Story of Human Illness and Trinucleotide Repeats," *Trends Genet.*, 20(1): 51-58 (Jan. 2004).

Cohen, D., et al., "MECP2 Mutation in a Boy With Language Disorder and Schizophrenia," *Am. J. Psychiatry, Letters to the Editor*, 159(1): 148-149 (Jan. 2002).

Collins, A. L., et al., "Mild Overexpression of MeCP2 Causes a Progressive Neurological Disorder in Mice," *Hum. Mol. Gen.*, 13(21): 2679-2689 (Sep. 2004).

Coy, J. F., et al., "A Complex Pattern of Evolutionary Conservation and Alternative Polyadenylation within the Long 3'-Untranslated Region of the Methyl-CpG-Binding Protein 2 Gene (*MeCP2*) Suggests a Regulatory Role in Gene Expression," *Hum. Mol. Genetics*, 8(7): 1253-1262 (1999, month not available).

D'Esposito, M., et al., "Isolation, Physical Mapping and Northern Analysis of the X-Linked Human Gene Encoding Methyl CpG-Binding Protein, MECP2," *Mamm. Genome.*, 7, 533-535 (1996, month not available).

Grønskov, K., et al., "Screening of the ARX Gene in 682 Retarded Males," *Eur. J. Hum. Genet.*, 12: 701-705 (Jun. 2004).

Hagberg, B., "Clinical Manifestations and Stages of Rett Syndrome," *Mental Retardation and Developmental Disabilities Research Reviews*, 8:61-65 (2002, month not available).

Hardingham, G. E., et al., "A Calcium Microdomain Near NMDA Receptors: On Switch for ERK-dependent Synapse-to-Nucleus Communication," *Nature Neuroscience*, 4(6): 565-566 (Jun. 2001).

Inoue, K. and Keegstra, K., "A Polyglycine Stretch is Necessary for Proper Targeting of the Protein Translocation Channel Precursor to the Outer Envelope Membrane of Chloroplasts," *The Plant Journal*, 34: 661-669 (2003, month not available).

Miltenberger-Miltenyi, G. and Laccone, F., "Mutations and Polymorphisms in the Human Methyl CpG-Binding Protein MECP2," *Human Mutation*, 22:107-115 (2003, month not available).

Orrico, A., et al., "MECP2 Mutation in Male Patients with Non-specific X-linked Mental Retardation," *FEBS Letters*, 481: 285-288 (2000, month not available).

Reichwald, K., et al., "Comparative Sequence Analysis of the *MECP2*-Locus in Human and Mouse Reveals New Transcribed Regions," *Mamm. Genome.*, 11: 182-190 (2000, month not available).

Schouten, J. P., et al., "Relative Quantification of 40 Nucleic Acid Sequences by Multiplex Ligation-Dependent Probe Amplification," *Nucleic Acids Research*, 30(12): e57, 13 pages (2002, month not available).

Shahbazian, M. D., et al., "Insight into Rett Syndrome: MeCP2 Levels Display Tissue-and-Cell-Specific Differences and Correlate with Neuronal Maturation," *Hum. Mol. Gene.*, 11(2): 115-124 (2002, month not available).

Stancheva, I., et al., "A Mutant form of MeCP2 Protein Associated with Human Rett Syndrome Cannot Be Displaced from Methylated DNA by Notch in *Xenopus* Embryos," *Mol. Cell.*, 12: 425-435 (Aug. 2003).

Utsch, B., et al., "A Novel Stable Polyalanine [Poly(A)] Expansion in the *HOXA13* Gene Associated with Hand-Foot-Genital Syndrome: Proper Function of Poly(A)-Harbouring Transcription Factors Depends on a Critical repeat Length?," *Hum. Genet.* 110:488-494 (Apr. 2002).

Muhle, R., et al., "The Genetics of Autism," *Pediatrics*, 113:472-486 (May 2004).

Kato, M., "A New Paradigm for West Syndrome Based on Molecular and Cell Biology," *Epilepsy Research*, 70:S87-S95 (2006, month not available).

Abdolmaleky, H.M. et al., "Genetics and Epigenetics in Major Psychiatric Disorders: Dilemmas, Achievements, Applications, and Future Scope," *Am. J. Pharmacogenomics*, 5:149-160 (2005, month not available).

Hardy, J., and Gwinn-Hardy, K., "Genetic Classification of Primary Neurodegenerative Disease," *Science*, 282:1075-1079 (Nov. 1998).

Amir, R.E., et al., "Mutations in Exon 1 of *MECP2* Are a Rare Cause of Rett Syndrome" *J. Med. Genet.* 42: e15, 4 pages (2005, month not available).

Kleefstra, T., et al., "*MECP2* Analysis in Mentally Retarded Patients: Implications for Routine DNA Diagnostics" *Eur. J. Hum. Genet.* 12:24-28 (2004, month not available).

Mnatzakanian, G.N., et al., "A Previously Unidentified *MECP2* Open Reading Frame Defines a New Protein Isoform Relevant to Rett Syndrome," *Nat. Genet.* 36: 339-341 (Apr. 2004).

Peippo, M.M., et al., "Pitt-Hopkins Syndrome in Two Patients and Further Definition of the Phenotype," *Clinical Dysmorphology*, 15: 47-54 (2006, month not available).

(56) References Cited

OTHER PUBLICATIONS

Poirier, K., et al., "Mutations in Exon 1 of *MECP2B* are Not a Common Cause of X-Linked Mental Retardation in Males," *European J. Hum. Genet.* 13:523-524 (Mar. 2005).
Ylisaukko-ojo, T., et al., "MECP2 Mutation Analysis in Patients with Mental Retardation," *Am. J. Med. Genet.* 132A: 121-124 (2005, month not available).
Notification of Transmittal of the International Search Report and the Written Opinion of the International Searching Authority, or the Declaration for International Application No. PCT/CA2005/000198, Mail Date: Jul. 4, 2005.
International Preliminary Report on Patentability for International Application No. PCT/CA2005/000198, Mail Date: Aug. 31, 2006.
Office Action for U.S. Appl. No. 11/352,153, Mail Date: Nov. 29, 2006.
Office Action for U.S. Appl. No. 11/352,153, Mail Date: May 3, 2007.
Office Action for U.S. Appl. No. 11/352,153, Mail Date: Nov. 30, 2007.
Office Action for U.S. Appl. No. 11/352,153, Mail Date: May 2, 2008.
Advisory Action for U.S. Appl. No. 11/352,153, Mail Date: Oct. 2, 2008.
Office Action for U.S. Appl. No. 11/352,153, Mail Date: Dec. 30, 2008.
Office Action for U.S. Appl. No. 11/352,153, Mail Date: Jul. 31, 2009.
Notice of Allowance for U.S. Appl. No. 11/352,153, Mail Date: Oct. 20, 2009.
Office Action for U.S. Appl. No. 12/313,251, Mail Date: Mar. 18, 2010.
Office Action for Japanese Application No. 2006-553398, Mail Date: Aug. 4, 2010.
Office Action for U.S. Appl. No. 12/313,251, Mail Date: Sep. 1, 2010.
Liu, J. and G. Baynam, "Cornelia deLange Syndrome," *Adv. Exp. Med. Biol.* 685: 111-123, Abstract (2010) (month not available).
de Brouwer, A.P., et al., "PRPS1 Mutations: Four Distinct Syndromes and Potential Treatment," *Am. J. Hum. Genet.*, 86: 506-518, Abstract (Apr. 2010).
Final Office Action, U.S. Appl. No. 12/313,251, Mail Date: Oct. 21, 2011.
Schollen, E. et al., "Gross Rearrangements in the *MECP2* Gene in Three Patients With Rett Syndrome: Implications for Routine Diagnosis of Rett Syndrome," *Human Mutation*, 22: 116-120 (2003).
Office Action for U.S. Appl. No. 12/313,251; Date Mailed: Feb. 22, 2011.
Office Action, U.S. Appl. No. 12/313,251, Mail Date: Feb. 1, 2012.
Office Action, U.S. Appl. No. 12/313,251; Mail Date: Jul. 24, 2012.

FIG. 1

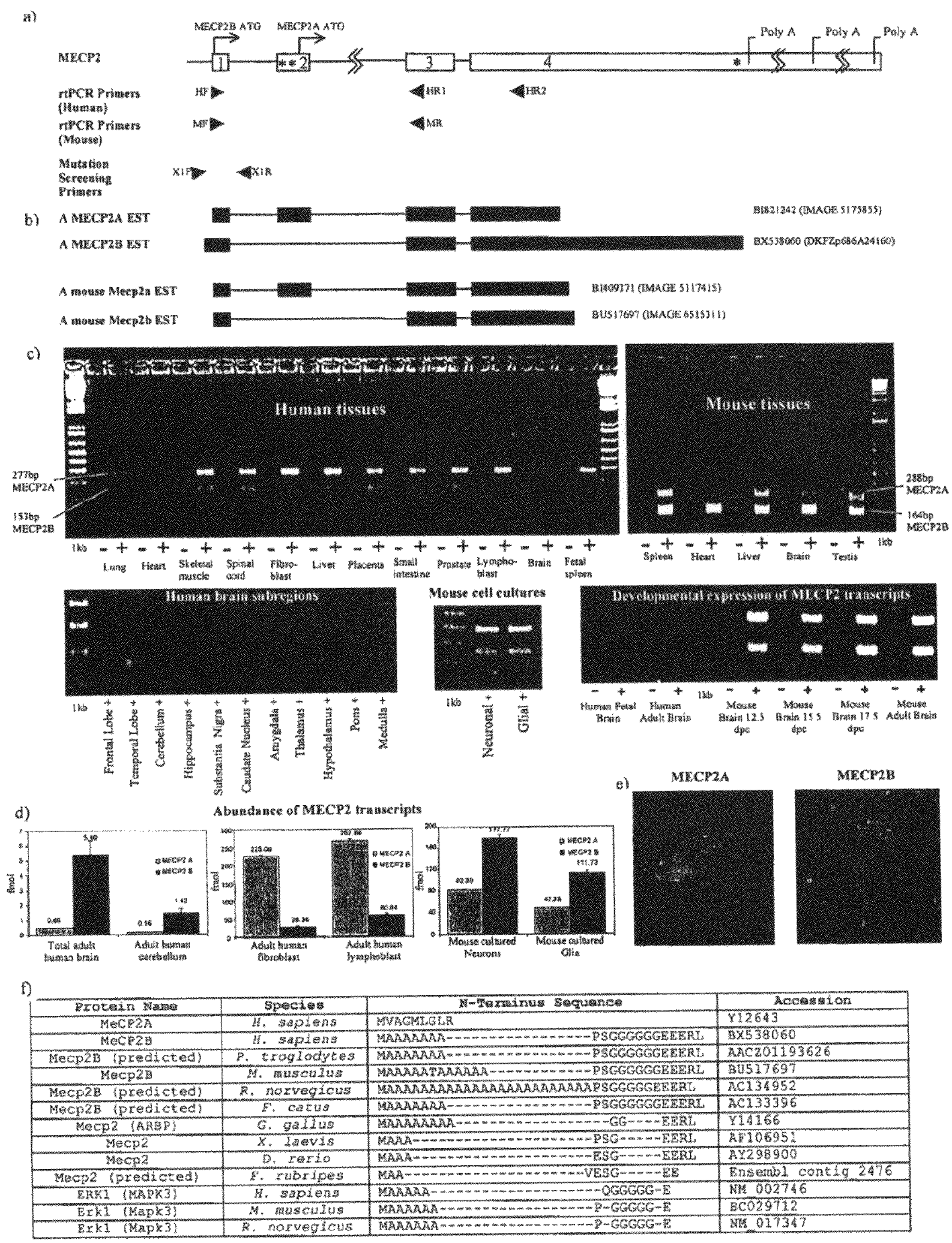

| Protein Name | Species | N-Terminus Sequence | Accession |
|---|---|---|---|
| MeCP2A | *H. sapiens* | MVAGMLGLR | Y12643 |
| MeCP2B | *H. sapiens* | MAAAAAAA-----------------PSGGGGGGEEERL | BX538060 |
| Mecp2B (predicted) | *P. troglodytes* | MAAAAAAA-----------------PSGGGGGGEEERL | AACZ01193626 |
| Mecp2B | *M. musculus* | MAAAAATAAAAAA------------PSGGGGGGEEERL | BU517697 |
| Mecp2B (predicted) | *R. norvegicus* | MAAAAAAAAAAAAAAAAAAAAAAAAPSGGGGGGEEERL | AC134952 |
| Mecp2B (predicted) | *F. catus* | MAAAAAAA-----------------PSGGGGGGEEERL | AC133396 |
| Mecp2 (ARBP) | *G. gallus* | MAAAAAAAA-------------------GG----EERL | Y14166 |
| Mecp2 | *X. laevis* | MAAA---------------------PSG-----EERL | AF106951 |
| Mecp2 | *D. rerio* | MAAA---------------------ESG-----EERL | AY298900 |
| Mecp2 (predicted) | *F. rubripes* | MAA---------------------VESG-----EE | Ensembl contig 2476 |
| ERK1 (MAPK3) | *H. sapiens* | MAAAAA-------------------QGGGGG-E | NM 002746 |
| Erk1 (Mapk3) | *M. musculus* | MAAAAAA------------------P-GGGGG-E | BC029712 |
| Erk1 (Mapk3) | *R. norvegicus* | MAAAAAA------------------P-GGGGG-E | NM_017347 |

SEQUENCE LISTING

<160> NUMBER OF SEQ ID NOS: 29

<210> SEQ ID NO 1
<211> LENGTH: 10182
<212> TYPE: DNA
<213> ORGANISM: Homo sapiens

<400> SEQUENCE: 1

```
ccggaaaatg gccgccgccg ccgccgccgc gccgagcgga ggaggaggag gaggcgagga     60
ggagagactg ctccataaaa atacagactc accagttcct gctttgatgt gacatgtgac    120
tccccagaat acaccttgct tctgtagacc agctccaaca ggattccatg gtagctggga    180
tgttagggct cagggaagaa aagtcagaag accaggacct ccagggcctc aaggacaaac    240
ccctcaagtt taaaaaggtg aagaaagata agaaagaaga gaaagagggc aagcatgagc    300
ccgtgcagcc atcagcccac cactctgctg agcccgcaga ggcaggcaaa gcagagacat    360
cagaagggtc aggctccgcc ccggctgtgc cggaagcttc tgcctccccc aaacagcggc    420
gctccatcat ccgtgaccgg ggacccatgt atgatgaccc caccctgcct gaaggctgga    480
cacggaagct taagcaaagg aaatctggcc gctctgctgg gaagtatgat gtgtatttga    540
tcaatcccca gggaaaagcc tttcgctcta aagtggagtt gattgcgtac ttcgaaaagg    600
taggcgacac atccctggac cctaatgatt ttgacttcac ggtaactggg agagggagcc    660
cctcccggcg agagcagaaa ccacctaaga agcccaaatc tcccaaagct ccaggaactg    720
gcagaggccg gggacgcccc aaagggagcg gcaccacgag acccaaggcg gccacgtcag    780
agggtgtgca ggtgaaaagg gtcctggaga aaagtcctgg gaagctcctt gtcaagatgc    840
cttttcaaac ttcgccaggg ggcaaggctg agggggggtgg ggccaccaca tccacccagg    900
tcatggtgat caaacgcccc ggcaggaagc gaaaagctga ggccgaccct caggccattc    960
ccaagaaacg gggccgaaag ccggggagtg tggtggcagc cgctgccgcc gaggccaaaa   1020
agaaagccgt gaaggagtct tctatccgat ctgtgcagga gaccgtactc cccatcaaga   1080
agcgcaagac ccgggagacg gtcagcatcg aggtcaagga agtggtgaag cccctgctgg   1140
tgtccaccct cggtgagaag agcgggaaag gactgaagac ctgtaagagc cctgggcgga   1200
aaagcaagga gagcagcccc aaggggcgca gcagcagcgc ctcctcaccc cccaagaagg   1260
agcaccacca ccatcaccac cactcagagt ccccaaaggc ccccgtgcca ctgctcccac   1320
ccctgccccc acctccacct gagcccgaga gctccgagga ccccaccagc ccccctgagc   1380
cccaggactt gagcagcagc gtctgcaaag aggagaagat gcccagagga ggctcactgg   1440
agagcgacgg ctgccccaag gagccagcta agactcagcc cgcggttgcc accgccgcca   1500
cggccgcaga aaagtacaaa caccgagggg agggagagcg caaagacatt gtttcatcct   1560
ccatgccaag gccaaacaga gaggagcctg tggacagccg gacgcccgtg accgagagag   1620
ttagctgact ttacacggag cggattgcaa agcaaaccaa caagaataaa ggcagctgtt   1680
gtctcttctc cttatgggta gggctctgac aaagcttccc gattaactga aataaaaaat   1740
atttttttt ctttcagtaa acttagagtt tcgtggcttc agggtgggag tagttggagc   1800
attggggatg tttttcttac cgacaagcac agtcaggttg aagacctaac cagggccaga   1860
agtagctttg cacttttcta aactaggctc cttcaacaag gcttgctgca gatactactg   1920
accagacaag ctgttgacca ggcacctccc ctcccgccca aacctttccc ccatgtggtc   1980
gttagagaca gagcgacaga gcagttgaga ggacactccc gttttcggtg ccatcagtgc   2040
```

```
cccgtctaca gctcccccag ctccccccac ctcccccact cccaaccacg ttgggacagg   2100
gaggtgtgag gcaggagaga cagttggatt ctttagagaa gatggatatg accagtggct   2160
atggcctgtg cgatcccacc cgtggtggct caagtctggc cccacaccag ccccaatcca   2220
aaactggcaa ggacgcttca caggacagga aagtggcacc tgtctgctcc agctctggca   2280
tggctaggag gggggagtcc cttgaactac tgggtgtaga ctggcctgaa ccacaggaga   2340
ggatggccca gggtgaggtg gcatggtcca ttctcaaggg acgtcctcca acgggtggcg   2400
ctagaggcca tggaggcagt aggacaaggt gcaggcaggc tggcctgggg tcaggccggg   2460
cagagcacag cggggtgaga gggattccta atcactcaga gcagtctgtg acttagtgga   2520
caggggaggg ggcaaagggg gaggagaaga aaatgttctt ccagttactt tccaattctc   2580
ctttagggac agcttagaat tatttgcact attgagtctt catgttccca cttcaaaaca   2640
aacagatgct ctgagagcaa actggcttga attggtgaca tttagtccct caagccacca   2700
gatgtgacag tgttgagaac tacctggatt tgtatatata cctgcgcttg ttttaaagtg   2760
ggctcagcac atagggttcc cacgaagctc cgaaactcta agtgtttgct gcaattttat   2820
aaggacttcc tgattggttt ctcttctccc cttccatttc tgccttttgt tcatttcatc   2880
ctttcacttc tttcccttcc tccgtcctcc tccttcctag ttcatccctt ctcttccagg   2940
cagccgcggt gcccaaccac acttgtcggc tccagtcccc agaactctgc ctgccctttg   3000
tcctcctgct gccagtacca gccccaccct gttttgagcc ctgaggaggc cttgggctct   3060
gctgagtccg acctggcctg tctgtgaaga gcaagagagc agcaaggtct tgctctccta   3120
ggtagccccc tcttccctgg taagaaaaag caaaaggcat ttcccaccct gaacaacgag   3180
ccttttcacc cttctactct agagaagtgg actggaggag ctgggcccga tttggtagtt   3240
gaggaaagca cagaggcctc ctgtggcctg ccagtcatcg agtggcccaa caggggctcc   3300
atgccagccg accttgacct cactcagaag tccagagtct agcgtagtgc agcagggcag   3360
tagcggtacc aatgcagaac tcccaagacc cgagctggga ccagtacctg ggtccccagc   3420
ccttcctctg ctccccctt tccctcggag ttcttcttga atggcaatgt tttgcttttg   3480
ctcgatgcag acagggggcc agaacaccac acatttcact gtctgtctgg tccatagctg   3540
tggtgtaggg gcttagaggc atgggcttgc tgtgggtttt taattgatca gttttcatgt   3600
gggatcccat ctttttaacc tctgttcagg aagtccttat ctagctgcat atcttcatca   3660
tattggtata tccttttctg tgtttacaga gatgtctctt atatctaaat ctgtccaact   3720
gagaagtacc ttatcaaagt agcaaatgag acagcagtct tatgcttcca gaaacaccca   3780
caggcatgtc ccatgtgagc tgctgccatg aactgtcaag tgtgtgttgt cttgtgtatt   3840
tcagttattg tccctggctt ccttactatg gtgtaatcat gaaggagtga aacatcatag   3900
aaactgtcta gcacttcctt gccagtcttt agtgatcagg aaccatagtt gacagttcca   3960
atcagtagct taagaaaaaa ccgtgtttgt ctcttctgga atggttagaa gtgagggagt   4020
ttgccccgtt ctgtttgtag agtctcatag ttggactttc tagcatatat gtgtccattt   4080
ccttatgctg taaaagcaag tcctgcaacc aaactcccat cagcccaatc cctgatccct   4140
gatcccttcc acctgctctg ctgatgaccc ccccagcttc acttctgact cttccccagg   4200
aagggaaggg gggtcagaag agagggtgag tcctccagaa ctcttcctcc aaggacagaa   4260
ggctcctgcc cccatagtgg cctcgaactc ctggcactac caaaggacac ttatccacga   4320
gagcgcagca tccgaccagg ttgtcactga gaagatgttt attttggtca gttgggtttt   4380
tatgtattat acttagtcaa atgtaatgtg gcttctggaa tcattgtcca gagctgcttc   4440
```

-continued

```
cccgtcacct gggcgtcatc tggtcctggt aagaggagtg cgtggcccac caggcccccc   4500

tgtcacccat gacagttcat tcagggccga tggggcagtc gtggttggga acacagcatt   4560

tcaagcgtca ctttatttca ttcgggcccc acctgcagct ccctcaaaga ggcagttgcc   4620

cagcctcttt cccttccagt ttattccaga gctgccagtg gggcctgagg ctccttaggg   4680

ttttctctct atttccccct ttcttcctca ttccctcgtc tttcccaaag gcatcacgag   4740

tcagtcgcct ttcagcaggc agccttggcg gtttatcgcc ctggcaggca ggggccctgc   4800

agctctcatg ctgcccctgc cttggggtca ggttgacagg aggttggagg gaaagcctta   4860

agctgcagga ttctcaccag ctgtgtccgg cccagttttg ggtgtgacc tcaatttcaa   4920

ttttgtctgt acttgaacat tatgaagatg gggcctcttt tcagtgaatt tgtgaacagc   4980

agaattgacc gacagctttc cagtacccat ggggctaggt cattaaggcc acatccacag   5040

tctcccccac ccttgttcca gttgttagtt actacctcct ctcctgacaa tactgtatgt   5100

cgtcgagctc cccccaggtc taccccctccc ggccctgcct gctggtgggc ttgtcatagc   5160

cagtgggatt gccggtcttg acagctcagt gagctggaga tacttggtca cagccaggcg   5220

ctagcacagc tcccttctgt tgatgctgta ttcccatatc aaaagacaca ggggacaccc   5280

agaaacgcca catcccccaa tccatcagtg ccaaactagc caacggcccc agcttctcag   5340

ctcgctggat ggcggaagct gctactcgtg agcgccagtg cgggtgcaga caatcttctg   5400

ttgggtggca tcattccagg cccgaagcat gaacagtgca cctgggacag ggagcagccc   5460

caaattgtca cctgcttctc tgcccagctt ttcattgctg tgacagtgat ggcgaaagag   5520

ggtaataacc agacacaaac tgccaagttg ggtggagaaa ggagtttctt tagctgacag   5580

aatctctgaa ttttaaatca cttagtaagc ggctcaagcc caggagggag cagagggata   5640

cgagcggagt cccctgcgcg ggaccatctg gaattggttt agcccaagtg gagcctgaca   5700

gccagaactc tgtgtccccc gtctaaccac agctcctttt ccagagcatt ccagtcaggc   5760

tctctgggct gactgggcca ggggaggtta caggtaccag ttctttaaga agatctttgg   5820

gcatatacat ttttagcctg tgtcattgcc ccaaatggat tcctgtttca agttcacacc   5880

tgcagattct aggacctgtg tcctagactt cagggagtca gctgtttcta gagttcctac   5940

catggagtgg gtctggagga cctgcccggt ggggggggcag agccctgctc cctccgggtc   6000

ttcctactct tctctctgct ctgacgggat ttgttgattc tctccatttt ggtgtctttc   6060

tcttttagat attgtatcaa tctttagaaa aggcatagtc tacttgttat aaatcgttag   6120

gatactgcct cccccagggt ctaaaattac atattagagg ggaaaagctg aacactgaag   6180

tcagttctca acaatttaga aggaaaacct agaaaacatt tggcagaaaa ttacatttcg   6240

atgtttttga atgaatacga gcaagctttt acaacagtgc tgatctaaaa atacttagca   6300

cttggcctga gatgcctggt gagcattaca ggcaagggga atctggaggt agccgacctg   6360

aggacatggc ttctgaacct gtcttttggg agtggtatgg aaggtggagc gttcaccagt   6420

gacctggaag gcccagcacc accctccttc ccactcttct catcttgaca gagcctgccc   6480

cagcgctgac gtgtcaggaa aacacccagg gaactaggaa ggcacttctg cctgaggggc   6540

agcctgcctt gcccactcct gctctgctcg cctcggatca gctgagcctt ctgagctggc   6600

ctctcactgc ctccccaagg ccccctgcct gccctgtcag gaggcagaag gaagcaggtg   6660

tgagggcagt gcaaggaggg agcacaaccc ccagctcccg ctccgggctc cgacttgtgc   6720

acaggcagag cccagaccct ggaggaaatc ctacctttga attcaagaac atttggggaa   6780

tttggaaatc tctttgcccc caaaccccca ttctgtccta cctttaatca ggtcctgctc   6840
```

```
agcagtgaga gcagatgagg tgaaaaggcc aagaggtttg gctcctgccc actgatagcc   6900
cctctccccg cagtgtttgt gtgtcaagtg gcaaagctgt tcttcctggt gaccctgatt   6960
atatccagta acacatagac tgtgcgcata ggcctgcttt gtctcctcta tcctgggctt   7020
ttgttttgct ttttagtttt gcttttagtt tttctgtccc ttttatttaa cgcaccgact   7080
agacacacaa agcagttgaa tttttatata tatatctgta tattgcacaa ttataaactc   7140
attttgcttg tggctccaca cacacaaaaa aagacctgtt aaaattatac ctgttgctta   7200
attacaatat ttctgataac catagcatag gacaagggaa aataaaaaaa gaaaaaaaag   7260
aaaaaaaaac gacaaatctg tctgctggtc acttcttctg tccaagcaga ttcgtggtct   7320
tttcctcgct tctttcaagg gctttcctgt gccaggtgaa ggaggctcca ggcagcaccc   7380
aggttttgca ctcttgtttc tcccgtgctt gtgaaagagg tcccaaggtt ctgggtgcag   7440
gagcgctccc ttgacctgct gaagtccgga acgtagtcgg cacagcctgg tcgccttcca   7500
cctctgggag ctggagtcca ctggggtggc ctgactcccc cagtcccctt cccgtgacct   7560
ggtcagggtg agcccatgtg gagtcagcct cgcaggcctc cctgccagta gggtccgagt   7620
gtgtttcatc cttcccactc tgtcgagcct gggggctgga gcggagacgg gaggcctggc   7680
ctgtctcgga acctgtgagc tgcaccaggt agaacgccag ggaccccaga atcatgtgcg   7740
tcagtccaag ggtcccctc caggagtagt gaagactcca gaaatgtccc tttcttctcc   7800
cccatcctac gagtaattgc atttgctttt gtaattctta atgagcaata tctgctagag   7860
agtttagctg taacagttct ttttgatcat ctttttttaa taattagaaa caccaaaaaa   7920
atccagaaac ttgttcttcc aaagcagaga gcattataat caccagggcc aaaagcttcc   7980
ctccctgctg tcattgcttc ttctgaggcc tgaatccaaa agaaaaacag ccataggccc   8040
tttcagtggc cgggctaccc gtgagccctt cggaggacca gggctggggc agcctctggg   8100
cccacatccg gggccagctc cggcgtgtgt tcagtgttag cagtgggtca tgatgctctt   8160
tcccacccag cctgggatag gggcagagga ggcgaggagg ccgttgccgc tgatgtttgg   8220
ccgtgaacag gtgggtgtct gcgtgcgtcc acgtgcgtgt tttctgactg acatgaaatc   8280
gacgcccgag ttagcctcac ccggtgacct ctagccctgc ccggatggag cggggcccac   8340
ccggttcagt gtttctgggg agctggacag tggagtgcaa aaggcttgca gaacttgaag   8400
cctgctcctt cccttgctac cacggcctcc tttccgtttg atttgtcact gcttcaatca   8460
ataacagccg ctccagagtc agtagtcaat gaatatatga ccaaatatca ccaggactgt   8520
tactcaatgt gtgccgagcc cttgcccatg ctgggctccc gtgtatctgg acactgtaac   8580
gtgtgctgtg tttgctcccc ttccccttcc ttctttgccc tttacttgtc tttctggggt   8640
ttttctgttt gggtttggtt tggtttttat ttctcctttt gtgttccaaa catgaggttc   8700
tctctactgg tcctcttaac tgtggtgttg aggcttatat ttgtgtaatt tttggtgggt   8760
gaaaggaatt ttgctaagta aatctcttct gtgtttgaac tgaagtctgt attgtaacta   8820
tgtttaaagt aattgttcca gagacaaata tttctagaca ctttttcttt acaaacaaaa   8880
gcattcggag ggagggggat ggtgactgag atgagagggg agagctgaac agatgacccc   8940
tgcccagatc agccagaagc cacccaaagc agtggagccc aggagtccca ctccaagcca   9000
gcaagccgaa tagctgatgt gttgccactt tccaagtcac tgcaaaacca ggttttgttc   9060
cgcccagtgg attcttgttt tgcttcccct ccccccgaga ttattaccac catcccgtgc   9120
ttttaaggaa aggcaagatt gatgtttcct tgaggggagc caggagggga tgtgtgtgtg   9180
cagagctgaa gagctgggga gaatggggct gggcccaccc aagcaggagg ctgggacgct   9240
```

```
ctgctgtggg cacaggtcag gctaatgttg gcagatgcag ctcttcctgg acaggccagg   9300

tggtgggcat tctctctcca aggtgtgccc cgtgggcatt actgtttaag acacttccgt   9360

cacatcccac cccatcctcc agggctcaac actgtgacat ctctattccc caccctcccc   9420

ttcccagggc aataaaatga ccatggaggg ggcttgcact ctcttggctg tcacccgatc   9480

gccagcaaaa cttagatgtg agaaaacccc ttcccattcc atggcgaaaa catctcctta   9540

gaaaagccat taccctcatt aggcatggtt ttgggctccc aaaacacctg acagcccctc   9600

cctcctctga gaggcggaga gtgctgactg tagtgaccat tgcatgccgg gtgcagcatc   9660

tggaagagct aggcagggtg tctgccccct cctgagttga agtcatgctc ccctgtgcca   9720

gcccagaggc cgagagctat ggacagcatt gccagtaaca caggccaccc tgtgcagaag   9780

ggagctggct ccagcctgga aacctgtctg aggttgggag aggtgcactt ggggcacagg   9840

gagaggccgg gacacactta gctggagatg tctctaaaag ccctgtatcg tattcacctt   9900

cagtttttgt gttttgggac aattacttta gaaaataagt aggtcgtttt aaaaacaaaa   9960

attattgatt gctttttgt agtgttcaga aaaaaggttc tttgtgtata gccaaatgac  10020

tgaaagcact gatatattta aaaacaaaag gcaatttatt aaggaaattt gtaccatttc  10080

agtaaacctg tctgaatgta cctgtatacg tttcaaaaac acccccccc cactgaatcc  10140

ctgtaaccta tttattatat aaagagtttg ccttataaat tt                    10182
```

<210> SEQ ID NO 2
<211> LENGTH: 486
<212> TYPE: PRT
<213> ORGANISM: Homo sapiens

<400> SEQUENCE: 2

```
Met Val Ala Gly Met Leu Gly Leu Arg Glu Glu Lys Ser Glu Asp Gln
 1               5                  10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
```

```
    210                 215                 220

Pro Phe Gln Thr Ser Pro Gly Gly Lys Ala Glu Gly Gly Gly Ala Thr
225                 230                 235                 240

Thr Ser Thr Gln Val Met Val Ile Lys Arg Pro Gly Arg Lys Arg Lys
                245                 250                 255

Ala Glu Ala Asp Pro Gln Ala Ile Pro Lys Lys Arg Gly Arg Lys Pro
            260                 265                 270

Gly Ser Val Val Ala Ala Ala Ala Ala Glu Ala Lys Lys Lys Ala Val
        275                 280                 285

Lys Glu Ser Ser Ile Arg Ser Val Gln Glu Thr Val Leu Pro Ile Lys
    290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ser Ala Ser Ser Pro Pro Lys Lys Glu His His His
        355                 360                 365

His His His His Ser Glu Ser Pro Lys Ala Pro Val Pro Leu Leu Pro
    370                 375                 380

Pro Leu Pro Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
            420                 425                 430

Pro Ala Lys Thr Gln Pro Ala Val Ala Thr Ala Ala Thr Ala Ala Glu
        435                 440                 445

Lys Tyr Lys His Arg Gly Glu Gly Glu Arg Lys Asp Ile Val Ser Ser
    450                 455                 460

Ser Met Pro Arg Pro Asn Arg Glu Glu Pro Val Asp Ser Arg Thr Pro
465                 470                 475                 480

Val Thr Glu Arg Val Ser
                485
```

```
<210> SEQ ID NO 3
<211> LENGTH: 1504
<212> TYPE: DNA
<213> ORGANISM: Homo sapiens

<400> SEQUENCE: 3

ccggaaaatg gccgccgccg ccgccgccgc gccgagcgga ggaggaggag gaggcgagga      60

ggagagactg gaagaaaagt cagaagacca ggacctccag ggcctcaagg acaaacccct     120

caagtttaaa aaggtgaaga aagataagaa agaagagaaa gagggcaagc atgagcccgt     180

gcagccatca gcccaccact ctgctgagcc cgcagaggca ggcaaagcag agacatcaga     240

agggtcaggc tccgccccgg ctgtgccgga agcttctgcc tcccccaaac agcggcgctc     300

catcatccgt gaccggggac ccatgtatga tgaccccacc ctgcctgaag gctggacacg     360

gaagcttaag caaaggaaat ctggccgctc tgctgggaag tatgatgtgt atttgatcaa     420

tccccaggga aaagcctttc gctctaaagt ggagttgatt gcgtacttcg aaaaggtagg     480

cgacacatcc ctggacccta atgattttga cttcacggta actgggagag ggagcccctc     540

ccggcgagag cagaaaccac ctaagaagcc caaatctccc aaagctccag gaactggcag     600
```

```
aggccgggga cgccccaaag ggagcggcac cacgagaccc aaggcggcca cgtcagaggg    660

tgtgcaggtg aaaagggtcc tggagaaaag tcctgggaag ctccttgtca agatgccttt    720

tcaaacttcg ccaggggggca aggctgaggg gggtggggcc accacatcca cccaggtcat    780

ggtgatcaaa cgccccggca ggaagcgaaa agctgaggcc gaccctcagg ccattcccaa    840

gaaacggggc cgaaagccgg ggagtgtggt ggcagccgct gccgccgagg ccaaaaagaa    900

agccgtgaag gagtcttcta tccgatctgt gcaggagacc gtactcccca tcaagaagcg    960

caagacccgg gagacggtca gcatcgaggt caaggaagtg gtgaagcccc tgctggtgtc   1020

caccctcggt gagaagagcg ggaaaggact gaagacctgt aagagccctg ggcggaaaag   1080

caaggagagc agccccaagg ggcgcagcag cagcgcctcc tcaccccccca agaaggagca   1140

ccaccaccat caccaccact cagagtcccc aaaggccccc gtgccactgc tcccacccct   1200

gcccccacct ccacctgagc ccgagagctc cgaggacccc accagccccc ctgagcccca   1260

ggacttgagc agcagcgtct gcaaagagga gaagatgccc agaggaggct cactggagag   1320

cgacggctgc cccaaggagc cagctaagac tcagcccgcg gttgccaccg ccgccacggc   1380

cgcagaaaag tacaaacacc gaggggaggg agagcgcaaa gacattgttt catcctccat   1440

gccaaggcca aacagagagg agcctgtgga cagccggacg cccgtgaccg agagagttag   1500

ctga                                                                1504
```

<210> SEQ ID NO 4
<211> LENGTH: 498
<212> TYPE: PRT
<213> ORGANISM: Homo sapiens

<400> SEQUENCE: 4

```
Met Ala Ala Ala Ala Ala Ala Ala Pro Ser Gly Gly Gly Gly Gly Gly
1               5                   10                  15

Glu Glu Glu Arg Leu Glu Glu Lys Ser Glu Asp Gln Asp Leu Gln Gly
            20                  25                  30

Leu Lys Asp Lys Pro Leu Lys Phe Lys Lys Val Lys Lys Asp Lys Lys
        35                  40                  45

Glu Glu Lys Glu Gly Lys His Glu Pro Val Gln Pro Ser Ala His His
    50                  55                  60

Ser Ala Glu Pro Ala Glu Ala Gly Lys Ala Glu Thr Ser Glu Gly Ser
65                  70                  75                  80

Gly Ser Ala Pro Ala Val Pro Glu Ala Ser Ala Ser Pro Lys Gln Arg
                85                  90                  95

Arg Ser Ile Ile Arg Asp Arg Gly Pro Met Tyr Asp Asp Pro Thr Leu
            100                 105                 110

Pro Glu Gly Trp Thr Arg Lys Leu Lys Gln Arg Lys Ser Gly Arg Ser
        115                 120                 125

Ala Gly Lys Tyr Asp Val Tyr Leu Ile Asn Pro Gln Gly Lys Ala Phe
    130                 135                 140

Arg Ser Lys Val Glu Leu Ile Ala Tyr Phe Glu Lys Val Gly Asp Thr
145                 150                 155                 160

Ser Leu Asp Pro Asn Asp Phe Asp Phe Thr Val Thr Gly Arg Gly Ser
                165                 170                 175

Pro Ser Arg Arg Glu Gln Lys Pro Pro Lys Lys Pro Lys Ser Pro Lys
            180                 185                 190

Ala Pro Gly Thr Gly Arg Gly Arg Gly Arg Pro Lys Gly Ser Gly Thr
        195                 200                 205
```

```
Thr Arg Pro Lys Ala Ala Thr Ser Glu Gly Val Gln Val Lys Arg Val
    210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Gly Ala Thr Thr Ser Thr Gln
                245                 250                 255

Val Met Val Ile Lys Arg Pro Gly Arg Lys Arg Lys Ala Glu Ala Asp
            260                 265                 270

Pro Gln Ala Ile Pro Lys Lys Arg Gly Arg Lys Pro Gly Ser Val Val
        275                 280                 285

Ala Ala Ala Ala Ala Glu Ala Lys Lys Lys Ala Val Lys Glu Ser Ser
    290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                325                 330                 335

Val Ser Thr Leu Gly Glu Lys Ser Gly Lys Gly Leu Lys Thr Cys Lys
            340                 345                 350

Ser Pro Gly Arg Lys Ser Lys Glu Ser Ser Pro Lys Gly Arg Ser Ser
        355                 360                 365

Ser Ala Ser Ser Pro Pro Lys Lys Glu His His His His His His His
    370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                405                 410                 415

Pro Gln Asp Leu Ser Ser Ser Val Cys Lys Glu Glu Lys Met Pro Arg
            420                 425                 430

Gly Gly Ser Leu Glu Ser Asp Gly Cys Pro Lys Glu Pro Ala Lys Thr
        435                 440                 445

Gln Pro Ala Val Ala Thr Ala Ala Thr Ala Ala Glu Lys Tyr Lys His
    450                 455                 460

Arg Gly Glu Gly Glu Arg Lys Asp Ile Val Ser Ser Ser Met Pro Arg
465                 470                 475                 480

Pro Asn Arg Glu Glu Pro Val Asp Ser Arg Thr Pro Val Thr Glu Arg
                485                 490                 495

Val Ser


<210> SEQ ID NO 5
<211> LENGTH: 18
<212> TYPE: DNA
<213> ORGANISM: Artificial Sequence
<220> FEATURE:
<223> OTHER INFORMATION: HF primer

<400> SEQUENCE: 5

ctcggagaga gggctgtg                                                  18


<210> SEQ ID NO 6
<211> LENGTH: 20
<212> TYPE: DNA
<213> ORGANISM: Artificial Sequence
<220> FEATURE:
<223> OTHER INFORMATION: HR1 primer

<400> SEQUENCE: 6

cttgaggggt ttgtccttga                                                20
```

<210> SEQ ID NO 7
<211> LENGTH: 20
<212> TYPE: DNA
<213> ORGANISM: Artificial Sequence
<220> FEATURE:
<223> OTHER INFORMATION: HR2 primer

<400> SEQUENCE: 7
cgtttgatca ccatgacctg 20

<210> SEQ ID NO 8
<211> LENGTH: 20
<212> TYPE: DNA
<213> ORGANISM: Artificial Sequence
<220> FEATURE:
<223> OTHER INFORMATION: MF primer

<400> SEQUENCE: 8
aggaggcgag gaggagagac 20

<210> SEQ ID NO 9
<211> LENGTH: 19
<212> TYPE: DNA
<213> ORGANISM: Artificial Sequence
<220> FEATURE:
<223> OTHER INFORMATION: MR primer

<400> SEQUENCE: 9
ctggctctgc agaatggtg 19

<210> SEQ ID NO 10
<211> LENGTH: 22
<212> TYPE: DNA
<213> ORGANISM: Artificial Sequence
<220> FEATURE:
<223> OTHER INFORMATION: MECP2B-specific primer

<400> SEQUENCE: 10
aggagagact ggaagaaaag tc 22

<210> SEQ ID NO 11
<211> LENGTH: 20
<212> TYPE: DNA
<213> ORGANISM: Artificial Sequence
<220> FEATURE:
<223> OTHER INFORMATION: reverse primer

<400> SEQUENCE: 11
cttgaggggt ttgtccttga 20

<210> SEQ ID NO 12
<211> LENGTH: 23
<212> TYPE: DNA
<213> ORGANISM: Artificial Sequence
<220> FEATURE:
<223> OTHER INFORMATION: MECP2A transcript-specific primer

<400> SEQUENCE: 12
ctcaccagtt cctgctttga tgt 23

<210> SEQ ID NO 13
<211> LENGTH: 22
<212> TYPE: DNA
<213> ORGANISM: Artificial Sequence
<220> FEATURE:
<223> OTHER INFORMATION: MECP2B transcript-specific primer

<400> SEQUENCE: 13
aggagagact ggaggaaaag tc 22

<210> SEQ ID NO 14
<211> LENGTH: 25
<212> TYPE: DNA
<213> ORGANISM: Artificial Sequence
<220> FEATURE:
<223> OTHER INFORMATION: reverse primer

<400> SEQUENCE: 14
cttaaacttc agtggcttgt ctctg 25

<210> SEQ ID NO 15
<211> LENGTH: 23
<212> TYPE: DNA
<213> ORGANISM: Artificial Sequence
<220> FEATURE:
<223> OTHER INFORMATION: MECP2A forward primer

<400> SEQUENCE: 15
tatggatcca tggtagctgg gat 23

<210> SEQ ID NO 16
<211> LENGTH: 21
<212> TYPE: DNA
<213> ORGANISM: Artificial Sequence
<220> FEATURE:
<223> OTHER INFORMATION: MECP2B forward primer

<400> SEQUENCE: 16
tatggatccg gaaaatggcc g 21

<210> SEQ ID NO 17
<211> LENGTH: 20
<212> TYPE: DNA
<213> ORGANISM: Artificial Sequence
<220> FEATURE:
<223> OTHER INFORMATION: reverse primer

<400> SEQUENCE: 17
gcgtctagag ctaactctct 20

<210> SEQ ID NO 18
<211> LENGTH: 21
<212> TYPE: PRT
<213> ORGANISM: Artificial Sequence
<220> FEATURE:
<223> OTHER INFORMATION: MeCP2 N-terminus

<400> SEQUENCE: 18

```
Met Ala Ala Ala Ala Ala Ala Ala Pro Ser Gly Gly Gly Gly Gly Gly
 1              5                  10                  15

Glu Glu Glu Arg Leu
            20
```

<210> SEQ ID NO 19
<211> LENGTH: 18
<212> TYPE: DNA
<213> ORGANISM: Artificial Sequence
<220> FEATURE:
<223> OTHER INFORMATION: X1F primer

<400> SEQUENCE: 19
ccatcacagc caatgacg 18

<210> SEQ ID NO 20
<211> LENGTH: 20
<212> TYPE: DNA
<213> ORGANISM: Artificial Sequence
<220> FEATURE:
<223> OTHER INFORMATION: X1R primer

<400> SEQUENCE: 20
agggggaggg tagagaggag 20

<210> SEQ ID NO 21
<211> LENGTH: 10171
<212> TYPE: DNA
<213> ORGANISM: Homo sapiens

<400> SEQUENCE: 21
ccggaaaatg gccgccgccg ccgccgccgc gccgagcagg aggcgaggag gagagactgc 60
tccataaaaa tacagactca ccagttcctg ctttgatgtg acatgtgact ccccagaata 120
caccttgctt ctgtagacca gctccaacag gattccatgg tagctgggat gttagggctc 180
agggaagaaa agtcagaaga ccaggacctc cagggcctca aggacaaacc cctcaagttt 240
aaaaaggtga agaaagataa gaaagaagag aaagagggca agcatgagcc cgtgcagcca 300
tcagcccacc actctgctga gcccgcagag gcaggcaaag cagagacatc agaagggtca 360
ggctccgccc cggctgtgcc ggaagcttct gcctccccca aacagcggcg ctccatcatc 420
cgtgaccggg gacccatgta tgatgacccc accctgcctg aaggctggac acggaagctt 480
aagcaaagga aatctggccg ctctgctggg aagtatgatg tgtatttgat caatccccag 540
ggaaaagcct ttcgctctaa agtggagttg attgcgtact tcgaaaaggt aggcgacaca 600
tccctggacc ctaatgattt tgacttcacg gtaactggga gagggagccc ctcccggcga 660
gagcagaaac cacctaagaa gcccaaatct cccaaagctc caggaactgg cagaggccgg 720
ggacgcccca aagggagcgg caccacgaga cccaaggcgg ccacgtcaga gggtgtgcag 780
gtgaaaaggg tcctggagaa aagtcctggg aagctccttg tcaagatgcc ttttcaaact 840
tcgccagggg gcaaggctga gggggggtggg gccaccacat ccacccaggt catggtgatc 900
aaacgccccg gcaggaagcg aaaagctgag gccgaccctc aggccattcc caagaaacgg 960
ggccgaaagc cggggagtgt ggtggcagcc gctgccgccg aggccaaaaa gaaagccgtg 1020
aaggagtctt ctatccgatc tgtgcaggag accgtactcc ccatcaagaa gcgcaagacc 1080
cgggagacgg tcagcatcga ggtcaaggaa gtggtgaagc ccctgctggt gtccaccctc 1140
ggtgagaaga gcgggaaagg actgaagacc tgtaagagcc ctgggcggaa aagcaaggag 1200
agcagcccca aggggcgcag cagcagcgcc tcctcacccc ccaagaagga gcaccaccac 1260
catcaccacc actcagagtc cccaaaggcc cccgtgccac tgctcccacc cctgccccca 1320
cctccacctg agcccgagag ctccgaggac cccaccagcc cccctgagcc ccaggacttg 1380
agcagcagcg tctgcaaaga ggagaagatg cccagaggag gctcactgga gagcgacggc 1440
tgccccaagg agccagctaa gactcagccc gcggttgcca ccgccgccac ggccgcagaa 1500
aagtacaaac accgagggga gggagagcgc aaagacattg tttcatcctc catgccaagg 1560
ccaaacagag aggagcctgt ggacagccgg acgcccgtga ccgagagagt tagctgactt 1620
tacacggagc ggattgcaaa gcaaaccaac aagaataaag gcagctgttg tctcttctcc 1680
ttatgggtag ggctctgaca aagcttcccg attaactgaa ataaaaaata tttttttttc 1740
tttcagtaaa cttagagttt cgtggcttca gggtgggagt agttggagca ttggggatgt 1800

-continued

```
ttttcttacc gacaagcaca gtcaggttga agacctaacc agggccagaa gtagctttgc   1860
acttttctaa actaggctcc ttcaacaagg cttgctgcag atactactga ccagacaagc   1920
tgttgaccag gcacctcccc tcccgcccaa acctttcccc catgtggtcg ttagagacag   1980
agcgacagag cagttgagag gacactcccg ttttcggtgc catcagtgcc ccgtctacag   2040
ctcccccagc tccccccacc tcccccactc ccaaccacgt tgggacaggg aggtgtgagg   2100
caggagagac agttggattc tttagagaag atggatatga ccagtggcta tggcctgtgc   2160
gatcccaccc gtggtggctc aagtctggcc ccacaccagc cccaatccaa aactggcaag   2220
gacgcttcac aggacaggaa agtggcacct gtctgctcca gctctggcat ggctaggagg   2280
ggggagtccc ttgaactact gggtgtagac tggcctgaac cacaggagag gatggcccag   2340
ggtgaggtgg catggtccat tctcaaggga cgtcctccaa cgggtggcgc tagaggccat   2400
ggaggcagta ggacaaggtg caggcaggct ggcctggggt caggccgggc agagcacagc   2460
ggggtgagag ggattcctaa tcactcagag cagtctgtga cttagtggac aggggagggg   2520
gcaaaggggg aggagaagaa aatgttcttc cagttacttt ccaattctcc tttagggaca   2580
gcttagaatt atttgcacta ttgagtcttc atgttcccac ttcaaaacaa acagatgctc   2640
tgagagcaaa ctggcttgaa ttggtgacat ttagtccctc aagccaccag atgtgacagt   2700
gttgagaact acctggattt gtatatatac ctgcgcttgt tttaaagtgg gctcagcaca   2760
tagggttccc acgaagctcc gaaactctaa gtgtttgctg caattttata aggacttcct   2820
gattggtttc tcttctcccc ttccatttct gccttttgtt catttcatcc tttcacttct   2880
ttcccttcct ccgtcctcct ccttcctagt tcatcccttc tcttccaggc agccgcggtg   2940
cccaaccaca cttgtcggct ccagtcccca gaactctgcc tgccctttgt cctcctgctg   3000
ccagtaccag ccccaccctg ttttgagccc tgaggaggcc ttgggctctg ctgagtccga   3060
cctggcctgt ctgtgaagag caagagagca gcaaggtctt gctctcctag gtagcccccct  3120
cttccctggt aagaaaaagc aaaaggcatt tcccaccctg aacaacgagc cttttcaccc   3180
ttctactcta gagaagtgga ctggaggagc tgggcccgat ttggtagttg aggaaagcac   3240
agaggcctcc tgtggcctgc cagtcatcga gtggcccaac aggggctcca tgccagccga   3300
ccttgacctc actcagaagt ccagagtcta gcgtagtgca gcagggcagt agcggtacca   3360
atgcagaact cccaagaccc gagctgggac cagtacctgg gtccccagcc cttcctctgc   3420
tcccccttttt ccctcggagt tcttcttgaa tggcaatgtt ttgcttttgc tcgatgcaga  3480
cagggggcca gaacaccaca catttcactg tctgtctggt ccatagctgt ggtgtagggg   3540
cttagaggca tgggcttgct gtgggttttt aattgatcag ttttcatgtg ggatcccatc   3600
tttttaacct ctgttcagga agtccttatc tagctgcata tcttcatcat attggtatat   3660
ccttttctgt gtttacagag atgtctctta tatctaaatc tgtccaactg agaagtacct   3720
tatcaaagta gcaaatgaga cagcagtctt atgcttccag aaacacccac aggcatgtcc   3780
catgtgagct gctgccatga actgtcaagt gtgtgttgtc ttgtgtattt cagttattgt   3840
ccctggcttc cttactatgg tgtaatcatg aaggagtgaa acatcataga aactgtctag   3900
cacttccttg ccagtcttta gtgatcagga accatagttg acagttccaa tcagtagctt   3960
aagaaaaaac cgtgtttgtc tcttctggaa tggttagaag tgagggagtt tgccccgttc   4020
tgtttgtaga gtctcatagt tggactttct agcatatatg tgtccatttc cttatgctgt   4080
aaaagcaagt cctgcaacca aactcccatc agcccaatcc ctgatccctg atcccttcca   4140
cctgctctgc tgatgacccc cccagcttca cttctgactc ttccccagga agggaagggg   4200
```

-continued

```
ggtcagaaga gagggtgagt cctccagaac tcttcctcca aggacagaag gctcctgccc   4260
ccatagtggc ctcgaactcc tggcactacc aaaggacact tatccacgag agcgcagcat   4320
ccgaccaggt tgtcactgag aagatgttta ttttggtcag ttgggttttt atgtattata   4380
cttagtcaaa tgtaatgtgg cttctggaat cattgtccag agctgcttcc ccgtcacctg   4440
ggcgtcatct ggtcctggta agaggagtgc gtggcccacc aggcccccct gtcacccatg   4500
acagttcatt cagggccgat ggggcagtcg tggttgggaa cacagcattt caagcgtcac   4560
tttatttcat tcgggcccca cctgcagctc cctcaaagag gcagttgccc agcctctttc   4620
ccttccagtt tattccagag ctgccagtgg ggcctgaggc tccttagggt tttctctcta   4680
tttccccctt tcttcctcat tccctcgtct ttcccaaagg catcacgagt cagtcgcctt   4740
tcagcaggca gccttggcgg tttatcgccc tggcaggcag gggccctgca gctctcatgc   4800
tgcccctgcc ttggggtcag gttgacagga ggttggaggg aaagccttaa gctgcaggat   4860
tctcaccagc tgtgtccggc ccagttttgg ggtgtgacct caatttcaat tttgtctgta   4920
cttgaacatt atgaagatgg gggcctcttt cagtgaattt gtgaacagca gaattgaccg   4980
acagctttcc agtacccatg gggctaggtc attaaggcca catccacagt ctcccccacc   5040
cttgttccag ttgttagtta ctacctcctc tcctgacaat actgtatgtc gtcgagctcc   5100
ccccaggtct acccctcccg gccctgcctg ctggtgggct tgtcatagcc agtgggattg   5160
ccggtcttga cagctcagtg agctggagat acttggtcac agccaggcgc tagcacagct   5220
cccttctgtt gatgctgtat tcccatatca aaagacacag gggacaccca gaaacgccac   5280
atcccccaat ccatcagtgc caaactagcc aacggcccca gcttctcagc tcgctggatg   5340
gcggaagctg ctactcgtga gcgccagtgc gggtgcagac aatcttctgt tgggtggcat   5400
cattccaggc ccgaagcatg aacagtgcac ctgggacagg gagcagcccc aaattgtcac   5460
ctgcttctct gcccagcttt tcattgctgt gacagtgatg gcgaaagagg gtaataacca   5520
gacacaaact gccaagttgg gtggagaaag gagtttcttt agctgacaga atctctgaat   5580
tttaaatcac ttagtaagcg gctcaagccc aggagggagc agagggatac gagcggagtc   5640
ccctgcgcgg gaccatctgg aattggttta gcccaagtgg agcctgacag ccagaactct   5700
gtgtcccccg tctaaccaca gctccttttc cagagcattc cagtcaggct ctctgggctg   5760
actgggccag gggaggttac aggtaccagt tctttaagaa gatctttggg catatacatt   5820
tttagcctgt gtcattgccc caaatggatt cctgtttcaa gttcacacct gcagattcta   5880
ggacctgtgt cctagacttc agggagtcag ctgtttctag agttcctacc atggagtggg   5940
tctggaggac ctgcccggtg ggggggcaga gccctgctcc ctccgggtct tcctactctt   6000
ctctctgctc tgacgggatt tgttgattct ctccattttg gtgtctttct cttttagata   6060
ttgtatcaat ctttagaaaa ggcatagtct acttgttata aatcgttagg atactgcctc   6120
ccccagggtc taaaattaca tattagaggg gaaaagctga acactgaagt cagttctcaa   6180
caatttagaa ggaaaaccta gaaaacattt ggcagaaaat tacatttcga tgtttttgaa   6240
tgaatacgag caagctttta caacagtgct gatctaaaaa tacttagcac ttggcctgag   6300
atgcctggtg agcattacag gcaaggggaa tctggaggta gccgacctga ggacatggct   6360
tctgaacctg tcttttggga gtggtatgga aggtggagcg ttcaccagtg acctggaagg   6420
cccagcacca ccctccttcc cactcttctc atcttgacag agcctgcccc agcgctgacg   6480
tgtcaggaaa acacccaggg aactaggaag gcacttctgc ctgaggggca gcctgccttg   6540
cccactcctg ctctgctcgc ctcggatcag ctgagccttc tgagctggcc tctcactgcc   6600
```

```
tccccaaggc cccctgcctg ccctgtcagg aggcagaagg aagcaggtgt gagggcagtg   6660
caaggaggga gcacaacccc cagctcccgc tccgggctcc gacttgtgca caggcagagc   6720
ccagaccctg gaggaaatcc tacctttgaa ttcaagaaca tttggggaat ttggaaatct   6780
ctttgccccc aaacccccat tctgtcctac ctttaatcag gtcctgctca gcagtgagag   6840
cagatgaggt gaaaaggcca agaggtttgg ctcctgccca ctgatagccc ctctccccgc   6900
agtgtttgtg tgtcaagtgg caaagctgtt cttcctggtg accctgatta tatccagtaa   6960
cacatagact gtgcgcatag gcctgctttg tctcctctat cctgggcttt tgttttgctt   7020
tttagttttg cttttagttt ttctgtccct tttatttaac gcaccgacta gacacacaaa   7080
gcagttgaat tttatatat atatctgtat attgcacaat tataaactca ttttgcttgt   7140
ggctccacac acacaaaaaa agacctgtta aaattatacc tgttgcttaa ttacaatatt   7200
tctgataacc atagcatagg acaagggaaa ataaaaaaag aaaaaaaaga aaaaaaaacg   7260
acaaatctgt ctgctggtca cttcttctgt ccaagcagat tcgtggtctt ttcctcgctt   7320
ctttcaaggg ctttcctgtg ccaggtgaag gaggctccag gcagcaccca ggttttgcac   7380
tcttgtttct cccgtgcttg tgaaagaggt cccaaggttc tgggtgcagg agcgctccct   7440
tgacctgctg aagtccggaa cgtagtcggc acagcctggt cgccttccac ctctgggagc   7500
tggagtccac tggggtggcc tgactccccc agtccccttc ccgtgacctg gtcagggtga   7560
gcccatgtgg agtcagcctc gcaggcctcc ctgccagtag ggtccgagtg tgtttcatcc   7620
ttcccactct gtcgagcctg ggggctggag cggagacggg aggcctggcc tgtctcggaa   7680
cctgtgagct gcaccaggta gaacgccagg gaccccagaa tcatgtgcgt cagtccaagg   7740
ggtcccctcc aggagtagtg aagactccag aaatgtccct ttcttctccc ccatcctacg   7800
agtaattgca tttgcttttg taattcttaa tgagcaatat ctgctagaga gtttagctgt   7860
aacagttctt tttgatcatc tttttttaat aattagaaac accaaaaaaa tccagaaact   7920
tgttcttcca aagcagagag cattataatc accagggcca aaagcttccc tccctgctgt   7980
cattgcttct tctgaggcct gaatccaaaa gaaaaacagc cataggccct ttcagtggcc   8040
gggctacccg tgagcccttc ggaggaccag ggctggggca gcctctgggc ccacatccgg   8100
ggccagctcc ggcgtgtgtt cagtgttagc agtgggtcat gatgctcttt cccacccagc   8160
ctgggatagg ggcagaggag gcgaggaggc cgttgccgct gatgtttggc cgtgaacagg   8220
tgggtgtctg cgtgcgtcca cgtgcgtgtt ttctgactga catgaaatcg acgcccgagt   8280
tagcctcacc cggtgacctc tagccctgcc cggatggagc ggggcccacc cggttcagtg   8340
tttctgggga gctggacagt ggagtgcaaa aggcttgcag aacttgaagc ctgctccttc   8400
ccttgctacc acggcctcct ttccgtttga tttgtcactg cttcaatcaa taacagccgc   8460
tccagagtca gtagtcaatg aatatatgac caaatatcac caggactgtt actcaatgtg   8520
tgccgagccc ttgcccatgc tgggctcccg tgtatctgga cactgtaacg tgtgctgtgt   8580
ttgctcccct tccccttcct tctttgccct ttacttgtct ttctggggtt tttctgtttg   8640
ggtttggttt ggtttttatt tctccttttg tgttccaaac atgaggttct ctctactggt   8700
cctcttaact gtggtgttga ggcttatatt tgtgtaattt ttggtgggtg aaaggaattt   8760
tgctaagtaa atctcttctg tgtttgaact gaagtctgta ttgtaactat gtttaaagta   8820
attgttccag agacaaatat ttctagacac tttttcttta caaacaaaag cattcggagg   8880
gagggggatg gtgactgaga tgagagggga gagctgaaca gatgacccct gcccagatca   8940
gccagaagcc acccaaagca gtggagccca ggagtcccac tccaagccag caagccgaat   9000
```

```
agctgatgtg ttgccacttt ccaagtcact gcaaaaccag gttttgttcc gcccagtgga   9060
ttcttgtttt gcttcccctc cccccgagat tattaccacc atcccgtgct tttaaggaaa   9120
ggcaagattg atgtttcctt gaggggagcc aggaggggat gtgtgtgtgc agagctgaag   9180
agctggggag aatggggctg ggcccaccca agcaggaggc tgggacgctc tgctgtgggc   9240
acaggtcagg ctaatgttgg cagatgcagc tcttcctgga caggccaggt ggtgggcatt   9300
ctctctccaa ggtgtgcccc gtgggcatta ctgtttaaga cacttccgtc acatcccacc   9360
ccatcctcca gggctcaaca ctgtgacatc tctattcccc accctcccct tcccagggca   9420
ataaaatgac catggagggg gcttgcactc tcttggctgt cacccgatcg ccagcaaaac   9480
ttagatgtga gaaaacccct tcccattcca tggcgaaaac atctccttag aaaagccatt   9540
accctcatta ggcatggttt tgggctccca aaacacctga cagcccctcc ctcctctgag   9600
aggcggagag tgctgactgt agtgaccatt gcatgccggg tgcagcatct ggaagagcta   9660
ggcagggtgt ctgcccccctc ctgagttgaa gtcatgctcc cctgtgccag cccagaggcc   9720
gagagctatg gacagcattg ccagtaacac aggccaccct gtgcagaagg gagctggctc   9780
cagcctggaa acctgtctga ggttgggaga ggtgcacttg gggcacaggg agaggccggg   9840
acacacttag ctggagatgt ctctaaaagc cctgtatcgt attcaccttc agtttttgtg   9900
ttttgggaca attactttag aaaataagta ggtcgtttta aaaacaaaaa ttattgattg   9960
ctttttgta gtgttcagaa aaaaggttct ttgtgtatag ccaaatgact gaaagcactg  10020
atatatttaa aaacaaaagg caatttatta aggaaatttg taccatttca gtaaacctgt  10080
ctgaatgtac ctgtatacgt ttcaaaaaca cccccccccc actgaatccc tgtaacctat  10140
ttattatata aagagtttgc cttataaatt t                                10171
```

<210> SEQ ID NO 22
<211> LENGTH: 10113
<212> TYPE: DNA
<213> ORGANISM: Homo sapiens

<400> SEQUENCE: 22

```
gctccataaa aatacagact caccagttcc tgctttgatg tgacatgtga ctccccagaa     60
tacaccttgc ttctgtagac cagctccaac aggattccat ggtagctggg atgttagggc    120
tcagggaaga aaagtcagaa gaccaggacc tccagggcct caaggacaaa cccctcaagt    180
ttaaaaaggt gaagaaagat aagaaagaag agaaagaggg caagcatgag cccgtgcagc    240
catcagccca ccactctgct gagcccgcag aggcaggcaa agcagagaca tcagaagggt    300
caggctccgc cccggctgtg ccggaagctt ctgcctcccc caaacagcgg cgctccatca    360
tccgtgaccg gggacccatg tatgatgacc ccaccctgcc tgaaggctgg acacggaagc    420
ttaagcaaag gaaatctggc cgctctgctg ggaagtatga tgtgtatttg atcaatcccc    480
agggaaaagc ctttcgctct aaagtggagt tgattgcgta cttcgaaaag gtaggcgaca    540
catccctgga ccctaatgat tttgacttca cggtaactgg gagagggagc ccctcccggc    600
gagagcagaa accacctaag aagcccaaat ctcccaaagc tccaggaact ggcagaggcc    660
ggggacgccc caaagggagc ggcaccacga gacccaaggc ggccacgtca gagggtgtgc    720
aggtgaaaag ggtcctggag aaaagtcctg ggaagctcct tgtcaagatg ccttttcaaa    780
cttcgccagg gggcaaggct gagggggggtg gggccaccac atccacccag gtcatggtga    840
tcaaacgccc cggcaggaag cgaaaagctg aggccgaccc tcaggccatt cccaagaaac    900
ggggccgaaa gccggggagt gtggtggcag ccgctgccgc cgaggccaaa aagaaagccg    960
```

```
tgaaggagtc ttctatccga tctgtgcagg agaccgtact ccccatcaag aagcgcaaga   1020
cccgggagac ggtcagcatc gaggtcaagg aagtggtgaa gcccctgctg gtgtccaccc   1080
tcggtgagaa gagcgggaaa ggactgaaga cctgtaagag ccctgggcgg aaaagcaagg   1140
agagcagccc caaggggcgc agcagcagcg cctcctcacc ccccaagaag gagcaccacc   1200
accatcacca ccactcagag tccccaaagg cccccgtgcc actgctccca cccctgcccc   1260
cacctccacc tgagcccgag agctccgagg accccaccag cccccctgag ccccaggact   1320
tgagcagcag cgtctgcaaa gaggagaaga tgcccagagg aggctcactg gagagcgacg   1380
gctgccccaa ggagccagct aagactcagc ccgcggttgc caccgccgcc acggccgcag   1440
aaaagtacaa acaccgaggg gagggagagc gcaaagacat tgtttcatcc tccatgccaa   1500
ggccaaacag agaggagcct gtggacagcc ggacgcccgt gaccgagaga gttagctgac   1560
tttacacgga gcggattgca aagcaaacca acaagaataa aggcagctgt tgtctcttct   1620
ccttatgggt agggctctga caaagcttcc cgattaactg aaataaaaaa tatttttttt   1680
tctttcagta aacttagagt ttcgtggctt cagggtggga gtagttggag cattggggat   1740
gtttttctta ccgacaagca cagtcaggtt gaagacctaa ccagggccag aagtagcttt   1800
gcacttttct aaactaggct ccttcaacaa ggcttgctgc agatactact gaccagacaa   1860
gctgttgacc aggcacctcc cctcccgccc aaacctttcc cccatgtggt cgttagagac   1920
agagcgacag agcagttgag aggacactcc cgttttcggt gccatcagtg ccccgtctac   1980
agctccccca gctcccccca cctcccccac tcccaaccac gttgggacag ggaggtgtga   2040
ggcaggagag acagttggat tctttagaga agatggatat gaccagtggc tatggcctgt   2100
gcgatcccac ccgtggtggc tcaagtctgg ccccacacca gccccaatcc aaaactggca   2160
aggacgcttc acaggacagg aaagtggcac ctgtctgctc cagctctggc atggctagga   2220
ggggggagtc ccttgaacta ctgggtgtag actggcctga accacaggag aggatggccc   2280
agggtgaggt ggcatggtcc attctcaagg gacgtcctcc aacgggtggc gctagaggcc   2340
atggaggcag taggacaagg tgcaggcagg ctggcctggg gtcaggccgg gcagagcaca   2400
gcggggtgag agggattcct aatcactcag agcagtctgt gacttagtgg acaggggagg   2460
gggcaaaggg ggaggagaag aaaatgttct tccagttact ttccaattct cctttaggga   2520
cagcttagaa ttatttgcac tattgagtct tcatgttccc acttcaaaac aaacagatgc   2580
tctgagagca aactggcttg aattggtgac atttagtccc tcaagccacc agatgtgaca   2640
gtgttgagaa ctacctggat ttgtatatat acctgcgctt gttttaaagt gggctcagca   2700
catagggttc ccacgaagct ccgaaactct aagtgtttgc tgcaatttta taaggacttc   2760
ctgattggtt tctcttctcc ccttccattt ctgccttttg ttcatttcat cctttcactt   2820
ctttcccttc ctccgtcctc ctccttccta gttcatccct tctcttccag gcagccgcgg   2880
tgcccaacca cacttgtcgg ctccagtccc cagaactctg cctgcccttt gtcctcctgc   2940
tgccagtacc agccccaccc tgttttgagc cctgaggagg ccttgggctc tgctgagtcc   3000
gacctggcct gtctgtgaag agcaagagag cagcaaggtc ttgctctcct aggtagcccc   3060
ctcttccctg gtaagaaaaa gcaaaaggca tttcccaccc tgaacaacga gccttttcac   3120
ccttctactc tagagaagtg gactggagga gctgggcccg atttggtagt tgaggaaagc   3180
acagaggcct cctgtggcct gccagtcatc gagtggccca acaggggctc catgccagcc   3240
gaccttgacc tcactcagaa gtccagagtc tagcgtagtg cagcagggca gtagcggtac   3300
caatgcagaa ctcccaagac ccgagctggg accagtacct gggtccccag cccttcctct   3360
```

-continued

```
gctccccctt ttccctcgga gttcttcttg aatggcaatg ttttgctttt gctcgatgca   3420
gacaggggc cagaacacca cacatttcac tgtctgtctg gtccatagct gtggtgtagg   3480
ggcttagagg catgggcttg ctgtgggttt ttaattgatc agttttcatg tgggatccca   3540
tctttttaac ctctgttcag gaagtcctta tctagctgca tatcttcatc atattggtat   3600
atccttttct gtgtttacag agatgtctct tatatctaaa tctgtccaac tgagaagtac   3660
cttatcaaag tagcaaatga gacagcagtc ttatgcttcc agaaacaccc acaggcatgt   3720
cccatgtgag ctgctgccat gaactgtcaa gtgtgtgttg tcttgtgtat ttcagttatt   3780
gtccctggct tccttactat ggtgtaatca tgaaggagtg aaacatcata gaaactgtct   3840
agcacttcct tgccagtctt tagtgatcag gaaccatagt tgacagttcc aatcagtagc   3900
ttaagaaaaa accgtgtttg tctcttctgg aatggttaga agtgagggag tttgccccgt   3960
tctgtttgta gagtctcata gttggacttt ctagcatata tgtgtccatt tccttatgct   4020
gtaaaagcaa gtcctgcaac caaactccca tcagcccaat ccctgatccc tgatcccttc   4080
cacctgctct gctgatgacc cccccagctt cacttctgac tcttccccag gaagggaagg   4140
ggggtcagaa gagagggtga gtcctccaga actcttcctc caaggacaga aggctcctgc   4200
ccccatagtg gcctcgaact cctggcacta ccaaaggaca cttatccacg agagcgcagc   4260
atccgaccag gttgtcactg agaagatgtt tattttggtc agttgggttt ttatgtatta   4320
tacttagtca aatgtaatgt ggcttctgga atcattgtcc agagctgctt ccccgtcacc   4380
tgggcgtcat ctggtcctgg taagaggagt gcgtggccca ccaggccccc ctgtcaccca   4440
tgacagttca ttcagggccg atggggcagt cgtggttggg aacacagcat ttcaagcgtc   4500
actttatttc attcgggccc cacctgcagc tccctcaaag aggcagttgc ccagcctctt   4560
tcccttccag tttattccag agctgccagt ggggcctgag gctccttagg gttttctctc   4620
tatttccccc tttcttcctc attccctcgt ctttcccaaa ggcatcacga gtcagtcgcc   4680
tttcagcagg cagccttggc ggtttatcgc cctggcaggc aggggccctg cagctctcat   4740
gctgcccctg ccttggggtc aggttgacag gaggttggag ggaaagcctt aagctgcagg   4800
attctcacca gctgtgtccg gcccagtttt ggggtgtgac ctcaatttca attttgtctg   4860
tacttgaaca ttatgaagat gggggcctct ttcagtgaat ttgtgaacag cagaattgac   4920
cgacagcttt ccagtaccca tggggctagg tcattaaggc cacatccaca gtctccccca   4980
cccttgttcc agttgttagt tactacctcc tctcctgaca atactgtatg tcgtcgagct   5040
ccccccaggt ctacccctcc cggccctgcc tgctggtggg cttgtcatag ccagtgggat   5100
tgccggtctt gacagctcag tgagctggag atacttggtc acagccaggc gctagcacag   5160
ctcccttctg ttgatgctgt attcccatat caaaagacac aggggacacc cagaaacgcc   5220
acatccccca atccatcagt gccaaactag ccaacggccc cagcttctca gctcgctgga   5280
tggcggaagc tgctactcgt gagcgccagt gcgggtgcag acaatcttct gttgggtggc   5340
atcattccag gcccgaagca tgaacagtgc acctgggaca gggagcagcc ccaaattgtc   5400
acctgcttct ctgcccagct tttcattgct gtgacagtga tggcgaaaga gggtaataac   5460
cagacacaaa ctgccaagtt gggtggagaa aggagtttct ttagctgaca gaatctctga   5520
attttaaatc acttagtaag cggctcaagc ccaggaggga gcagagggat acgagcggag   5580
tcccctgcgc gggaccatct ggaattggtt tagcccaagt ggagcctgac agccagaact   5640
ctgtgtcccc cgtctaacca cagctccttt tccagagcat tccagtcagg ctctctgggc   5700
tgactgggcc aggggaggtt acaggtacca gttctttaag aagatctttg ggcatataca   5760
```

-continued

```
tttttagcct gtgtcattgc cccaaatgga ttcctgtttc aagttcacac ctgcagattc   5820
taggacctgt gtcctagact tcagggagtc agctgtttct agagttccta ccatggagtg   5880
ggtctggagg acctgcccgg tgggggggca gagccctgct ccctccgggt cttcctactc   5940
ttctctctgc tctgacggga tttgttgatt ctctccattt tggtgtcttt ctcttttaga   6000
tattgtatca atctttagaa aaggcatagt ctacttgtta taaatcgtta ggatactgcc   6060
tcccccaggg tctaaaatta catattagag gggaaaagct gaacactgaa gtcagttctc   6120
aacaatttag aaggaaaacc tagaaaacat ttggcagaaa attacatttc gatgtttttg   6180
aatgaatacg agcaagcttt tacaacagtg ctgatctaaa aatacttagc acttggcctg   6240
agatgcctgg tgagcattac aggcaagggg aatctggagg tagccgacct gaggacatgg   6300
cttctgaacc tgtcttttgg gagtggtatg gaaggtggag cgttcaccag tgacctggaa   6360
ggcccagcac caccctcctt cccactcttc tcatcttgac agagcctgcc ccagcgctga   6420
cgtgtcagga aaacacccag ggaactagga aggcacttct gcctgagggg cagcctgcct   6480
tgcccactcc tgctctgctc gcctcggatc agctgagcct tctgagctgg cctctcactg   6540
cctccccaag gccccctgcc tgccctgtca ggaggcagaa ggaagcaggt gtgagggcag   6600
tgcaaggagg gagcacaacc cccagctccc gctccgggct ccgacttgtg cacaggcaga   6660
gcccagaccc tggaggaaat cctacctttg aattcaagaa catttgggga atttggaaat   6720
ctctttgccc ccaaaccccc attctgtcct acctttaatc aggtcctgct cagcagtgag   6780
agcagatgag gtgaaaaggc caagaggttt ggctcctgcc cactgatagc ccctctcccc   6840
gcagtgtttg tgtgtcaagt ggcaaagctg ttcttcctgg tgaccctgat tatatccagt   6900
aacacataga ctgtgcgcat aggcctgctt tgtctcctct atcctgggct tttgttttgc   6960
tttttagttt tgcttttagt ttttctgtcc cttttattta acgcaccgac tagacacaca   7020
aagcagttga atttttatat atatatctgt atattgcaca attataaact catttttgctt   7080
gtggctccac acacacaaaa aaagacctgt taaaattata cctgttgctt aattacaata   7140
tttctgataa ccatagcata ggacaaggga aaataaaaaa agaaaaaaaa gaaaaaaaaa   7200
cgacaaatct gtctgctggt cacttcttct gtccaagcag attcgtggtc ttttcctcgc   7260
ttctttcaag ggctttcctg tgccaggtga aggaggctcc aggcagcacc caggttttgc   7320
actcttgttt ctcccgtgct tgtgaaagag gtcccaaggt tctgggtgca ggagcgctcc   7380
cttgacctgc tgaagtccgg aacgtagtcg gcacagcctg gtcgccttcc acctctggga   7440
gctggagtcc actggggtgg cctgactccc ccagtcccct tcccgtgacc tggtcagggt   7500
gagcccatgt ggagtcagcc tcgcaggcct ccctgccagt agggtccgag tgtgtttcat   7560
ccttcccact ctgtcgagcc tgggggctgg agcggagacg ggaggcctgg cctgtctcgg   7620
aacctgtgag ctgcaccagg tagaacgcca gggaccccag aatcatgtgc gtcagtccaa   7680
ggggtcccct ccaggagtag tgaagactcc agaaatgtcc ctttcttctc ccccatccta   7740
cgagtaattg catttgcttt tgtaattctt aatgagcaat atctgctaga gagtttagct   7800
gtaacagttc tttttgatca tcttttttta ataattagaa acaccaaaaa aatccagaaa   7860
cttgttcttc caaagcagag agcattataa tcaccagggc caaaagcttc cctccctgct   7920
gtcattgctt cttctgaggc ctgaatccaa aagaaaaaca gccataggcc ctttcagtgg   7980
ccgggctacc cgtgagccct tcggaggacc agggctgggg cagcctctgg gcccacatcc   8040
ggggccagct ccggcgtgtg ttcagtgtta gcagtgggtc atgatgctct ttcccaccca   8100
gcctgggata ggggcagagg aggcgaggag gccgttgccg ctgatgtttg gccgtgaaca   8160
```

```
ggtgggtgtc tgcgtgcgtc cacgtgcgtg ttttctgact gacatgaaat cgacgcccga   8220

gttagcctca cccggtgacc tctagccctg cccggatgga gcggggccca cccggttcag   8280

tgtttctggg gagctggaca gtggagtgca aaaggcttgc agaacttgaa gcctgctcct   8340

tcccttgcta ccacggcctc ctttccgttt gatttgtcac tgcttcaatc aataacagcc   8400

gctccagagt cagtagtcaa tgaatatatg accaaatatc accaggactg ttactcaatg   8460

tgtgccgagc ccttgcccat gctgggctcc cgtgtatctg gacactgtaa cgtgtgctgt   8520

gtttgctccc cttccccttc cttctttgcc ctttacttgt ctttctgggg tttttctgtt   8580

tgggtttggt ttggttttta tttctccttt tgtgttccaa acatgaggtt ctctctactg   8640

gtcctcttaa ctgtggtgtt gaggcttata tttgtgtaat ttttggtggg tgaaaggaat   8700

tttgctaagt aaatctcttc tgtgtttgaa ctgaagtctg tattgtaact atgtttaaag   8760

taattgttcc agagacaaat atttctagac actttttctt tacaaacaaa agcattcgga   8820

gggaggggga tggtgactga gatgagaggg gagagctgaa cagatgaccc ctgcccagat   8880

cagccagaag ccacccaaag cagtggagcc caggagtccc actccaagcc agcaagccga   8940

atagctgatg tgttgccact ttccaagtca ctgcaaaacc aggttttgtt ccgcccagtg   9000

gattcttgtt ttgcttcccc tccccccgag attattacca ccatcccgtg cttttaagga   9060

aaggcaagat tgatgtttcc ttgaggggag ccaggagggg atgtgtgtgt gcagagctga   9120

agagctgggg agaatggggc tgggcccacc caagcaggag gctgggacgc tctgctgtgg   9180

gcacaggtca ggctaatgtt ggcagatgca gctcttcctg gacaggccag gtggtgggca   9240

ttctctctcc aaggtgtgcc ccgtgggcat tactgtttaa gacacttccg tcacatccca   9300

ccccatcctc cagggctcaa cactgtgaca tctctattcc ccaccctccc cttcccaggg   9360

caataaaatg accatggagg gggcttgcac tctcttggct gtcacccgat cgccagcaaa   9420

acttagatgt gagaaaaccc cttcccattc catggcgaaa acatctcctt agaaaagcca   9480

ttaccctcat taggcatggt tttgggctcc caaaacacct gacagcccct ccctcctctg   9540

agaggcggag agtgctgact gtagtgacca ttgcatgccg ggtgcagcat ctggaagagc   9600

taggcagggt gtctgccccc tcctgagttg aagtcatgct cccctgtgcc agcccagagg   9660

ccgagagcta tggacagcat tgccagtaac acaggccacc ctgtgcagaa gggagctggc   9720

tccagcctgg aaacctgtct gaggttggga gaggtgcact tggggcacag ggagaggccg   9780

ggacacactt agctggagat gtctctaaaa gccctgtatc gtattcacct tcagtttttg   9840

tgttttggga caattacttt agaaaataag taggtcgttt taaaaacaaa aattattgat   9900

tgcttttttg tagtgttcag aaaaaaggtt ctttgtgtat agccaaatga ctgaaagcac   9960

tgatatattt aaaaacaaaa ggcaatttat taaggaaatt tgtaccattt cagtaaacct  10020

gtctgaatgt acctgtatac gtttcaaaaa cacccccccc ccactgaatc cctgtaacct  10080

atttattata taaagagttt gccttataaa ttt                               10113
```

```
<210> SEQ ID NO 23
<211> LENGTH: 10182
<212> TYPE: DNA
<213> ORGANISM: Homo sapiens

<400> SEQUENCE: 23

ccggaaattg gccgccgccg ccgccgccgc gccgagcgga ggaggaggag gaggcgagga     60

ggagagactg ctccataaaa atacagactc accagttcct gctttgatgt gacatgtgac    120

tccccagaat acaccttgct tctgtagacc agctccaaca ggattccatg gtagctggga    180
```

```
tgttagggct cagggaagaa aagtcagaag accaggacct ccagggcctc aaggacaaac    240

ccctcaagtt taaaaaggtg aagaaagata agaaagaaga gaaagagggc aagcatgagc    300

ccgtgcagcc atcagcccac cactctgctg agcccgcaga ggcaggcaaa gcagagacat    360

cagaagggtc aggctccgcc ccggctgtgc cggaagcttc tgcctccccc aaacagcggc    420

gctccatcat ccgtgaccgg ggacccatgt atgatgaccc caccctgcct gaaggctgga    480

cacggaagct taagcaaagg aaatctggcc gctctgctgg gaagtatgat gtgtatttga    540

tcaatcccca gggaaaagcc tttcgctcta aagtggagtt gattgcgtac ttcgaaaagg    600

taggcgacac atccctggac cctaatgatt ttgacttcac ggtaactggg agagggagcc    660

cctcccggcg agagcagaaa ccacctaaga agcccaaatc tcccaaagct ccaggaactg    720

gcagaggccg gggacgcccc aaagggagcg gcaccacgag acccaaggcg gccacgtcag    780

agggtgtgca ggtgaaaagg gtcctggaga aaagtcctgg gaagctcctt gtcaagatgc    840

cttttcaaac ttcgccaggg ggcaaggctg aggggggtgg ggccaccaca tccacccagg    900

tcatggtgat caaacgcccc ggcaggaagc gaaaagctga ggccgaccct caggccattc    960

ccaagaaacg gggccgaaag ccggggagtg tggtggcagc cgctgccgcc gaggccaaaa   1020

agaaagccgt gaaggagtct tctatccgat ctgtgcagga gaccgtactc cccatcaaga   1080

agcgcaagac ccgggagacg gtcagcatcg aggtcaagga agtggtgaag cccctgctgg   1140

tgtccaccct cggtgagaag agcgggaaag gactgaagac ctgtaagagc cctgggcgga   1200

aaagcaagga gagcagcccc aaggggcgca gcagcagcgc ctcctcaccc cccaagaagg   1260

agcaccacca ccatcaccac cactcagagt ccccaaaggc cccgtgcca ctgctcccac   1320

ccctgccccc acctccacct gagcccgaga gctccgagga ccccaccagc ccccctgagc   1380

cccaggactt gagcagcagc gtctgcaaag aggagaagat gcccagagga ggctcactgg   1440

agagcgacgg ctgccccaag gagccagcta agactcagcc cgcggttgcc accgccgcca   1500

cggccgcaga aaagtacaaa caccgagggg agggagagcg caaagacatt gtttcatcct   1560

ccatgccaag gccaaacaga gaggagcctg tggacagccg gacgcccgtg accgagagag   1620

ttagctgact ttacacggag cggattgcaa agcaaaccaa caagaataaa ggcagctgtt   1680

gtctcttctc cttatgggta gggctctgac aaagcttccc gattaactga aataaaaaat   1740

attttttttt ctttcagtaa acttagagtt tcgtggcttc agggtgggag tagttggagc   1800

attggggatg tttttcttac cgacaagcac agtcaggttg aagacctaac cagggccaga   1860

agtagctttg cacttttcta aactaggctc cttcaacaag gcttgctgca gatactactg   1920

accagacaag ctgttgacca ggcacctccc ctcccgccca aacctttccc ccatgtggtc   1980

gttagagaca gagcgacaga gcagttgaga ggacactccc gttttcggtg ccatcagtgc   2040

cccgtctaca gctcccccag ctccccccac ctcccccact cccaaccacg ttgggacagg   2100

gaggtgtgag gcaggagaga cagttggatt ctttagagaa gatggatatg accagtggct   2160

atggcctgtg cgatcccacc cgtggtggct caagtctggc cccacaccag ccccaatcca   2220

aaactggcaa ggacgcttca caggacagga aagtggcacc tgtctgctcc agctctggca   2280

tggctaggag gggggagtcc cttgaactac tgggtgtaga ctggcctgaa ccacaggaga   2340

ggatggccca gggtgaggtg gcatggtcca ttctcaaggg acgtcctcca acgggtggcg   2400

ctagaggcca tggaggcagt aggacaaggt gcaggcaggc tggcctgggg tcaggccggg   2460

cagagcacag cggggtgaga gggattccta atcactcaga gcagtctgtg acttagtgga   2520

caggggaggg ggcaaagggg gaggagaaga aaatgttctt ccagttactt tccaattctc   2580
```

-continued

```
ctttagggac agcttagaat tatttgcact attgagtctt catgttccca cttcaaaaca   2640
aacagatgct ctgagagcaa actggcttga attggtgaca tttagtccct caagccacca   2700
gatgtgacag tgttgagaac tacctggatt tgtatatata cctgcgcttg ttttaaagtg   2760
ggctcagcac atagggttcc cacgaagctc cgaaactcta agtgtttgct gcaattttat   2820
aaggacttcc tgattggttt ctcttctccc cttccatttc tgccttttgt tcatttcatc   2880
ctttcacttc tttcccttcc tccgtcctcc tccttcctag ttcatccctt ctcttccagg   2940
cagccgcggt gcccaaccac acttgtcggc tccagtcccc agaactctgc ctgccctttg   3000
tcctcctgct gccagtacca gccccaccct gttttgagcc ctgaggaggc cttgggctct   3060
gctgagtccg acctggcctg tctgtgaaga gcaagagagc agcaaggtct tgctctccta   3120
ggtagccccc tcttccctgg taagaaaaag caaaaggcat ttcccaccct gaacaacgag   3180
ccttttcacc cttctactct agagaagtgg actggaggag ctgggcccga tttggtagtt   3240
gaggaaagca cagaggcctc ctgtggcctg ccagtcatcg agtggcccaa caggggctcc   3300
atgccagccg accttgacct cactcagaag tccagagtct agcgtagtgc agcagggcag   3360
tagcggtacc aatgcagaac tcccaagacc cgagctggga ccagtacctg ggtccccagc   3420
ccttcctctg ctcccccttt tccctcggag ttcttcttga atggcaatgt tttgcttttg   3480
ctcgatgcag acagggggcc agaacaccac acatttcact gtctgtctgg tccatagctg   3540
tggtgtaggg gcttagaggc atgggcttgc tgtgggtttt taattgatca gttttcatgt   3600
gggatcccat ctttttaacc tctgttcagg aagtccttat ctagctgcat atcttcatca   3660
tattggtata tccttttctg tgtttacaga gatgtctctt atatctaaat ctgtccaact   3720
gagaagtacc ttatcaaagt agcaaatgag acagcagtct tatgcttcca gaaacaccca   3780
caggcatgtc ccatgtgagc tgctgccatg aactgtcaag tgtgtgttgt cttgtgtatt   3840
tcagttattg tccctggctt ccttactatg gtgtaatcat gaaggagtga aacatcatag   3900
aaactgtcta gcacttcctt gccagtcttt agtgatcagg aaccatagtt gacagttcca   3960
atcagtagct taagaaaaaa ccgtgtttgt ctcttctgga atggttagaa gtgagggagt   4020
ttgccccgtt ctgtttgtag agtctcatag ttggactttc tagcatatat gtgtccattt   4080
ccttatgctg taaaagcaag tcctgcaacc aaactcccat cagcccaatc cctgatccct   4140
gatcccttcc acctgctctg ctgatgaccc ccccagcttc acttctgact cttccccagg   4200
aagggaaggg gggtcagaag agagggtgag tcctccagaa ctcttcctcc aaggacagaa   4260
ggctcctgcc cccatagtgg cctcgaactc ctggcactac caaaggacac ttatccacga   4320
gagcgcagca tccgaccagg ttgtcactga gaagatgttt attttggtca gttgggtttt   4380
tatgtattat acttagtcaa atgtaatgtg gcttctggaa tcattgtcca gagctgcttc   4440
cccgtcacct gggcgtcatc tggtcctggt aagaggagtg cgtggcccac caggcccccc   4500
tgtcacccat gacagttcat tcagggccga tggggcagtc gtggttggga acacagcatt   4560
tcaagcgtca ctttatttca ttcgggcccc acctgcagct ccctcaaaga ggcagttgcc   4620
cagcctcttt cccttccagt ttattccaga gctgccagtg gggcctgagg ctccttaggg   4680
ttttctctct atttccccct ttcttcctca ttccctcgtc tttcccaaag gcatcacgag   4740
tcagtcgcct ttcagcaggc agccttggcg gtttatcgcc ctggcaggca ggggccctgc   4800
agctctcatg ctgcccctgc cttggggtca ggttgacagg aggttggagg gaaagcctta   4860
agctgcagga ttctcaccag ctgtgtccgg cccagttttg gggtgtgacc tcaatttcaa   4920
ttttgtctgt acttgaacat tatgaagatg gggcctcttt tcagtgaatt tgtgaacagc   4980
```

-continued

```
agaattgacc gacagctttc cagtacccat ggggctaggt cattaaggcc acatccacag   5040
tctcccccac ccttgttcca gttgttagtt actacctcct ctcctgacaa tactgtatgt   5100
cgtcgagctc cccccaggtc taccccctccc ggccctgcct gctggtgggc ttgtcatagc   5160
cagtgggatt gccggtcttg acagctcagt gagctggaga tacttggtca cagccaggcg   5220
ctagcacagc tcccttctgt tgatgctgta ttcccatatc aaaagacaca ggggacaccc   5280
agaaacgcca catcccccaa tccatcagtg ccaaactagc caacggcccc agcttctcag   5340
ctcgctggat ggcggaagct gctactcgtg agcgccagtg cgggtgcaga caatcttctg   5400
ttgggtggca tcattccagg cccgaagcat gaacagtgca cctgggacag ggagcagccc   5460
caaattgtca cctgcttctc tgcccagctt ttcattgctg tgacagtgat ggcgaaagag   5520
ggtaataacc agacacaaac tgccaagttg ggtggagaaa ggagtttctt tagctgacag   5580
aatctctgaa ttttaaatca cttagtaagc ggctcaagcc caggagggag cagagggata   5640
cgagcggagt cccctgcgcg ggaccatctg gaattggttt agcccaagtg gagcctgaca   5700
gccagaactc tgtgtccccc gtctaaccac agctcctttt ccagagcatt ccagtcaggc   5760
tctctgggct gactgggcca ggggaggtta caggtaccag ttctttaaga agatctttgg   5820
gcatatacat ttttagcctg tgtcattgcc ccaaatggat tcctgtttca agttcacacc   5880
tgcagattct aggacctgtg tcctagactt cagggagtca gctgtttcta gagttcctac   5940
catggagtgg gtctggagga cctgcccggt ggggggggcag agccctgctc cctccgggtc   6000
ttcctactct tctctctgct ctgacgggat ttgttgattc tctccatttt ggtgtctttc   6060
tcttttagat attgtatcaa tctttagaaa aggcatagtc tacttgttat aaatcgttag   6120
gatactgcct cccccagggt ctaaaattac atattagagg ggaaaagctg aacactgaag   6180
tcagttctca acaatttaga aggaaaacct agaaaacatt tggcagaaaa ttacatttcg   6240
atgtttttga atgaatacga gcaagctttt acaacagtgc tgatctaaaa atacttagca   6300
cttggcctga gatgcctggt gagcattaca ggcaagggga atctggaggt agccgacctg   6360
aggacatggc ttctgaacct gtcttttggg agtggtatgg aaggtggagc gttcaccagt   6420
gacctggaag gcccagcacc accctccttc ccactcttct catcttgaca gagcctgccc   6480
cagcgctgac gtgtcaggaa aacacccagg gaactaggaa ggcacttctg cctgaggggc   6540
agcctgcctt gcccactcct gctctgctcg cctcggatca gctgagcctt ctgagctggc   6600
ctctcactgc ctccccaagg ccccctgcct gccctgtcag gaggcagaag gaagcaggtg   6660
tgagggcagt gcaaggaggg agcacaaccc ccagctcccg ctccgggctc cgacttgtgc   6720
acaggcagag cccagaccct ggaggaaatc ctacctttga attcaagaac atttggggaa   6780
tttggaaatc tctttgcccc caaacccccca ttctgtccta cctttaatca ggtcctgctc   6840
agcagtgaga gcagatgagg tgaaaaggcc aagaggtttg gctcctgccc actgatagcc   6900
cctctccccg cagtgtttgt gtgtcaagtg gcaaagctgt tcttcctggt gaccctgatt   6960
atatccagta acacatagac tgtgcgcata ggcctgcttt gtctcctcta tcctgggctt   7020
ttgttttgct ttttagtttt gcttttagtt tttctgtccc ttttatttaa cgcaccgact   7080
agacacacaa agcagttgaa tttttatata tatatctgta tattgcacaa ttataaactc   7140
attttgcttg tggctccaca cacacaaaaa aagacctgtt aaaattatac ctgttgctta   7200
attacaatat ttctgataac catagcatag gacaagggaa aataaaaaaa gaaaaaaaag   7260
aaaaaaaaac gacaaatctg tctgctggtc acttcttctg tccaagcaga ttcgtggtct   7320
tttcctcgct tctttcaagg gctttcctgt gccaggtgaa ggaggctcca ggcagcaccc   7380
```

```
aggttttgca ctcttgtttc tcccgtgctt gtgaaagagg tcccaaggtt ctgggtgcag   7440
gagcgctccc ttgacctgct gaagtccgga acgtagtcgg cacagcctgg tcgccttcca   7500
cctctgggag ctggagtcca ctggggtggc ctgactcccc cagtcccctt cccgtgacct   7560
ggtcagggtg agcccatgtg gagtcagcct cgcaggcctc cctgccagta gggtccgagt   7620
gtgtttcatc cttcccactc tgtcgagcct gggggctgga gcggagacgg gaggcctggc   7680
ctgtctcgga acctgtgagc tgcaccaggt agaacgccag ggaccccaga atcatgtgcg   7740
tcagtccaag ggtcccctc caggagtagt gaagactcca gaaatgtccc tttcttctcc   7800
cccatcctac gagtaattgc atttgctttt gtaattctta atgagcaata tctgctagag   7860
agtttagctg taacagttct tttgatcat cttttttaa taattagaaa caccaaaaaa   7920
atccagaaac ttgttcttcc aaagcagaga gcattataat caccagggcc aaaagcttcc   7980
ctccctgctg tcattgcttc ttctgaggcc tgaatccaaa agaaaaacag ccataggccc   8040
tttcagtggc cgggctaccc gtgagccctt cggaggacca gggctggggc agcctctggg   8100
cccacatccg gggccagctc cggcgtgtgt tcagtgttag cagtgggtca tgatgctctt   8160
tcccacccag cctgggatag gggcagagga ggcgaggagg ccgttgccgc tgatgtttgg   8220
ccgtgaacag gtgggtgtct gcgtgcgtcc acgtgcgtgt tttctgactg acatgaaatc   8280
gacgcccgag ttagcctcac ccggtgacct ctagccctgc ccggatggag cggggcccac   8340
ccggttcagt gtttctgggg agctggacag tggagtgcaa aaggcttgca gaacttgaag   8400
cctgctcctt cccttgctac cacggcctcc tttccgtttg atttgtcact gcttcaatca   8460
ataacagccg ctccagagtc agtagtcaat gaatatatga ccaaatatca ccaggactgt   8520
tactcaatgt gtgccgagcc cttgcccatg ctgggctccc gtgtatctgg acactgtaac   8580
gtgtgctgtg tttgctcccc ttccccttcc ttctttgccc tttacttgtc tttctggggt   8640
ttttctgttt gggtttggtt tggtttttat ttctcctttt gtgttccaaa catgaggttc   8700
tctctactgg tcctcttaac tgtggtgttg aggcttatat ttgtgtaatt tttggtgggt   8760
gaaaggaatt ttgctaagta aatctcttct gtgtttgaac tgaagtctgt attgtaacta   8820
tgtttaaagt aattgttcca gagacaaata tttctagaca ctttttcttt acaaacaaaa   8880
gcattcggag ggagggggat ggtgactgag atgagagggg agagctgaac agatgacccc   8940
tgcccagatc agccagaagc cacccaaagc agtggagccc aggagtccca ctccaagcca   9000
gcaagccgaa tagctgatgt gttgccactt tccaagtcac tgcaaaacca ggttttgttc   9060
cgcccagtgg attcttgttt tgcttcccct ccccccgaga ttattaccac catcccgtgc   9120
ttttaaggaa aggcaagatt gatgtttcct tgaggggagc caggagggga tgtgtgtgtg   9180
cagagctgaa gagctgggga gaatggggct gggcccaccc aagcaggagg ctgggacgct   9240
ctgctgtggg cacaggtcag gctaatgttg gcagatgcag ctcttcctgg acaggccagg   9300
tggtgggcat tctctctcca aggtgtgccc cgtgggcatt actgtttaag acacttccgt   9360
cacatcccac cccatcctcc agggctcaac actgtgacat ctctattccc caccctcccc   9420
ttcccagggc aataaaatga ccatggaggg ggcttgcact ctcttggctg tcacccgatc   9480
gccagcaaaa cttagatgtg agaaaacccc ttcccattcc atggcgaaaa catctcctta   9540
gaaaagccat taccctcatt aggcatggtt ttgggctccc aaaacacctg acagcccctc   9600
cctcctctga gaggcggaga gtgctgactg tagtgaccat tgcatgccgg gtgcagcatc   9660
tggaagagct aggcagggtg tctgcccccct cctgagttga agtcatgctc ccctgtgcca   9720
gcccagaggc cgagagctat ggacagcatt gccagtaaca caggccaccc tgtgcagaag   9780
```

```
ggagctggct ccagcctgga aacctgtctg aggttgggag aggtgcactt ggggcacagg   9840

gagaggccgg gacacactta gctggagatg tctctaaaag ccctgtatcg tattcacctt   9900

cagtttttgt gttttgggac aattacttta gaaaataagt aggtcgtttt aaaaacaaaa   9960

attattgatt gctttttttgt agtgttcaga aaaaaggttc tttgtgtata gccaaatgac  10020

tgaaagcact gatatattta aaaacaaaag gcaatttatt aaggaaattt gtaccatttc  10080

agtaaacctg tctgaatgta cctgtatacg tttcaaaaac accccccccc cactgaatcc  10140

ctgtaaccta tttattatat aaagagtttg ccttataaat tt                      10182
```

<210> SEQ ID NO 24
<211> LENGTH: 10180
<212> TYPE: DNA
<213> ORGANISM: Homo sapiens

<400> SEQUENCE: 24

```
ccggaaaatg gccgccgccg ccgccgccgc gccgagcgga ggaggaggag gaggcgagga     60

ggagagacct ccataaaaat acagactcac cagttcctgc tttgatgtga catgtgactc    120

cccagaatac accttgcttc tgtagaccag ctccaacagg attccatggt agctgggatg    180

ttagggctca gggaagaaaa gtcagaagac caggacctcc agggcctcaa ggacaaaccc    240

ctcaagttta aaaaggtgaa gaaagataag aaagaagaga aagagggcaa gcatgagccc    300

gtgcagccat cagcccacca ctctgctgag cccgcagagg caggcaaagc agagacatca    360

gaagggtcag gctccgcccc ggctgtgccg gaagcttctg cctcccccaa acagcggcgc    420

tccatcatcc gtgaccgggg acccatgtat gatgacccca ccctgcctga aggctggaca    480

cggaagctta agcaaaggaa atctggccgc tctgctggga agtatgatgt gtatttgatc    540

aatccccagg gaaaagcctt tcgctctaaa gtggagttga ttgcgtactt cgaaaaggta    600

ggcgacacat ccctggaccc taatgatttt gacttcacgg taactgggag agggagcccc    660

tcccggcgag agcagaaacc acctaagaag cccaaatctc ccaaagctcc aggaactggc    720

agaggccggg gacgccccaa agggagcggc accacgagac ccaaggcggc cacgtcagag    780

ggtgtgcagg tgaaaagggt cctggagaaa agtcctggga agctccttgt caagatgcct    840

tttcaaactt cgccaggggg caaggctgag gggggtgggg ccaccacatc cacccaggtc    900

atggtgatca aacgccccgg caggaagcga aaagctgagg ccgaccctca ggccattccc    960

aagaaacggg gccgaaagcc ggggagtgtg gtggcagccg ctgccgccga ggccaaaaag   1020

aaagccgtga aggagtcttc tatccgatct gtgcaggaga ccgtactccc catcaagaag   1080

cgcaagaccc gggagacggt cagcatcgag gtcaaggaag tggtgaagcc cctgctggtg   1140

tccaccctcg gtgagaagag cgggaaagga ctgaagacct gtaagagccc tgggcggaaa   1200

agcaaggaga gcagccccaa ggggcgcagc agcagcgcct cctcaccccc caagaaggag   1260

caccaccacc atcaccacca ctcagagtcc ccaaaggccc ccgtgccact gctcccaccc   1320

ctgcccccac ctccacctga gcccgagagc tccgaggacc ccaccagccc ccctgagccc   1380

caggacttga gcagcagcgt ctgcaaagag gagaagatgc ccagaggagg ctcactggag   1440

agcgacggct gccccaagga gccagctaag actcagcccg cggttgccac cgccgccacg   1500

gccgcagaaa agtacaaaca ccgaggggag ggagagcgca aagacattgt ttcatcctcc   1560

atgccaaggc caaacagaga ggagcctgtg gacagccgga cgcccgtgac cgagagagtt   1620

agctgacttt acacggagcg gattgcaaag caaaccaaca agaataaagg cagctgttgt   1680

ctcttctcct tatgggtagg gctctgacaa agcttcccga ttaactgaaa taaaaaatat   1740
```

```
ttttttttct ttcagtaaac ttagagtttc gtggcttcag ggtgggagta gttggagcat   1800
tggggatgtt tttcttaccg acaagcacag tcaggttgaa gacctaacca gggccagaag   1860
tagctttgca cttttctaaa ctaggctcct tcaacaaggc ttgctgcaga tactactgac   1920
cagacaagct gttgaccagg cacctcccct cccgcccaaa cctttccccc atgtggtcgt   1980
tagagacaga gcgacagagc agttgagagg acactcccgt tttcggtgcc atcagtgccc   2040
cgtctacagc tcccccagct ccccccacct cccccactcc caaccacgtt gggacaggga   2100
ggtgtgaggc aggagagaca gttggattct ttagagaaga tggatatgac cagtggctat   2160
ggcctgtgcg atcccacccg tggtggctca agtctggccc cacaccagcc ccaatccaaa   2220
actggcaagg acgcttcaca ggacaggaaa gtggcacctg tctgctccag ctctggcatg   2280
gctaggaggg gggagtccct tgaactactg ggtgtagact ggcctgaacc acaggagagg   2340
atggcccagg gtgaggtggc atggtccatt ctcaagggac gtcctccaac gggtggcgct   2400
agaggccatg gaggcagtag gacaaggtgc aggcaggctg gcctggggtc aggccgggca   2460
gagcacagcg gggtgagagg gattcctaat cactcagagc agtctgtgac ttagtggaca   2520
ggggaggggg caaaggggga ggagaagaaa atgttcttcc agttactttc caattctcct   2580
ttagggacag cttagaatta tttgcactat tgagtcttca tgttcccact tcaaaacaaa   2640
cagatgctct gagagcaaac tggcttgaat tggtgacatt tagtccctca agccaccaga   2700
tgtgacagtg ttgagaacta cctggatttg tatatatacc tgcgcttgtt ttaaagtggg   2760
ctcagcacat agggttccca cgaagctccg aaactctaag tgtttgctgc aattttataa   2820
ggacttcctg attggtttct cttctcccct tccatttctg ccttttgttc atttcatcct   2880
ttcacttctt tcccttcctc cgtcctcctc cttcctagtt catcccttct cttccaggca   2940
gccgcggtgc ccaaccacac ttgtcggctc cagtccccag aactctgcct gccctttgtc   3000
ctcctgctgc cagtaccagc cccaccctgt tttgagccct gaggaggcct tgggctctgc   3060
tgagtccgac ctggcctgtc tgtgaagagc aagagagcag caaggtcttg ctctcctagg   3120
tagccccctc ttccctggta agaaaaagca aaaggcattt cccaccctga acaacgagcc   3180
ttttcaccct tctactctag agaagtggac tggaggagct gggcccgatt tggtagttga   3240
ggaaagcaca gaggcctcct gtggcctgcc agtcatcgag tggcccaaca ggggctccat   3300
gccagccgac cttgacctca ctcagaagtc cagagtctag cgtagtgcag cagggcagta   3360
gcggtaccaa tgcagaactc ccaagacccg agctgggacc agtacctggg tccccagccc   3420
ttcctctgct ccccctttc cctcggagtt cttcttgaat ggcaatgttt tgcttttgct   3480
cgatgcagac agggggccag aacaccacac atttcactgt ctgtctggtc catagctgtg   3540
gtgtaggggc ttagaggcat gggcttgctg tgggttttta attgatcagt tttcatgtgg   3600
gatcccatct ttttaacctc tgttcaggaa gtccttatct agctgcatat cttcatcata   3660
ttggtatatc cttttctgtg tttacagaga tgtctcttat atctaaatct gtccaactga   3720
gaagtacctt atcaaagtag caaatgagac agcagtctta tgcttccaga aacacccaca   3780
ggcatgtccc atgtgagctg ctgccatgaa ctgtcaagtg tgtgttgtct tgtgtatttc   3840
agttattgtc cctggcttcc ttactatggt gtaatcatga aggagtgaaa catcatagaa   3900
actgtctagc acttccttgc cagtctttag tgatcaggaa ccatagttga cagttccaat   3960
cagtagctta agaaaaaacc gtgtttgtct cttctggaat ggttagaagt gagggagttt   4020
gccccgttct gtttgtagag tctcatagtt ggactttcta gcatatatgt gtccatttcc   4080
ttatgctgta aaagcaagtc ctgcaaccaa actcccatca gcccaatccc tgatccctga   4140
```

```
tcccttccac ctgctctgct gatgaccccc ccagcttcac ttctgactct tccccaggaa   4200

gggaaggggg gtcagaagag agggtgagtc ctccagaact cttcctccaa ggacagaagg   4260

ctcctgcccc catagtggcc tcgaactcct ggcactacca aaggacactt atccacgaga   4320

gcgcagcatc cgaccaggtt gtcactgaga agatgtttat tttggtcagt tgggttttta   4380

tgtattatac ttagtcaaat gtaatgtggc ttctggaatc attgtccaga gctgcttccc   4440

cgtcacctgg gcgtcatctg gtcctggtaa gaggagtgcg tggcccacca ggccccccctg   4500

tcacccatga cagttcattc agggccgatg gggcagtcgt ggttgggaac acagcatttc   4560

aagcgtcact ttatttcatt cgggccccac ctgcagctcc ctcaaagagg cagttgccca   4620

gcctctttcc cttccagttt attccagagc tgccagtggg gcctgaggct ccttagggtt   4680

ttctctctat ttcccccttt cttcctcatt ccctcgtctt tcccaaaggc atcacgagtc   4740

agtcgccttt cagcaggcag ccttggcggt ttatcgccct ggcaggcagg ggccctgcag   4800

ctctcatgct gcccctgcct tggggtcagg ttgacaggag gttggaggga aagccttaag   4860

ctgcaggatt ctcaccagct gtgtccggcc cagttttggg gtgtgacctc aatttcaatt   4920

ttgtctgtac ttgaacatta tgaagatggg ggcctctttc agtgaatttg tgaacagcag   4980

aattgaccga cagctttcca gtacccatgg ggctaggtca ttaaggccac atccacagtc   5040

tcccccaccc ttgttccagt tgttagttac tacctcctct cctgacaata ctgtatgtcg   5100

tcgagctccc cccaggtcta cccctcccgg ccctgcctgc tggtgggctt gtcatagcca   5160

gtgggattgc cggtcttgac agctcagtga gctggagata cttggtcaca gccaggcgct   5220

agcacagctc ccttctgttg atgctgtatt cccatatcaa aagacacagg ggacacccag   5280

aaacgccaca tcccccaatc catcagtgcc aaactagcca acggccccag cttctcagct   5340

cgctggatgg cggaagctgc tactcgtgag cgccagtgcg ggtgcagaca atcttctgtt   5400

gggtggcatc attccaggcc cgaagcatga acagtgcacc tgggacaggg agcagcccca   5460

aattgtcacc tgcttctctg cccagctttt cattgctgtg acagtgatgg cgaaagaggg   5520

taataaccag acacaaactg ccaagttggg tggagaaagg agtttcttta gctgacagaa   5580

tctctgaatt ttaaatcact tagtaagcgg ctcaagccca ggagggagca gagggatacg   5640

agcggagtcc cctgcgcggg accatctgga attggtttag cccaagtgga gcctgacagc   5700

cagaactctg tgtcccccgt ctaaccacag ctccttttcc agagcattcc agtcaggctc   5760

tctgggctga ctgggccagg ggaggttaca ggtaccagtt ctttaagaag atctttgggc   5820

atatacattt ttagcctgtg tcattgcccc aaatggattc ctgtttcaag ttcacacctg   5880

cagattctag gacctgtgtc ctagacttca gggagtcagc tgtttctaga gttcctacca   5940

tggagtgggt ctggaggacc tgcccggtgg gggggcagag ccctgctccc tccgggtctt   6000

cctactcttc tctctgctct gacgggattt gttgattctc tccattttgg tgtctttctc   6060

ttttagatat tgtatcaatc tttagaaaag gcatagtcta cttgttataa atcgttagga   6120

tactgcctcc cccagggtct aaaattacat attagagggg aaaagctgaa cactgaagtc   6180

agttctcaac aatttagaag gaaaacctag aaaacatttg gcagaaaatt acatttcgat   6240

gtttttgaat gaatacgagc aagcttttac aacagtgctg atctaaaaat acttagcact   6300

tggcctgaga tgcctggtga gcattacagg caaggggaat ctggaggtag ccgacctgag   6360

gacatggctt ctgaacctgt cttttgggag tggtatggaa ggtggagcgt tcaccagtga   6420

cctggaaggc ccagcaccac cctccttccc actcttctca tcttgacaga gcctgcccca   6480

gcgctgacgt gtcaggaaaa cacccaggga actaggaagg cacttctgcc tgaggggcag   6540
```

-continued

```
cctgccttgc ccactcctgc tctgctcgcc tcggatcagc tgagccttct gagctggcct   6600

ctcactgcct ccccaaggcc ccctgcctgc cctgtcagga ggcagaagga agcaggtgtg   6660

agggcagtgc aaggagggag cacaaccccc agctcccgct ccgggctccg acttgtgcac   6720

aggcagagcc cagaccctgg aggaaatcct acctttgaat tcaagaacat ttggggaatt   6780

tggaaatctc tttgccccca aacccccatt ctgtcctacc tttaatcagg tcctgctcag   6840

cagtgagagc agatgaggtg aaaaggccaa gaggtttggc tcctgcccac tgatagcccc   6900

tctccccgca gtgtttgtgt gtcaagtggc aaagctgttc ttcctggtga ccctgattat   6960

atccagtaac acatagactg tgcgcatagg cctgctttgt ctcctctatc ctgggctttt   7020

gttttgcttt ttagttttgc ttttagtttt tctgtccctt ttatttaacg caccgactag   7080

acacacaaag cagttgaatt tttatatata tatctgtata ttgcacaatt ataaactcat   7140

tttgcttgtg gctccacaca cacaaaaaaa gacctgttaa aattatacct gttgcttaat   7200

tacaatattt ctgataacca tagcatagga caagggaaaa taaaaaaaga aaaaaaagaa   7260

aaaaaaacga caaatctgtc tgctggtcac ttcttctgtc caagcagatt cgtggtcttt   7320

tcctcgcttc tttcaagggc tttcctgtgc caggtgaagg aggctccagg cagcacccag   7380

gttttgcact cttgtttctc ccgtgcttgt gaaagaggtc ccaaggttct gggtgcagga   7440

gcgctccctt gacctgctga agtccggaac gtagtcggca cagcctggtc gccttccacc   7500

tctgggagct ggagtccact ggggtggcct gactccccca gtccccttcc cgtgacctgg   7560

tcagggtgag cccatgtgga gtcagcctcg caggcctccc tgccagtagg gtccgagtgt   7620

gtttcatcct tcccactctg tcgagcctgg gggctggagc ggagacggga ggcctggcct   7680

gtctcggaac ctgtgagctg caccaggtag aacgccaggg accccagaat catgtgcgtc   7740

agtccaaggg gtcccctcca ggagtagtga agactccaga aatgtccctt tcttctcccc   7800

catcctacga gtaattgcat ttgcttttgt aattcttaat gagcaatatc tgctagagag   7860

tttagctgta acagttcttt ttgatcatct ttttttaata attagaaaca ccaaaaaaat   7920

ccagaaactt gttcttccaa agcagagagc attataatca ccagggccaa aagcttccct   7980

ccctgctgtc attgcttctt ctgaggcctg aatccaaaag aaaaacagcc ataggccctt   8040

tcagtggccg ggctacccgt gagcccttcg gaggaccagg gctggggcag cctctgggcc   8100

cacatccggg gccagctccg gcgtgtgttc agtgttagca gtgggtcatg atgctctttc   8160

ccacccagcc tgggataggg gcagaggagg cgaggaggcc gttgccgctg atgtttggcc   8220

gtgaacaggt gggtgtctgc gtgcgtccac gtgcgtgttt tctgactgac atgaaatcga   8280

cgcccgagtt agcctcaccc ggtgacctct agccctgccc ggatggagcg gggcccaccc   8340

ggttcagtgt ttctggggag ctggacagtg gagtgcaaaa ggcttgcaga acttgaagcc   8400

tgctccttcc cttgctacca cggcctcctt tccgtttgat ttgtcactgc ttcaatcaat   8460

aacagccgct ccagagtcag tagtcaatga atatatgacc aaatatcacc aggactgtta   8520

ctcaatgtgt gccgagccct tgcccatgct gggctcccgt gtatctggac actgtaacgt   8580

gtgctgtgtt tgctcccctt ccccttcctt ctttgccctt tacttgtctt tctggggttt   8640

ttctgtttgg gtttggtttg gtttttattt ctccttttgt gttccaaaca tgaggttctc   8700

tctactggtc ctcttaactg tggtgttgag gcttatattt gtgtaatttt tggtgggtga   8760

aaggaatttt gctaagtaaa tctcttctgt gtttgaactg aagtctgtat tgtaactatg   8820

tttaaagtaa ttgttccaga gacaaatatt tctagacact ttttctttac aaacaaaagc   8880

attcggaggg agggggatgg tgactgagat gagaggggag agctgaacag atgacccctg   8940
```

```
cccagatcag ccagaagcca cccaaagcag tggagcccag gagtcccact ccaagccagc   9000
aagccgaata gctgatgtgt tgccactttc caagtcactg caaaaccagg ttttgttccg   9060
cccagtggat tcttgttttg cttcccctcc ccccgagatt attaccacca tcccgtgctt   9120
ttaaggaaag gcaagattga tgtttccttg aggggagcca ggaggggatg tgtgtgtgca   9180
gagctgaaga gctggggaga atggggctgg gcccacccaa gcaggaggct gggacgctct   9240
gctgtgggca caggtcaggc taatgttggc agatgcagct cttcctggac aggccaggtg   9300
gtgggcattc tctctccaag gtgtgccccg tgggcattac tgtttaagac acttccgtca   9360
catcccaccc catcctccag ggctcaacac tgtgacatct ctattcccca ccctcccctt   9420
cccagggcaa taaaatgacc atggaggggg cttgcactct cttggctgtc acccgatcgc   9480
cagcaaaact tagatgtgag aaaacccctt cccattccat ggcgaaaaca tctccttaga   9540
aaagccatta ccctcattag gcatggtttt gggctcccaa aacacctgac agcccctccc   9600
tcctctgaga ggcggagagt gctgactgta gtgaccattg catgccgggt gcagcatctg   9660
gaagagctag gcagggtgtc tgccccctcc tgagttgaag tcatgctccc ctgtgccagc   9720
ccagaggccg agagctatgg acagcattgc cagtaacaca ggccaccctg tgcagaaggg   9780
agctggctcc agcctggaaa cctgtctgag gttgggagag gtgcacttgg ggcacaggga   9840
gaggccggga cacacttagc tggagatgtc tctaaaagcc ctgtatcgta ttcaccttca   9900
gtttttgtgt tttgggacaa ttactttaga aaataagtag gtcgttttaa aaacaaaaat   9960
tattgattgc ttttttgtag tgttcagaaa aaaggttctt tgtgtatagc caaatgactg  10020
aaagcactga tatatttaaa aacaaaaggc aatttattaa ggaaatttgt accatttcag  10080
taaacctgtc tgaatgtacc tgtatacgtt tcaaaaacac cccccccca ctgaatccct  10140
gtaacctatt tattatataa agagtttgcc ttataaattt                       10180
```

<210> SEQ ID NO 25
<211> LENGTH: 10191
<212> TYPE: DNA
<213> ORGANISM: Homo sapiens

<400> SEQUENCE: 25

```
ccggaaaatg gccgccgccg ccgccgccgc cgccgccgcg ccgagcggag gaggaggagg     60
aggcgaggag gagagactgc tccataaaaa tacagactca ccagttcctg ctttgatgtg    120
acatgtgact ccccagaata caccttgctt ctgtagacca gctccaacag gattccatgg    180
tagctgggat gttagggctc agggaagaaa agtcagaaga ccaggacctc cagggcctca    240
aggacaaacc cctcaagttt aaaaaggtga agaaagataa gaaagaagag aaagagggca    300
agcatgagcc cgtgcagcca tcagcccacc actctgctga gcccgcagag gcaggcaaag    360
cagagacatc agaagggtca ggctccgccc cggctgtgcc ggaagcttct gcctccccca    420
aacagcggcg ctccatcatc cgtgaccggg gacccatgta tgatgacccc accctgcctg    480
aaggctggac acggaagctt aagcaaagga aatctggccg ctctgctggg aagtatgatg    540
tgtatttgat caatccccag ggaaaagcct ttcgctctaa agtggagttg attgcgtact    600
tcgaaaaggt aggcgacaca tccctggacc ctaatgattt tgacttcacg gtaactggga    660
gagggagccc ctcccggcga gagcagaaac cacctaagaa gcccaaatct cccaaagctc    720
caggaactgg cagaggccgg ggacgcccca aagggagcgg caccacgaga cccaaggcgg    780
ccacgtcaga gggtgtgcag gtgaaaaggg tcctggagaa aagtcctggg aagctccttg    840
tcaagatgcc ttttcaaact tcgccagggg gcaaggctga ggggggtggg gccaccacat    900
```

-continued

```
ccacccaggt catggtgatc aaacgccccg gcaggaagcg aaaagctgag gccgaccctc    960
aggccattcc caagaaacgg ggccgaaagc cggggagtgt ggtggcagcc gctgccgccg   1020
aggccaaaaa gaaagccgtg aaggagtctt ctatccgatc tgtgcaggag accgtactcc   1080
ccatcaagaa gcgcaagacc cgggagacgg tcagcatcga ggtcaaggaa gtggtgaagc   1140
ccctgctggt gtccaccctc ggtgagaaga gcgggaaagg actgaagacc tgtaagagcc   1200
ctgggcggaa aagcaaggag agcagcccca aggggcgcag cagcagcgcc tcctcacccc   1260
ccaagaagga gcaccaccac catcaccacc actcagagtc ccccaaggcc cccgtgccac   1320
tgctcccacc cctgccccca cctccacctg agcccgagag ctccgaggac cccaccagcc   1380
cccctgagcc ccaggacttg agcagcagcg tctgcaaaga ggagaagatg cccagaggag   1440
gctcactgga gagcgacggc tgccccaagg agccagctaa gactcagccc gcggttgcca   1500
ccgccgccac ggccgcagaa aagtacaaac accgagggga gggagagcgc aaagacattg   1560
tttcatcctc catgccaagg ccaaacagag aggagcctgt ggacagccgg acgcccgtga   1620
ccgagagagt tagctgactt tacacggagc ggattgcaaa gcaaaccaac aagaataaag   1680
gcagctgttg tctcttctcc ttatgggtag ggctctgaca aagcttcccg attaactgaa   1740
ataaaaaata tttttttttc tttcagtaaa cttagagttt cgtggcttca gggtgggagt   1800
agttggagca ttggggatgt ttttcttacc gacaagcaca gtcaggttga agacctaacc   1860
agggccagaa gtagctttgc acttttctaa actaggctcc ttcaacaagg cttgctgcag   1920
atactactga ccagacaagc tgttgaccag gcacctcccc tcccgcccaa acctttcccc   1980
catgtggtcg ttagagacag agcgacagag cagttgagag gacactcccg ttttcggtgc   2040
catcagtgcc ccgtctacag ctcccccagc tccccccacc tcccccactc ccaaccacgt   2100
tgggacaggg aggtgtgagg caggagagac agttggattc tttagagaag atggatatga   2160
ccagtggcta tggcctgtgc gatcccaccc gtggtggctc aagtctggcc ccacaccagc   2220
cccaatccaa aactggcaag gacgcttcac aggacaggaa agtggcacct gtctgctcca   2280
gctctggcat ggctaggagg ggggagtccc ttgaactact gggtgtagac tggcctgaac   2340
cacaggagag gatggcccag ggtgaggtgg catggtccat tctcaaggga cgtcctccaa   2400
cgggtggcgc tagaggccat ggaggcagta ggacaaggtg caggcaggct ggcctggggt   2460
caggccgggc agagcacagc ggggtgagag ggattcctaa tcactcagag cagtctgtga   2520
cttagtggac aggggagggg gcaaaggggg aggagaagaa aatgttcttc cagttacttt   2580
ccaattctcc tttagggaca gcttagaatt atttgcacta ttgagtcttc atgttcccac   2640
ttcaaaacaa acagatgctc tgagagcaaa ctggcttgaa ttggtgacat ttagtccctc   2700
aagccaccag atgtgacagt gttgagaact acctggattt gtatatatac ctgcgcttgt   2760
tttaaagtgg gctcagcaca tagggttccc acgaagctcc gaaactctaa gtgtttgctg   2820
caattttata aggacttcct gattggtttc tcttctcccc ttccatttct gccttttgtt   2880
catttcatcc tttcacttct ttcccttcct ccgtcctcct ccttcctagt tcatcccttc   2940
tcttccaggc agccgcggtg cccaaccaca cttgtcggct ccagtcccca gaactctgcc   3000
tgccctttgt cctcctgctg ccagtaccag ccccaccctg ttttgagccc tgaggaggcc   3060
ttgggctctg ctgagtccga cctggcctgt ctgtgaagag caagagagca gcaaggtctt   3120
gctctcctag gtagcccccct cttccctggt aagaaaaagc aaaaggcatt tcccaccctg   3180
aacaacgagc cttttcaccc ttctactcta gagaagtgga ctggaggagc tgggcccgat   3240
ttggtagttg aggaaagcac agaggcctcc tgtggcctgc cagtcatcga gtggcccaac   3300
```

```
aggggctcca tgccagccga ccttgacctc actcagaagt ccagagtcta gcgtagtgca   3360

gcagggcagt agcggtacca atgcagaact cccaagaccc gagctgggac cagtacctgg   3420

gtccccagcc cttcctctgc tccccctttt ccctcggagt tcttcttgaa tggcaatgtt   3480

ttgcttttgc tcgatgcaga cagggggcca gaacaccaca catttcactg tctgtctggt   3540

ccatagctgt ggtgtagggg cttagaggca tgggcttgct gtgggttttt aattgatcag   3600

ttttcatgtg ggatcccatc tttttaacct ctgttcagga agtccttatc tagctgcata   3660

tcttcatcat attggtatat ccttttctgt gtttacagag atgtctctta tatctaaatc   3720

tgtccaactg agaagtacct tatcaaagta gcaaatgaga cagcagtctt atgcttccag   3780

aaacacccac aggcatgtcc catgtgagct gctgccatga actgtcaagt gtgtgttgtc   3840

ttgtgtattt cagttattgt ccctggcttc cttactatgg tgtaatcatg aaggagtgaa   3900

acatcataga aactgtctag cacttccttg ccagtcttta gtgatcagga accatagttg   3960

acagttccaa tcagtagctt aagaaaaaac cgtgtttgtc tcttctggaa tggttagaag   4020

tgagggagtt tgccccgttc tgtttgtaga gtctcatagt tggactttct agcatatatg   4080

tgtccatttc cttatgctgt aaaagcaagt cctgcaacca aactcccatc agcccaatcc   4140

ctgatccctg atcccttcca cctgctctgc tgatgacccc cccagcttca cttctgactc   4200

ttccccagga agggaagggg ggtcagaaga gagggtgagt cctccagaac tcttcctcca   4260

aggacagaag gctcctgccc ccatagtggc ctcgaactcc tggcactacc aaaggacact   4320

tatccacgag agcgcagcat ccgaccaggt tgtcactgag aagatgttta ttttggtcag   4380

ttgggttttt atgtattata cttagtcaaa tgtaatgtgg cttctggaat cattgtccag   4440

agctgcttcc ccgtcacctg ggcgtcatct ggtcctggta agaggagtgc gtggcccacc   4500

aggccccccct gtcacccatg acagttcatt cagggccgat ggggcagtcg tggttgggaa   4560

cacagcattt caagcgtcac tttatttcat tcgggcccca cctgcagctc cctcaaagag   4620

gcagttgccc agcctctttc ccttccagtt tattccagag ctgccagtgg ggcctgaggc   4680

tccttagggt tttctctcta tttccccctt tcttcctcat tccctcgtct ttcccaaagg   4740

catcacgagt cagtcgcctt tcagcaggca gccttggcgg tttatcgccc tggcaggcag   4800

gggccctgca gctctcatgc tgcccctgcc ttggggtcag gttgacagga ggttggaggg   4860

aaagccttaa gctgcaggat tctcaccagc tgtgtccggc ccagttttgg ggtgtgacct   4920

caatttcaat tttgtctgta cttgaacatt atgaagatgg gggcctcttt cagtgaattt   4980

gtgaacagca gaattgaccg acagctttcc agtacccatg gggctaggtc attaaggcca   5040

catccacagt ctcccccacc cttgttccag ttgttagtta ctacctcctc tcctgacaat   5100

actgtatgtc gtcgagctcc ccccaggtct accccctcccg gccctgcctg ctggtgggct   5160

tgtcatagcc agtgggattg ccggtcttga cagctcagtg agctggagat acttggtcac   5220

agccaggcgc tagcacagct cccttctgtt gatgctgtat tcccatatca aaagacacag   5280

gggacaccca gaaacgccac atcccccaat ccatcagtgc caaactagcc aacggcccca   5340

gcttctcagc tcgctggatg gcggaagctg ctactcgtga gcgccagtgc gggtgcagac   5400

aatcttctgt tgggtggcat cattccaggc ccgaagcatg aacagtgcac ctgggacagg   5460

gagcagcccc aaattgtcac ctgcttctct gcccagcttt tcattgctgt gacagtgatg   5520

gcgaaagagg gtaataacca gacacaaact gccaagttgg gtggagaaag gagtttcttt   5580

agctgacaga atctctgaat tttaaatcac ttagtaagcg gctcaagccc aggagggagc   5640

agagggatac gagcggagtc ccctgcgcgg gaccatctgg aattggttta gcccaagtgg   5700
```

```
agcctgacag ccagaactct gtgtcccccg tctaaccaca gctccttttc cagagcattc   5760
cagtcaggct ctctgggctg actgggccag gggaggttac aggtaccagt tctttaagaa   5820
gatctttggg catatacatt tttagcctgt gtcattgccc caaatggatt cctgtttcaa   5880
gttcacacct gcagattcta ggacctgtgt cctagacttc agggagtcag ctgtttctag   5940
agttcctacc atggagtggg tctggaggac ctgcccggtg gggggcaga gccctgctcc   6000
ctccgggtct tcctactctt ctctctgctc tgacgggatt tgttgattct ctccattttg   6060
gtgtctttct cttttagata ttgtatcaat ctttagaaaa ggcatagtct acttgttata   6120
aatcgttagg atactgcctc ccccagggtc taaaattaca tattagaggg gaaaagctga   6180
acactgaagt cagttctcaa caatttagaa ggaaaaccta gaaaacattt ggcagaaaat   6240
tacatttcga tgtttttgaa tgaatacgag caagctttta caacagtgct gatctaaaaa   6300
tacttagcac ttggcctgag atgcctggtg agcattacag gcaaggggaa tctggaggta   6360
gccgacctga ggacatggct tctgaacctg tcttttggga gtggtatgga aggtggagcg   6420
ttcaccagtg acctggaagg cccagcacca ccctccttcc cactcttctc atcttgacag   6480
agcctgcccc agcgctgacg tgtcaggaaa acacccaggg aactaggaag gcacttctgc   6540
ctgaggggca gcctgccttg cccactcctg ctctgctcgc ctcggatcag ctgagccttc   6600
tgagctggcc tctcactgcc tccccaaggc cccctgcctg ccctgtcagg aggcagaagg   6660
aagcaggtgt gagggcagtg caaggaggga gcacaacccc cagctcccgc tccgggctcc   6720
gacttgtgca caggcagagc ccagaccctg gaggaaatcc tacctttgaa ttcaagaaca   6780
tttggggaat ttggaaatct ctttgccccc aaaccccat tctgtcctac ctttaatcag   6840
gtcctgctca gcagtgagag cagatgaggt gaaaaggcca agaggtttgg ctcctgccca   6900
ctgatagccc ctctccccgc agtgtttgtg tgtcaagtgg caaagctgtt cttcctggtg   6960
accctgatta tatccagtaa cacatagact gtgcgcatag gcctgctttg tctcctctat   7020
cctgggcttt tgttttgctt tttagttttg cttttagttt ttctgtccct tttatttaac   7080
gcaccgacta gacacacaaa gcagttgaat ttttatatat atatctgtat attgcacaat   7140
tataaactca ttttgcttgt ggctccacac acacaaaaaa agacctgtta aaattatacc   7200
tgttgcttaa ttacaatatt tctgataacc atagcatagg acaagggaaa ataaaaaaag   7260
aaaaaaaaga aaaaaaaacg acaaatctgt ctgctggtca cttcttctgt ccaagcagat   7320
tcgtggtctt ttcctcgctt ctttcaaggg ctttcctgtg ccaggtgaag gaggctccag   7380
gcagcaccca ggttttgcac tcttgtttct cccgtgcttg tgaaagaggt cccaaggttc   7440
tgggtgcagg agcgctccct tgacctgctg aagtccggaa cgtagtcggc acagcctggt   7500
cgccttccac ctctgggagc tggagtccac tggggtggcc tgactccccc agtccccttc   7560
ccgtgacctg gtcagggtga gcccatgtgg agtcagcctc gcaggcctcc ctgccagtag   7620
ggtccgagtg tgtttcatcc ttcccactct gtcgagcctg gggctggag cggagacggg   7680
aggcctggcc tgtctcggaa cctgtgagct gcaccaggta gaacgccagg gaccccagaa   7740
tcatgtgcgt cagtccaagg ggtcccctcc aggagtagtg aagactccag aaatgtccct   7800
ttcttctccc ccatcctacg agtaattgca tttgcttttg taattcttaa tgagcaatat   7860
ctgctagaga gtttagctgt aacagttctt tttgatcatc ttttttaat aattagaaac   7920
accaaaaaaa tccagaaact tgttcttcca aagcagagag cattataatc accagggcca   7980
aaagcttccc tccctgctgt cattgcttct tctgaggcct gaatccaaaa gaaaaacagc   8040
cataggccct ttcagtggcc gggctacccg tgagcccttc ggaggaccag ggctggggca   8100
```

```
gcctctgggc ccacatccgg ggccagctcc ggcgtgtgtt cagtgttagc agtgggtcat   8160

gatgctcttt cccacccagc ctgggatagg ggcagaggag gcgaggaggc cgttgccgct   8220

gatgtttggc cgtgaacagg tgggtgtctg cgtgcgtcca cgtgcgtgtt ttctgactga   8280

catgaaatcg acgcccgagt tagcctcacc cggtgacctc tagccctgcc cggatggagc   8340

ggggcccacc cggttcagtg tttctgggga gctggacagt ggagtgcaaa aggcttgcag   8400

aacttgaagc ctgctccttc ccttgctacc acggcctcct ttccgtttga tttgtcactg   8460

cttcaatcaa taacagccgc tccagagtca gtagtcaatg aatatatgac caaatatcac   8520

caggactgtt actcaatgtg tgccgagccc ttgcccatgc tgggctcccg tgtatctgga   8580

cactgtaacg tgtgctgtgt ttgctcccct tcccttcct tctttgccct ttacttgtct    8640

ttctggggtt tttctgtttg ggtttggttt ggtttttatt tctccttttg tgttccaaac   8700

atgaggttct ctctactggt cctcttaact gtggtgttga ggcttatatt tgtgtaattt   8760

ttggtgggtg aaaggaattt tgctaagtaa atctcttctg tgtttgaact gaagtctgta   8820

ttgtaactat gtttaaagta attgttccag agacaaatat ttctagacac tttttcttta   8880

caaacaaaag cattcggagg gagggggatg gtgactgaga tgagagggga gagctgaaca   8940

gatgacccct gcccagatca gccagaagcc acccaaagca gtggagccca ggagtcccac   9000

tccaagccag caagccgaat agctgatgtg ttgccacttt ccaagtcact gcaaaaccag   9060

gttttgttcc gcccagtgga ttcttgtttt gcttcccctc cccccgagat tattaccacc   9120

atcccgtgct tttaaggaaa ggcaagattg atgtttcctt gaggggagcc aggaggggat   9180

gtgtgtgtgc agagctgaag agctggggag aatggggctg ggcccaccca agcaggaggc   9240

tgggacgctc tgctgtgggc acaggtcagg ctaatgttgg cagatgcagc tcttcctgga   9300

caggccaggt ggtgggcatt ctctctccaa ggtgtgcccc gtgggcatta ctgtttaaga   9360

cacttccgtc acatcccacc ccatcctcca gggctcaaca ctgtgacatc tctattcccc   9420

accctcccct tcccagggca ataaaatgac catggagggg gcttgcactc tcttggctgt   9480

cacccgatcg ccagcaaaac ttagatgtga gaaaacccct tcccattcca tggcgaaaac   9540

atctccttag aaaagccatt accctcatta ggcatggttt tgggctccca aaacacctga   9600

cagcccctcc ctcctctgag aggcggagag tgctgactgt agtgaccatt gcatgccggg   9660

tgcagcatct ggaagagcta ggcagggtgt ctgccccctc ctgagttgaa gtcatgctcc   9720

cctgtgccag cccagaggcc gagagctatg gacagcattg ccagtaacac aggccaccct   9780

gtgcagaagg gagctggctc cagcctggaa acctgtctga ggttgggaga ggtgcacttg   9840

gggcacaggg agaggccggg acacacttag ctggagatgt ctctaaaagc cctgtatcgt   9900

attcaccttc agtttttgtg ttttgggaca attactttag aaaataagta ggtcgtttta   9960

aaaacaaaaa ttattgattg ctttttgta gtgttcagaa aaaaggttct ttgtgtatag   10020

ccaaatgact gaaagcactg atatatttaa aaacaaaagg caatttatta aggaaatttg  10080

taccatttca gtaaacctgt ctgaatgtac ctgtatacgt ttcaaaaaca cccccccccc  10140

actgaatccc tgtaacctat ttattatata aagagtttgc cttataaatt t           10191
```

<210> SEQ ID NO 26
<211> LENGTH: 10179
<212> TYPE: DNA
<213> ORGANISM: Homo sapiens

<400> SEQUENCE: 26

```
ccggaaaatg gccgccgccg ccgccgcgcc gagcggagga ggaggaggag gcgaggagga     60
```

-continued

```
gagactgctc cataaaaata cagactcacc agttcctgct ttgatgtgac atgtgactcc    120
ccagaataca ccttgcttct gtagaccagc tccaacagga ttccatggta gctgggatgt    180
tagggctcag ggaagaaaag tcagaagacc aggacctcca gggcctcaag gacaaacccc    240
tcaagtttaa aaaggtgaag aaagataaga aagaagagaa agagggcaag catgagcccg    300
tgcagccatc agcccaccac tctgctgagc ccgcagaggc aggcaaagca gagacatcag    360
aagggtcagg ctccgccccg gctgtgccgg aagcttctgc ctccccaaa cagcggcgct    420
ccatcatccg tgaccgggga cccatgtatg atgaccccac cctgcctgaa ggctggacac    480
ggaagcttaa gcaaaggaaa tctggccgct ctgctgggaa gtatgatgtg tatttgatca    540
atccccaggg aaaagccttt cgctctaaag tggagttgat tgcgtacttc gaaaaggtag    600
gcgacacatc cctggaccct aatgattttg acttcacggt aactgggaga gggagcccct    660
cccggcgaga gcagaaacca cctaagaagc ccaaatctcc caaagctcca ggaactggca    720
gaggccgggg acgccccaaa gggagcggca ccacgagacc caaggcggcc acgtcagagg    780
gtgtgcaggt gaaaagggtc ctggagaaaa gtcctgggaa gctccttgtc aagatgcctt    840
ttcaaacttc gccagggggc aaggctgagg ggggtggggc caccacatcc acccaggtca    900
tggtgatcaa acgccccggc aggaagcgaa aagctgaggc cgaccctcag gccattccca    960
agaaacgggg ccgaaagccg gggagtgtgg tggcagccgc tgccgccgag gccaaaaaga   1020
aagccgtgaa ggagtcttct atccgatctg tgcaggagac cgtactcccc atcaagaagc   1080
gcaagacccg ggagacggtc agcatcgagg tcaaggaagt ggtgaagccc ctgctggtgt   1140
ccaccctcgg tgagaagagc gggaaaggac tgaagacctg taagagccct gggcggaaaa   1200
gcaaggagag cagccccaag gggcgcagca gcagcgcctc ctcacccccc aagaaggagc   1260
accaccacca tcaccaccac tcagagtccc caaaggcccc cgtgccactg ctcccacccc   1320
tgcccccacc tccacctgag cccgagagct ccgaggaccc caccagcccc cctgagcccc   1380
aggacttgag cagcagcgtc tgcaaagagg agaagatgcc cagaggaggc tcactggaga   1440
gcgacggctg ccccaaggag ccagctaaga ctcagcccgc ggttgccacc gccgccacgg   1500
ccgcagaaaa gtacaaacac cgaggggagg gagagcgcaa agacattgtt tcatcctcca   1560
tgccaaggcc aaacagagag gagcctgtgg acagccggac gcccgtgacc gagagagtta   1620
gctgacttta cacggagcgg attgcaaagc aaaccaacaa gaataaaggc agctgttgtc   1680
tcttctcctt atgggtaggg ctctgacaaa gcttcccgat taactgaaat aaaaaatatt   1740
ttttttctt tcagtaaact tagagtttcg tggcttcagg gtgggagtag ttggagcatt   1800
ggggatgttt ttcttaccga caagcacagt caggttgaag acctaaccag ggccagaagt   1860
agctttgcac ttttctaaac taggctcctt caacaaggct tgctgcagat actactgacc   1920
agacaagctg ttgaccaggc acctcccctc ccgcccaaac ctttccccca tgtggtcgtt   1980
agagacagag cgacagagca gttgagagga cactcccgtt ttcggtgcca tcagtgcccc   2040
gtctacagct cccccagctc cccccacctc ccccactccc aaccacgttg ggacagggag   2100
gtgtgaggca ggagagacag ttggattctt tagagaagat ggatatgacc agtggctatg   2160
gcctgtgcga tcccacccgt ggtggctcaa gtctggcccc acaccagccc caatccaaaa   2220
ctggcaagga cgcttcacag gacaggaaag tggcacctgt ctgctccagc tctggcatgg   2280
ctaggagggg ggagtccctt gaactactgg gtgtagactg gcctgaacca caggagagga   2340
tggcccaggg tgaggtggca tggtccattc tcaagggacg tcctccaacg ggtggcgcta   2400
gaggccatgg aggcagtagg acaaggtgca ggcaggctgg cctggggtca ggccgggcag   2460
```

-continued

```
agcacagcgg ggtgagaggg attcctaatc actcagagca gtctgtgact tagtggacag   2520
gggagggggc aaagggggag gagaagaaaa tgttcttcca gttactttcc aattctcctt   2580
tagggacagc ttagaattat ttgcactatt gagtcttcat gttcccactt caaaacaaac   2640
agatgctctg agagcaaact ggcttgaatt ggtgacattt agtccctcaa gccaccagat   2700
gtgacagtgt tgagaactac ctggatttgt atatatacct gcgcttgttt taaagtgggc   2760
tcagcacata gggttcccac gaagctccga aactctaagt gtttgctgca attttataag   2820
gacttcctga ttggtttctc ttctcccctt ccatttctgc cttttgttca tttcatcctt   2880
tcacttcttt cccttcctcc gtcctcctcc ttcctagttc atcccttctc ttccaggcag   2940
ccgcggtgcc caaccacact tgtcggctcc agtccccaga actctgcctg ccctttgtcc   3000
tcctgctgcc agtaccagcc ccaccctgtt ttgagccctg aggaggcctt gggctctgct   3060
gagtccgacc tggcctgtct gtgaagagca agagagcagc aaggtcttgc tctcctaggt   3120
agccccctct tccctggtaa gaaaaagcaa aaggcatttc ccaccctgaa caacgagcct   3180
tttcaccctt ctactctaga gaagtggact ggaggagctg ggcccgattt ggtagttgag   3240
gaaagcacag aggcctcctg tggcctgcca gtcatcgagt ggcccaacag gggctccatg   3300
ccagccgacc ttgacctcac tcagaagtcc agagtctagc gtagtgcagc agggcagtag   3360
cggtaccaat gcagaactcc caagacccga gctgggacca gtacctgggt ccccagccct   3420
tcctctgctc cccctttcc ctcggagttc ttcttgaatg gcaatgtttt gcttttgctc   3480
gatgcagaca gggggccaga acaccacaca tttcactgtc tgtctggtcc atagctgtgg   3540
tgtaggggct tagaggcatg ggcttgctgt gggtttttaa ttgatcagtt ttcatgtggg   3600
atcccatctt tttaacctct gttcaggaag tccttatcta gctgcatatc ttcatcatat   3660
tggtatatcc ttttctgtgt ttacagagat gtctcttata tctaaatctg tccaactgag   3720
aagtacctta tcaaagtagc aaatgagaca gcagtcttat gcttccagaa acacccacag   3780
gcatgtccca tgtgagctgc tgccatgaac tgtcaagtgt gtgttgtctt gtgtatttca   3840
gttattgtcc ctggcttcct tactatggtg taatcatgaa ggagtgaaac atcatagaaa   3900
ctgtctagca cttccttgcc agtctttagt gatcaggaac catagttgac agttccaatc   3960
agtagcttaa gaaaaaaccg tgtttgtctc ttctggaatg gttagaagtg agggagtttg   4020
ccccgttctg tttgtagagt ctcatagttg gactttctag catatatgtg tccatttcct   4080
tatgctgtaa aagcaagtcc tgcaaccaaa ctcccatcag cccaatccct gatccctgat   4140
cccttccacc tgctctgctg atgacccccc cagcttcact tctgactctt ccccaggaag   4200
ggaagggggg tcagaagaga gggtgagtcc tccagaactc ttcctccaag gacagaaggc   4260
tcctgccccc atagtggcct cgaactcctg gcactaccaa aggacactta tccacgagag   4320
cgcagcatcc gaccaggttg tcactgagaa gatgtttatt ttggtcagtt gggtttttat   4380
gtattatact tagtcaaatg taatgtggct tctggaatca ttgtccagag ctgcttcccc   4440
gtcacctggg cgtcatctgg tcctggtaag aggagtgcgt ggcccaccag gccccccctgt  4500
cacccatgac agttcattca gggccgatgg ggcagtcgtg gttgggaaca cagcatttca   4560
agcgtcactt tatttcattc gggccccacc tgcagctccc tcaaagaggc agttgcccag   4620
cctctttccc ttccagttta ttccagagct gccagtgggg cctgaggctc cttagggttt   4680
tctctctatt tccccctttc ttcctcattc cctcgtcttt cccaaaggca tcacgagtca   4740
gtcgcctttc agcaggcagc cttggcggtt tatcgccctg gcaggcaggg gccctgcagc   4800
tctcatgctg cccctgcctt ggggtcaggt tgacaggagg ttggagggaa agccttaagc   4860
```

```
tgcaggattc tcaccagctg tgtccggccc agttttgggg tgtgacctca atttcaattt   4920
tgtctgtact tgaacattat gaagatgggg gcctctttca gtgaatttgt gaacagcaga   4980
attgaccgac agctttccag tacccatggg gctaggtcat taaggccaca tccacagtct   5040
cccccaccct tgttccagtt gttagttact acctcctctc ctgacaatac tgtatgtcgt   5100
cgagctcccc ccaggtctac ccctcccggc cctgcctgct ggtgggcttg tcatagccag   5160
tgggattgcc ggtcttgaca gctcagtgag ctggagatac ttggtcacag ccaggcgcta   5220
gcacagctcc cttctgttga tgctgtattc ccatatcaaa agacacaggg gacacccaga   5280
aacgccacat cccccaatcc atcagtgcca aactagccaa cggccccagc ttctcagctc   5340
gctggatggc ggaagctgct actcgtgagc gccagtgcgg gtgcagacaa tcttctgttg   5400
ggtggcatca ttccaggccc gaagcatgaa cagtgcacct gggacaggga gcagccccaa   5460
attgtcacct gcttctctgc ccagcttttc attgctgtga cagtgatggc gaaagagggt   5520
aataaccaga cacaaactgc caagttgggt ggagaaagga gtttctttag ctgacagaat   5580
ctctgaattt taaatcactt agtaagcggc tcaagcccag gagggagcag agggatacga   5640
gcggagtccc ctgcgcggga ccatctggaa ttggtttagc ccaagtggag cctgacagcc   5700
agaactctgt gtcccccgtc taaccacagc tccttttcca gagcattcca gtcaggctct   5760
ctgggctgac tgggccaggg gaggttacag gtaccagttc tttaagaaga tctttgggca   5820
tatacatttt tagcctgtgt cattgcccca aatggattcc tgtttcaagt tcacacctgc   5880
agattctagg acctgtgtcc tagacttcag ggagtcagct gtttctagag ttcctaccat   5940
ggagtgggtc tggaggacct gcccggtggg ggggcagagc cctgctccct ccgggtcttc   6000
ctactcttct ctctgctctg acgggatttg ttgattctct ccattttggt gtctttctct   6060
tttagatatt gtatcaatct ttagaaaagg catagtctac ttgttataaa tcgttaggat   6120
actgcctccc ccagggtcta aaattacata ttagagggga aaagctgaac actgaagtca   6180
gttctcaaca atttagaagg aaaacctaga aaacatttgg cagaaaatta catttcgatg   6240
tttttgaatg aatacgagca agcttttaca acagtgctga tctaaaaata cttagcactt   6300
ggcctgagat gcctggtgag cattacaggc aaggggaatc tggaggtagc cgacctgagg   6360
acatggcttc tgaacctgtc ttttgggagt ggtatggaag gtggagcgtt caccagtgac   6420
ctggaaggcc cagcaccacc ctccttccca ctcttctcat cttgacagag cctgccccag   6480
cgctgacgtg tcaggaaaac acccagggaa ctaggaaggc acttctgcct gaggggcagc   6540
ctgccttgcc cactcctgct ctgctcgcct cggatcagct gagccttctg agctggcctc   6600
tcactgcctc cccaaggccc cctgcctgcc ctgtcaggag gcagaaggaa gcaggtgtga   6660
gggcagtgca aggagggagc acaaccccca gctcccgctc cgggctccga cttgtgcaca   6720
ggcagagccc agaccctgga ggaaatccta cctttgaatt caagaacatt tggggaattt   6780
ggaaatctct ttgcccccaa acccccattc tgtcctacct ttaatcaggt cctgctcagc   6840
agtgagagca gatgaggtga aaaggccaag aggtttggct cctgcccact gatagcccct   6900
ctccccgcag tgtttgtgtg tcaagtggca aagctgttct tcctggtgac cctgattata   6960
tccagtaaca catagactgt gcgcataggc ctgctttgtc tcctctatcc tgggcttttg   7020
ttttgctttt tagttttgct tttagttttt ctgtcccttt tatttaacgc accgactaga   7080
cacacaaagc agttgaattt ttatatatat atctgtatat tgcacaatta taaactcatt   7140
ttgcttgtgg ctccacacac acaaaaaaag acctgttaaa attatacctg ttgcttaatt   7200
acaatatttc tgataaccat agcataggac aagggaaaat aaaaaaagaa aaaaaagaaa   7260
```

```
aaaaaacgac aaatctgtct gctggtcact tcttctgtcc aagcagattc gtggtctttt   7320
cctcgcttct ttcaagggct ttcctgtgcc aggtgaagga ggctccaggc agcacccagg   7380
ttttgcactc ttgtttctcc cgtgcttgtg aaagaggtcc caaggttctg ggtgcaggag   7440
cgctcccttg acctgctgaa gtccggaacg tagtcggcac agcctggtcg ccttccacct   7500
ctgggagctg gagtccactg gggtggcctg actcccccag tccccttccc gtgacctggt   7560
cagggtgagc ccatgtggag tcagcctcgc aggcctccct gccagtaggg tccgagtgtg   7620
tttcatcctt cccactctgt cgagcctggg ggctggagcg gagacgggag gcctggcctg   7680
tctcggaacc tgtgagctgc accaggtaga acgccaggga ccccagaatc atgtgcgtca   7740
gtccaagggg tcccctccag gagtagtgaa gactccagaa atgtcccttt cttctccccc   7800
atcctacgag taattgcatt tgcttttgta attcttaatg agcaatatct gctagagagt   7860
ttagctgtaa cagttctttt tgatcatctt tttttaataa ttagaaacac caaaaaaatc   7920
cagaaacttg ttcttccaaa gcagagagca ttataatcac cagggccaaa agcttccctc   7980
cctgctgtca ttgcttcttc tgaggcctga atccaaaaga aaaacagcca taggcccttt   8040
cagtggccgg gctacccgtg agcccttcgg aggaccaggg ctggggcagc ctctgggccc   8100
acatccgggg ccagctccgg cgtgtgttca gtgttagcag tgggtcatga tgctctttcc   8160
cacccagcct gggatagggg cagaggaggc gaggaggccg ttgccgctga tgtttggccg   8220
tgaacaggtg ggtgtctgcg tgcgtccacg tgcgtgtttt ctgactgaca tgaaatcgac   8280
gcccgagtta gcctcacccg gtgacctcta gccctgcccg gatggagcgg ggcccacccg   8340
gttcagtgtt tctggggagc tggacagtgg agtgcaaaag gcttgcagaa cttgaagcct   8400
gctccttccc ttgctaccac ggcctccttt ccgtttgatt tgtcactgct tcaatcaata   8460
acagccgctc cagagtcagt agtcaatgaa tatatgacca aatatcacca ggactgttac   8520
tcaatgtgtg ccgagccctt gcccatgctg ggctcccgtg tatctggaca ctgtaacgtg   8580
tgctgtgttt gctccccttc cccttccttc tttgcccttt acttgtcttt ctggggtttt   8640
tctgtttggg tttggtttgg tttttatttc tccttttgtg ttccaaacat gaggttctct   8700
ctactggtcc tcttaactgt ggtgttgagg cttatatttg tgtaattttt ggtgggtgaa   8760
aggaattttg ctaagtaaat ctcttctgtg tttgaactga agtctgtatt gtaactatgt   8820
ttaaagtaat tgttccagag acaaatattt ctagacactt tttctttaca aacaaaagca   8880
ttcggaggga gggggatggt gactgagatg agaggggaga gctgaacaga tgacccctgc   8940
ccagatcagc cagaagccac ccaaagcagt ggagcccagg agtcccactc caagccagca   9000
agccgaatag ctgatgtgtt gccactttcc aagtcactgc aaaaccaggt tttgttccgc   9060
ccagtggatt cttgttttgc ttcccctccc cccgagatta ttaccaccat cccgtgcttt   9120
taaggaaagg caagattgat gtttccttga ggggagccag gaggggatgt gtgtgtgcag   9180
agctgaagag ctggggagaa tggggctggg cccacccaag caggaggctg ggacgctctg   9240
ctgtgggcac aggtcaggct aatgttggca gatgcagctc ttcctggaca ggccaggtgg   9300
tgggcattct ctctccaagg tgtgccccgt gggcattact gtttaagaca cttccgtcac   9360
atcccacccc atcctccagg gctcaacact gtgacatctc tattccccac cctccccttc   9420
ccagggcaat aaaatgacca tggagggggc ttgcactctc ttggctgtca cccgatcgcc   9480
agcaaaactt agatgtgaga aaaccccttc ccattccatg gcgaaaacat ctccttagaa   9540
aagccattac cctcattagg catggttttg ggctcccaaa acacctgaca gcccctccct   9600
cctctgagag gcggagagtg ctgactgtag tgaccattgc atgccgggtg cagcatctgg   9660
```

```
aagagctagg cagggtgtct gccccctcct gagttgaagt catgctcccc tgtgccagcc   9720

cagaggccga gagctatgga cagcattgcc agtaacacag gccaccctgt gcagaaggga   9780

gctggctcca gcctggaaac ctgtctgagg ttgggagagg tgcacttggg gcacagggag   9840

aggccgggac acacttagct ggagatgtct ctaaaagccc tgtatcgtat tcaccttcag   9900

tttttgtgtt ttgggacaat tactttagaa aataagtagg tcgttttaaa aacaaaaatt   9960

attgattgct tttttgtagt gttcagaaaa aaggttcttt gtgtatagcc aaatgactga  10020

aagcactgat atatttaaaa acaaaaggca atttattaag gaaatttgta ccatttcagt  10080

aaacctgtct gaatgtacct gtatacgttt caaaaacacc cccccccac tgaatccctg  10140

taacctattt attatataaa gagtttgcct tataaattt                         10179
```

<210> SEQ ID NO 27
<211> LENGTH: 10185
<212> TYPE: DNA
<213> ORGANISM: Homo sapiens

<400> SEQUENCE: 27

```
ccggaaaatg gccgccgccg ccgccgccgc gccgagcgga ggaggaggag gaggaggcga     60

ggaggagaga ctgctccata aaaatacaga ctcaccagtt cctgctttga tgtgacatgt    120

gactccccag aatacacctt gcttctgtag accagctcca acaggattcc atggtagctg    180

ggatgttagg gctcagggaa gaaaagtcag aagaccagga cctccagggc ctcaaggaca    240

aacccctcaa gtttaaaaag gtgaagaaag ataagaaaga agagaaagag ggcaagcatg    300

agcccgtgca gccatcagcc caccactctg ctgagcccgc agaggcaggc aaagcagaga    360

catcagaagg gtcaggctcc gccccggctg tgccggaagc ttctgcctcc cccaaacagc    420

ggcgctccat catccgtgac cggggaccca tgtatgatga ccccaccctg cctgaaggct    480

ggacacggaa gcttaagcaa aggaaatctg gccgctctgc tgggaagtat gatgtgtatt    540

tgatcaatcc ccagggaaaa gcctttcgct ctaaagtgga gttgattgcg tacttcgaaa    600

aggtaggcga cacatccctg gaccctaatg attttgactt cacggtaact gggagaggga    660

gcccctcccg gcgagagcag aaaccaccta agaagcccaa atctcccaaa gctccaggaa    720

ctggcagagg ccggggacgc ccccaaaggga gcggcaccac gagacccaag gcggccacgt    780

cagagggtgt gcaggtgaaa agggtcctgg agaaaagtcc tgggaagctc cttgtcaaga    840

tgccttttca aacttcgcca gggggcaagg ctgagggggg tggggccacc acatccaccc    900

aggtcatggt gatcaaacgc cccggcagga agcgaaaagc tgaggccgac cctcaggcca    960

ttcccaagaa acggggccga aagccgggga gtgtggtggc agccgctgcc gccgaggcca   1020

aaaagaaagc cgtgaaggag tcttctatcc gatctgtgca ggagaccgta ctccccatca   1080

agaagcgcaa gacccgggag acggtcagca tcgaggtcaa ggaagtggtg aagcccctgc   1140

tggtgtccac cctcggtgag aagagcggga aaggactgaa gacctgtaag agccctgggc   1200

ggaaaagcaa ggagagcagc cccaaggggc gcagcagcag cgcctcctca ccccccaaga   1260

aggagcacca ccaccatcac caccactcag agtccccaaa ggcccccgtg ccactgctcc   1320

cacccctgcc cccacctcca cctgagcccg agagctccga ggaccccacc agccccccctg   1380

agccccagga cttgagcagc agcgtctgca aagaggagaa gatgcccaga ggaggctcac   1440

tggagagcga cggctgcccc aaggagccag ctaagactca gcccgcggtt gccaccgccg   1500

ccacggccgc agaaaagtac aaacaccgag gggagggaga gcgcaaagac attgtttcat   1560

cctccatgcc aaggccaaac agagaggagc ctgtggacag ccggacgccc gtgaccgaga   1620
```

```
gagttagctg actttacacg gagcggattg caaagcaaac caacaagaat aaaggcagct   1680
gttgtctctt ctccttatgg gtagggctct gacaaagctt cccgattaac tgaaataaaa   1740
aatatttttt tttctttcag taaacttaga gtttcgtggc ttcagggtgg gagtagttgg   1800
agcattgggg atgtttttct taccgacaag cacagtcagg ttgaagacct aaccagggcc   1860
agaagtagct ttgcactttt ctaaactagg ctccttcaac aaggcttgct gcagatacta   1920
ctgaccagac aagctgttga ccaggcacct cccctcccgc ccaaaccttt cccccatgtg   1980
gtcgttagag acagagcgac agagcagttg agaggacact cccgttttcg gtgccatcag   2040
tgccccgtct acagctcccc cagctccccc cacctccccc actcccaacc acgttgggac   2100
agggaggtgt gaggcaggag agacagttgg attctttaga gaagatggat atgaccagtg   2160
gctatggcct gtgcgatccc acccgtggtg gctcaagtct ggccccacac cagccccaat   2220
ccaaaactgg caaggacgct tcacaggaca ggaaagtggc acctgtctgc tccagctctg   2280
gcatggctag gagggggag tcccttgaac tactgggtgt agactggcct gaaccacagg   2340
agaggatggc ccagggtgag gtggcatggt ccattctcaa gggacgtcct ccaacgggtg   2400
gcgctagagg ccatggaggc agtaggacaa ggtgcaggca ggctggcctg gggtcaggcc   2460
gggcagagca cagcggggtg agagggattc ctaatcactc agagcagtct gtgacttagt   2520
ggacagggga gggggcaaag ggggaggaga agaaaatgtt cttccagtta ctttccaatt   2580
ctcctttagg gacagcttag aattatttgc actattgagt cttcatgttc ccacttcaaa   2640
acaaacagat gctctgagag caaactggct tgaattggtg acatttagtc cctcaagcca   2700
ccagatgtga cagtgttgag aactacctgg atttgtatat atacctgcgc ttgttttaaa   2760
gtgggctcag cacatagggt tcccacgaag ctccgaaact ctaagtgttt gctgcaattt   2820
tataaggact tcctgattgg tttctcttct cccctcccat ttctgccttt tgttcatttc   2880
atcctttcac ttctttccct tcctccgtcc tcctccttcc tagttcatcc cttctcttcc   2940
aggcagccgc ggtgcccaac cacacttgtc ggctccagtc cccagaactc tgcctgccct   3000
ttgtcctcct gctgccagta ccagccccac cctgttttga gccctgagga ggccttgggc   3060
tctgctgagt ccgacctggc ctgtctgtga agagcaagag agcagcaagg tcttgctctc   3120
ctaggtagcc ccctcttccc tggtaagaaa aagcaaaagg catttcccac cctgaacaac   3180
gagccttttc acccttctac tctagagaag tggactggag gagctgggcc cgatttggta   3240
gttgaggaaa gcacagaggc ctcctgtggc ctgccagtca tcgagtggcc caacaggggc   3300
tccatgccag ccgaccttga cctcactcag aagtccagag tctagcgtag tgcagcaggg   3360
cagtagcggt accaatgcag aactcccaag acccgagctg ggaccagtac ctgggtcccc   3420
agcccttcct ctgctccccc ttttccctcg gagttcttct tgaatggcaa tgttttgctt   3480
ttgctcgatg cagacagggg gccagaacac cacacatttc actgtctgtc tggtccatag   3540
ctgtggtgta ggggcttaga ggcatgggct tgctgtgggt ttttaattga tcagttttca   3600
tgtgggatcc catcttttta acctctgttc aggaagtcct tatctagctg catatcttca   3660
tcatattggt atatcctttt ctgtgtttac agagatgtct cttatatcta aatctgtcca   3720
actgagaagt accttatcaa agtagcaaat gagacagcag tcttatgctt ccagaaacac   3780
ccacaggcat gtcccatgtg agctgctgcc atgaactgtc aagtgtgtgt tgtcttgtgt   3840
atttcagtta ttgtccctgg cttccttact atggtgtaat catgaaggag tgaaacatca   3900
tagaaactgt ctagcacttc cttgccagtc tttagtgatc aggaaccata gttgacagtt   3960
ccaatcagta gcttaagaaa aaaccgtgtt tgtctcttct ggaatggtta gaagtgaggg   4020
```

-continued

```
agtttgcccc gttctgtttg tagagtctca tagttggact ttctagcata tatgtgtcca   4080
tttccttatg ctgtaaaagc aagtcctgca accaaactcc catcagccca atccctgatc   4140
cctgatccct tccacctgct ctgctgatga cccccccagc ttcacttctg actcttcccc   4200
aggaagggaa ggggggtcag aagagagggt gagtcctcca gaactcttcc tccaaggaca   4260
gaaggctcct gcccccatag tggcctcgaa ctcctggcac taccaaagga cacttatcca   4320
cgagagcgca gcatccgacc aggttgtcac tgagaagatg tttattttgg tcagttgggt   4380
ttttatgtat tatacttagt caaatgtaat gtggcttctg gaatcattgt ccagagctgc   4440
ttccccgtca cctgggcgtc atctggtcct ggtaagagga gtgcgtggcc caccaggccc   4500
ccctgtcacc catgacagtt cattcagggc cgatggggca gtcgtggttg ggaacacagc   4560
atttcaagcg tcactttatt tcattcgggc cccacctgca gctccctcaa agaggcagtt   4620
gcccagcctc tttcccttcc agtttattcc agagctgcca gtggggcctg aggctcctta   4680
gggttttctc tctatttccc cctttcttcc tcattccctc gtctttccca aaggcatcac   4740
gagtcagtcg cctttcagca ggcagccttg gcggtttatc gccctggcag gcaggggccc   4800
tgcagctctc atgctgcccc tgccttgggg tcaggttgac aggaggttgg agggaaagcc   4860
ttaagctgca ggattctcac cagctgtgtc cggcccagtt ttggggtgtg acctcaattt   4920
caattttgtc tgtacttgaa cattatgaag atgggggcct ctttcagtga atttgtgaac   4980
agcagaattg accgacagct ttccagtacc catggggcta ggtcattaag gccacatcca   5040
cagtctcccc cacccttgtt ccagttgtta gttactacct cctctcctga caatactgta   5100
tgtcgtcgag ctccccccag gtctacccct cccggccctg cctgctggtg ggcttgtcat   5160
agccagtggg attgccggtc ttgacagctc agtgagctgg agatacttgg tcacagccag   5220
gcgctagcac agctcccttc tgttgatgct gtattcccat atcaaaagac acaggggaca   5280
cccagaaacg ccacatcccc caatccatca gtgccaaact agccaacggc cccagcttct   5340
cagctcgctg gatggcggaa gctgctactc gtgagcgcca gtgcgggtgc agacaatctt   5400
ctgttgggtg gcatcattcc aggcccgaag catgaacagt gcacctggga cagggagcag   5460
ccccaaattg tcacctgctt ctctgcccag cttttcattg ctgtgacagt gatggcgaaa   5520
gagggtaata accagacaca aactgccaag ttgggtggag aaaggagttt ctttagctga   5580
cagaatctct gaattttaaa tcacttagta agcggctcaa gcccaggagg gagcagaggg   5640
atacgagcgg agtcccctgc gcgggaccat ctggaattgg tttagcccaa gtggagcctg   5700
acagccagaa ctctgtgtcc cccgtctaac cacagctcct tttccagagc attccagtca   5760
ggctctctgg gctgactggg ccaggggagg ttacaggtac cagttcttta agaagatctt   5820
tgggcatata catttttagc ctgtgtcatt gccccaaatg gattcctgtt tcaagttcac   5880
acctgcagat tctaggacct gtgtcctaga cttcagggag tcagctgttt ctagagttcc   5940
taccatggag tgggtctgga ggacctgccc ggtggggggg cagagccctg ctccctccgg   6000
gtcttcctac tcttctctct gctctgacgg gatttgttga ttctctccat tttggtgtct   6060
ttctctttta gatattgtat caatctttag aaaaggcata gtctacttgt tataaatcgt   6120
taggatactg cctcccccag ggtctaaaat tacatattag aggggaaaag ctgaacactg   6180
aagtcagttc tcaacaattt agaaggaaaa cctagaaaac atttggcaga aaattacatt   6240
tcgatgtttt tgaatgaata cgagcaagct tttacaacag tgctgatcta aaaatactta   6300
gcacttggcc tgagatgcct ggtgagcatt acaggcaagg ggaatctgga ggtagccgac   6360
ctgaggacat ggcttctgaa cctgtctttt gggagtggta tggaaggtgg agcgttcacc   6420
```

-continued

```
agtgacctgg aaggcccagc accaccctcc ttcccactct tctcatcttg acagagcctg   6480
ccccagcgct gacgtgtcag gaaaacaccc agggaactag gaaggcactt ctgcctgagg   6540
ggcagcctgc cttgcccact cctgctctgc tcgcctcgga tcagctgagc cttctgagct   6600
ggcctctcac tgcctcccca aggccccctg cctgccctgt caggaggcag aaggaagcag   6660
gtgtgagggc agtgcaagga gggagcacaa cccccagctc ccgctccggg ctccgacttg   6720
tgcacaggca gagcccagac cctggaggaa atcctacctt tgaattcaag aacatttggg   6780
gaatttggaa atctctttgc cccaaaccc ccattctgtc ctacctttaa tcaggtcctg   6840
ctcagcagtg agagcagatg aggtgaaaag gccaagaggt ttggctcctg cccactgata   6900
gcccctctcc ccgcagtgtt tgtgtgtcaa gtggcaaagc tgttcttcct ggtgaccctg   6960
attatatcca gtaacacata gactgtgcgc ataggcctgc tttgtctcct ctatcctggg   7020
cttttgtttt gctttttagt tttgctttta gtttttctgt cccttttatt taacgcaccg   7080
actagacaca caaagcagtt gaatttttat atatatatct gtatattgca caattataaa   7140
ctcattttgc ttgtggctcc acacacacaa aaaaagacct gttaaaatta tacctgttgc   7200
ttaattacaa tatttctgat aaccatagca taggacaagg gaaaataaaa aaagaaaaaa   7260
aagaaaaaaa aacgacaaat ctgtctgctg gtcacttctt ctgtccaagc agattcgtgg   7320
tcttttcctc gcttctttca agggctttcc tgtgccaggt gaaggaggct ccaggcagca   7380
cccaggtttt gcactcttgt ttctcccgtg cttgtgaaag aggtcccaag gttctgggtg   7440
caggagcgct cccttgacct gctgaagtcc ggaacgtagt cggcacagcc tggtcgcctt   7500
ccacctctgg gagctggagt ccactggggt ggcctgactc ccccagtccc cttcccgtga   7560
cctggtcagg gtgagcccat gtggagtcag cctcgcaggc ctccctgcca gtagggtccg   7620
agtgtgtttc atccttccca ctctgtcgag cctgggggct ggagcggaga cgggaggcct   7680
ggcctgtctc ggaacctgtg agctgcacca ggtagaacgc cagggacccc agaatcatgt   7740
gcgtcagtcc aaggggtccc ctccaggagt agtgaagact ccagaaatgt ccctttcttc   7800
tcccccatcc tacgagtaat tgcatttgct tttgtaattc ttaatgagca atatctgcta   7860
gagagtttag ctgtaacagt tctttttgat catctttttt taataattag aaacaccaaa   7920
aaaatccaga aacttgttct tccaaagcag agagcattat aatcaccagg gccaaaagct   7980
tccctccctg ctgtcattgc ttcttctgag gcctgaatcc aaaagaaaaa cagccatagg   8040
ccctttcagt ggccgggcta cccgtgagcc cttcggagga ccagggctgg ggcagcctct   8100
gggcccacat ccggggccag ctccggcgtg tgttcagtgt tagcagtggg tcatgatgct   8160
ctttcccacc cagcctggga taggggcaga ggaggcgagg aggccgttgc cgctgatgtt   8220
tggccgtgaa caggtgggtg tctgcgtgcg tccacgtgcg tgttttctga ctgacatgaa   8280
atcgacgccc gagttagcct cacccggtga cctctagccc tgcccggatg gagcggggcc   8340
cacccggttc agtgtttctg gggagctgga cagtggagtg caaaaggctt gcagaacttg   8400
aagcctgctc cttcccttgc taccacggcc tcctttccgt ttgatttgtc actgcttcaa   8460
tcaataacag ccgctccaga gtcagtagtc aatgaatata tgaccaaata tcaccaggac   8520
tgttactcaa tgtgtgccga gcccttgccc atgctgggct cccgtgtatc tggacactgt   8580
aacgtgtgct gtgtttgctc cccttcccct tccttctttg ccctttactt gtctttctgg   8640
ggtttttctg tttgggtttg gtttggtttt tatttctcct tttgtgttcc aaacatgagg   8700
ttctctctac tggtcctctt aactgtggtg ttgaggctta tatttgtgta atttttggtg   8760
ggtgaaagga attttgctaa gtaaatctct tctgtgtttg aactgaagtc tgtattgtaa   8820
```

```
ctatgtttaa agtaattgtt ccagagacaa atatttctag acactttttc tttacaaaca   8880

aaagcattcg gagggagggg gatggtgact gagatgagag gggagagctg aacagatgac   8940

ccctgcccag atcagccaga agccacccaa agcagtggag cccaggagtc ccactccaag   9000

ccagcaagcc gaatagctga tgtgttgcca ctttccaagt cactgcaaaa ccaggttttg   9060

ttccgcccag tggattcttg ttttgcttcc cctccccccg agattattac caccatcccg   9120

tgcttttaag gaaaggcaag attgatgttt ccttgagggg agccaggagg ggatgtgtgt   9180

gtgcagagct gaagagctgg ggagaatggg gctgggccca cccaagcagg aggctgggac   9240

gctctgctgt gggcacaggt caggctaatg ttggcagatg cagctcttcc tggacaggcc   9300

aggtggtggg cattctctct ccaaggtgtg ccccgtgggc attactgttt aagacacttc   9360

cgtcacatcc caccccatcc tccagggctc aacactgtga catctctatt ccccaccctc   9420

cccttcccag ggcaataaaa tgaccatgga gggggcttgc actctcttgg ctgtcacccg   9480

atcgccagca aaacttagat gtgagaaaac cccttcccat tccatggcga aaacatctcc   9540

ttagaaaagc cattaccctc attaggcatg gttttgggct cccaaaacac ctgacagccc   9600

ctccctcctc tgagaggcgg agagtgctga ctgtagtgac cattgcatgc cgggtgcagc   9660

atctggaaga gctaggcagg gtgtctgccc cctcctgagt tgaagtcatg ctcccctgtg   9720

ccagcccaga ggccgagagc tatggacagc attgccagta acacaggcca ccctgtgcag   9780

aagggagctg gctccagcct ggaaacctgt ctgaggttgg gagaggtgca cttggggcac   9840

agggagaggc cgggacacac ttagctggag atgtctctaa aagccctgta tcgtattcac   9900

cttcagtttt tgtgttttgg gacaattact ttagaaaata agtaggtcgt tttaaaaaca   9960

aaaattattg attgcttttt tgtagtgttc agaaaaaagg ttctttgtgt atagccaaat  10020

gactgaaagc actgatatat ttaaaaacaa aaggcaattt attaaggaaa tttgtaccat  10080

ttcagtaaac ctgtctgaat gtacctgtat acgtttcaaa aacacccccc ccccactgaa  10140

tccctgtaac ctatttatta tataaagagt ttgccttata aattt                  10185

<210> SEQ ID NO 28
<211> LENGTH: 10227
<212> TYPE: DNA
<213> ORGANISM: Homo sapiens

<400> SEQUENCE: 28

gggcgcgcgc tccctcctct cggagagagg gctgtggtaa aagccgtccg gaaaatgcgc     60

cgccgccgcc gccgcgccga gcggaggagg aggaggaggc gaggaggaga gactgctcca    120

taaaaataca gactcaccag ttcctgcttt gatgtgacat gtgactcccc agaatacacc    180

ttgcttctgt agaccagctc caacaggatt ccatggtagc tgggatgtta gggctcaggg    240

aagaaaagtc agaagaccag gacctccagg gcctcaagga caaacccctc aagtttaaaa    300

aggtgaagaa agataagaaa gaagagaaag agggcaagca tgagcccgtg cagccatcag    360

cccaccactc tgctgagccc gcagaggcag gcaaagcaga gacatcagaa gggtcaggct    420

ccgccccggc tgtgccggaa gcttctgcct cccccaaaca gcggcgctcc atcatccgtg    480

accggggacc catgtatgat gaccccaccc tgcctgaagg ctggacacgg aagcttaagc    540

aaaggaaatc tggccgctct gctgggaagt atgatgtgta tttgatcaat ccccagggaa    600

aagcctttcg ctctaaagtg gagttgattg cgtacttcga aaaggtaggc gacacatccc    660

tggaccctaa tgattttgac ttcacggtaa ctgggagagg gagcccctcc cggcgagagc    720

agaaaccacc taagaagccc aaatctccca aagctccagg aactggcaga ggccggggac    780
```

-continued

```
gccccaaagg gagcggcacc acgagaccca aggcggccac gtcagagggt gtgcaggtga    840
aaagggtcct ggagaaaagt cctgggaagc tccttgtcaa gatgcctttt caaacttcgc    900
cagggggcaa ggctgagggg ggtggggcca ccacatccac ccaggtcatg gtgatcaaac    960
gccccggcag gaagcgaaaa gctgaggccg accctcaggc cattcccaag aaacggggcc   1020
gaaagccggg gagtgtggtg gcagccgctg ccgccgaggc caaaaagaaa gccgtgaagg   1080
agtcttctat ccgatctgtg caggagaccg tactccccat caagaagcgc aagacccggg   1140
agacggtcag catcgaggtc aaggaagtgg tgaagcccct gctggtgtcc accctcggtg   1200
agaagagcgg gaaaggactg aagacctgta agagccctgg gcggaaaagc aaggagagca   1260
gccccaaggg gcgcagcagc agcgcctcct caccccccaa gaaggagcac caccaccatc   1320
accaccactc agagtcccca aaggcccccg tgccactgct cccacccctg cccccacctc   1380
cacctgagcc cgagagctcc gaggacccca ccagcccccc tgagccccag gacttgagca   1440
gcagcgtctg caaagaggag aagatgccca gaggaggctc actggagagc gacggctgcc   1500
ccaaggagcc agctaagact cagcccgcgg ttgccaccgc cgccacggcc gcagaaaagt   1560
acaaacaccg aggggaggga gagcgcaaag acattgtttc atcctccatg ccaaggccaa   1620
acagagagga gcctgtggac agccggacgc ccgtgaccga gagagttagc tgactttaca   1680
cggagcggat tgcaaagcaa accaacaaga ataaaggcag ctgttgtctc ttctccttat   1740
gggtagggct ctgacaaagc ttcccgatta actgaaataa aaaatatttt tttttctttc   1800
agtaaactta gagtttcgtg gcttcagggt gggagtagtt ggagcattgg ggatgttttt   1860
cttaccgaca agcacagtca ggttgaagac ctaaccaggg ccagaagtag ctttgcactt   1920
ttctaaacta ggctccttca acaaggcttg ctgcagatac tactgaccag acaagctgtt   1980
gaccaggcac ctcccctccc gcccaaacct ttcccccatg tggtcgttag agacagagcg   2040
acagagcagt tgagaggaca ctcccgtttt cggtgccatc agtgccccgt ctacagctcc   2100
cccagctccc cccacctccc ccactcccaa ccacgttggg acagggaggt gtgaggcagg   2160
agagacagtt ggattcttta gagaagatgg atatgaccag tggctatggc ctgtgcgatc   2220
ccacccgtgg tggctcaagt ctggccccac accagcccca atccaaaact ggcaaggacg   2280
cttcacagga caggaaagtg gcacctgtct gctccagctc tggcatggct aggagggggg   2340
agtcccttga actactgggt gtagactggc ctgaaccaca ggagaggatg gcccagggtg   2400
aggtggcatg gtccattctc aagggacgtc ctccaacggg tggcgctaga ggccatggag   2460
gcagtaggac aaggtgcagg caggctggcc tggggtcagg ccgggcagag cacagcgggg   2520
tgagagggat tcctaatcac tcagagcagt ctgtgactta gtggacaggg gagggggcaa   2580
agggggagga gaagaaaatg ttcttccagt tactttccaa ttctccttta gggacagctt   2640
agaattattt gcactattga gtcttcatgt tcccacttca aaacaaacag atgctctgag   2700
agcaaactgg cttgaattgg tgacatttag tccctcaagc caccagatgt gacagtgttg   2760
agaactacct ggatttgtat atatacctgc gcttgtttta aagtgggctc agcacatagg   2820
gttcccacga agctccgaaa ctctaagtgt ttgctgcaat tttataagga cttcctgatt   2880
ggtttctctt ctccccttcc atttctgcct tttgttcatt tcatcctttc acttctttcc   2940
cttcctccgt cctcctcctt cctagttcat cccttctctt ccaggcagcc gcggtgccca   3000
accacacttg tcggctccag tccccagaac tctgcctgcc ctttgtcctc ctgctgccag   3060
taccagcccc accctgtttt gagccctgag gaggccttgg gctctgctga gtccgacctg   3120
gcctgtctgt gaagagcaag agagcagcaa ggtcttgctc tcctaggtag ccccctcttc   3180
```

```
cctggtaaga aaaagcaaaa ggcatttccc accctgaaca acgagccttt tcacccttct   3240
actctagaga agtggactgg aggagctggg cccgatttgg tagttgagga aagcacagag   3300
gcctcctgtg gcctgccagt catcgagtgg cccaacaggg gctccatgcc agccgacctt   3360
gacctcactc agaagtccag agtctagcgt agtgcagcag ggcagtagcg gtaccaatgc   3420
agaactccca agacccgagc tgggaccagt acctgggtcc ccagcccttc ctctgctccc   3480
ccttttccct cggagttctt cttgaatggc aatgttttgc ttttgctcga tgcagacagg   3540
gggccagaac accacacatt tcactgtctg tctggtccat agctgtggtg taggggctta   3600
gaggcatggg cttgctgtgg gtttttaatt gatcagtttt catgtgggat cccatctttt   3660
taacctctgt tcaggaagtc cttatctagc tgcatatctt catcatattg gtatatcctt   3720
ttctgtgttt acagagatgt ctcttatatc taaatctgtc caactgagaa gtaccttatc   3780
aaagtagcaa atgagacagc agtcttatgc ttccagaaac acccacaggc atgtcccatg   3840
tgagctgctg ccatgaactg tcaagtgtgt gttgtcttgt gtatttcagt tattgtccct   3900
ggcttcctta ctatggtgta atcatgaagg agtgaaacat catagaaact gtctagcact   3960
tccttgccag tctttagtga tcaggaacca tagttgacag ttccaatcag tagcttaaga   4020
aaaaaccgtg tttgtctctt ctggaatggt tagaagtgag ggagtttgcc ccgttctgtt   4080
tgtagagtct catagttgga ctttctagca tatatgtgtc catttcctta tgctgtaaaa   4140
gcaagtcctg caaccaaact cccatcagcc caatccctga tccctgatcc cttccacctg   4200
ctctgctgat gacccccccca gcttcacttc tgactcttcc ccaggaaggg aagggggtc   4260
agaagagagg gtgagtcctc cagaactctt cctccaagga cagaaggctc ctgcccccat   4320
agtggcctcg aactcctggc actaccaaag gacacttatc cacgagagcg cagcatccga   4380
ccaggttgtc actgagaaga tgtttatttt ggtcagttgg gtttttatgt attatactta   4440
gtcaaatgta atgtggcttc tggaatcatt gtccagagct gcttccccgt cacctgggcg   4500
tcatctggtc ctggtaagag gagtgcgtgg cccaccaggc ccccctgtca cccatgacag   4560
ttcattcagg gccgatgggg cagtcgtggt tgggaacaca gcatttcaag cgtcacttta   4620
tttcattcgg gccccacctg cagctccctc aaagaggcag ttgcccagcc tctttccctt   4680
ccagtttatt ccagagctgc cagtggggcc tgaggctcct tagggttttc tctctatttc   4740
cccctttctt cctcattccc tcgtctttcc caaaggcatc acgagtcagt cgcctttcag   4800
caggcagcct tggcggttta tcgccctggc aggcaggggc cctgcagctc tcatgctgcc   4860
cctgccttgg ggtcaggttg acaggaggtt ggagggaaag ccttaagctg caggattctc   4920
accagctgtg tccggcccag ttttggggtg tgacctcaat ttcaattttg tctgtacttg   4980
aacattatga agatgggggc ctctttcagt gaatttgtga acagcagaat tgaccgacag   5040
ctttccagta cccatggggc taggtcatta aggccacatc cacagtctcc cccacccttg   5100
ttccagttgt tagttactac ctcctctcct gacaatactg tatgtcgtcg agctcccccc   5160
aggtctaccc ctcccggccc tgcctgctgg tgggcttgtc atagccagtg ggattgccgg   5220
tcttgacagc tcagtgagct ggagatactt ggtcacagcc aggcgctagc acagctccct   5280
tctgttgatg ctgtattccc atatcaaaag acacagggga cacccagaaa cgccacatcc   5340
cccaatccat cagtgccaaa ctagccaacg gccccagctt ctcagctcgc tggatggcgg   5400
aagctgctac tcgtgagcgc cagtgcgggt gcagacaatc ttctgttggg tggcatcatt   5460
ccaggcccga agcatgaaca gtgcacctgg gacagggagc agccccaaat tgtcacctgc   5520
ttctctgccc agcttttcat tgctgtgaca gtgatggcga aagagggtaa taaccagaca   5580
```

-continued

```
caaactgcca agttgggtgg agaaaggagt ttctttagct gacagaatct ctgaatttta   5640
aatcacttag taagcggctc aagcccagga gggagcagag ggatacgagc ggagtcccct   5700
gcgcgggacc atctggaatt ggtttagccc aagtggagcc tgacagccag aactctgtgt   5760
cccccgtcta accacagctc cttttccaga gcattccagt caggctctct gggctgactg   5820
ggccagggga ggttacaggt accagttctt taagaagatc tttgggcata tacattttta   5880
gcctgtgtca ttgccccaaa tggattcctg tttcaagttc acacctgcag attctaggac   5940
ctgtgtccta gacttcaggg agtcagctgt ttctagagtt cctaccatgg agtgggtctg   6000
gaggacctgc ccggtggggg ggcagagccc tgctccctcc gggtcttcct actcttctct   6060
ctgctctgac gggatttgtt gattctctcc attttggtgt ctttctcttt tagatattgt   6120
atcaatcttt agaaaaggca tagtctactt gttataaatc gttaggatac tgcctccccc   6180
agggtctaaa attacatatt agaggggaaa agctgaacac tgaagtcagt tctcaacaat   6240
ttagaaggaa aacctagaaa acatttggca gaaaattaca tttcgatgtt tttgaatgaa   6300
tacgagcaag cttttacaac agtgctgatc taaaaatact tagcacttgg cctgagatgc   6360
ctggtgagca ttacaggcaa ggggaatctg gaggtagccg acctgaggac atggcttctg   6420
aacctgtctt ttgggagtgg tatggaaggt ggagcgttca ccagtgacct ggaaggccca   6480
gcaccaccct ccttcccact cttctcatct tgacagagcc tgccccagcg ctgacgtgtc   6540
aggaaaacac ccagggaact aggaaggcac ttctgcctga ggggcagcct gccttgccca   6600
ctcctgctct gctcgcctcg gatcagctga gccttctgag ctggcctctc actgcctccc   6660
caaggccccc tgcctgccct gtcaggaggc agaaggaagc aggtgtgagg gcagtgcaag   6720
gagggagcac aacccccagc tcccgctccg ggctccgact tgtgcacagg cagagcccag   6780
accctggagg aaatcctacc tttgaattca agaacatttg gggaatttgg aaatctcttt   6840
gcccccaaac ccccattctg tcctaccttt aatcaggtcc tgctcagcag tgagagcaga   6900
tgaggtgaaa aggccaagag gtttggctcc tgcccactga tagcccctct ccccgcagtg   6960
tttgtgtgtc aagtggcaaa gctgttcttc ctggtgaccc tgattatatc cagtaacaca   7020
tagactgtgc gcataggcct gctttgtctc ctctatcctg ggcttttgtt ttgcttttta   7080
gttttgcttt tagtttttct gtccctttta tttaacgcac cgactagaca cacaaagcag   7140
ttgaattttt atatatatat ctgtatattg cacaattata aactcatttt gcttgtggct   7200
ccacacacac aaaaaaagac ctgttaaaat tatacctgtt gcttaattac aatatttctg   7260
ataaccatag catagacaa gggaaaataa aaaaagaaaa aaaagaaaaa aaaacgacaa   7320
atctgtctgc tggtcacttc ttctgtccaa gcagattcgt ggtcttttcc tcgcttcttt   7380
caagggcttt cctgtgccag gtgaaggagg ctccaggcag cacccaggtt ttgcactctt   7440
gtttctcccg tgcttgtgaa agaggtccca aggttctggg tgcaggagcg ctcccttgac   7500
ctgctgaagt ccggaacgta gtcggcacag cctggtcgcc ttccacctct gggagctgga   7560
gtccactggg gtggcctgac tcccccagtc cccttcccgt gacctggtca gggtgagccc   7620
atgtggagtc agcctcgcag gcctccctgc cagtagggtc cgagtgtgtt tcatccttcc   7680
cactctgtcg agcctggggg ctggagcgga gacgggaggc ctggcctgtc tcggaacctg   7740
tgagctgcac caggtagaac gccagggacc ccagaatcat gtgcgtcagt ccaaggggtc   7800
ccctccagga gtagtgaaga ctccagaaat gtccctttct tctcccccat cctacgagta   7860
attgcatttg cttttgtaat tcttaatgag caatatctgc tagagagttt agctgtaaca   7920
gttctttttg atcatctttt tttaataatt agaaacacca aaaaaatcca gaaacttgtt   7980
```

```
cttccaaagc agagagcatt ataatcacca gggccaaaag cttccctccc tgctgtcatt   8040
gcttcttctg aggcctgaat ccaaaagaaa aacagccata ggccctttca gtggccgggc   8100
tacccgtgag cccttcggag gaccagggct ggggcagcct ctgggcccac atccggggcc   8160
agctccggcg tgtgttcagt gttagcagtg ggtcatgatg ctctttccca cccagcctgg   8220
gataggggca gaggaggcga ggaggccgtt gccgctgatg tttggccgtg aacaggtggg   8280
tgtctgcgtg cgtccacgtg cgtgttttct gactgacatg aaatcgacgc ccgagttagc   8340
ctcacccggt gacctctagc cctgcccgga tggagcgggg cccacccggt tcagtgtttc   8400
tggggagctg gacagtggag tgcaaaaggc ttgcagaact tgaagcctgc tccttccctt   8460
gctaccacgg cctcctttcc gtttgatttg tcactgcttc aatcaataac agccgctcca   8520
gagtcagtag tcaatgaata tatgaccaaa tatcaccagg actgttactc aatgtgtgcc   8580
gagcccttgc ccatgctggg ctcccgtgta tctggacact gtaacgtgtg ctgtgtttgc   8640
tccccttccc cttccttctt tgccctttac ttgtctttct ggggtttttc tgtttgggtt   8700
tggtttggtt tttatttctc cttttgtgtt ccaaacatga ggttctctct actggtcctc   8760
ttaactgtgg tgttgaggct tatatttgtg taatttttgg tgggtgaaag gaattttgct   8820
aagtaaatct cttctgtgtt tgaactgaag tctgtattgt aactatgttt aaagtaattg   8880
ttccagagac aaatatttct agacactttt tctttacaaa caaaagcatt cggagggagg   8940
gggatggtga ctgagatgag aggggagagc tgaacagatg acccctgccc agatcagcca   9000
gaagccaccc aaagcagtgg agcccaggag tcccactcca agccagcaag ccgaatagct   9060
gatgtgttgc cactttccaa gtcactgcaa aaccaggttt tgttccgccc agtggattct   9120
tgttttgctt cccctccccc cgagattatt accaccatcc cgtgctttta aggaaaggca   9180
agattgatgt ttccttgagg ggagccagga ggggatgtgt gtgtgcagag ctgaagagct   9240
ggggagaatg gggctgggcc cacccaagca ggaggctggg acgctctgct gtgggcacag   9300
gtcaggctaa tgttggcaga tgcagctctt cctggacagg ccaggtggtg ggcattctct   9360
ctccaaggtg tgccccgtgg gcattactgt ttaagacact tccgtcacat cccaccccat   9420
cctccagggc tcaacactgt gacatctcta ttccccaccc tccccttccc agggcaataa   9480
aatgaccatg gagggggctt gcactctctt ggctgtcacc cgatcgccag caaaacttag   9540
atgtgagaaa accccttccc attccatggc gaaaacatct ccttagaaaa gccattaccc   9600
tcattaggca tggttttggg ctcccaaaac acctgacagc ccctccctcc tctgagaggc   9660
ggagagtgct gactgtagtg accattgcat gccgggtgca gcatctggaa gagctaggca   9720
gggtgtctgc cccctcctga gttgaagtca tgctcccctg tgccagccca gaggccgaga   9780
gctatggaca gcattgccag taacacaggc caccctgtgc agaagggagc tggctccagc   9840
ctggaaacct gtctgaggtt gggagaggtg cacttggggc acagggagag gccgggacac   9900
acttagctgg agatgtctct aaaagccctg tatcgtattc accttcagtt tttgtgtttt   9960
gggacaatta ctttagaaaa taagtaggtc gttttaaaaa caaaaattat tgattgcttt  10020
tttgtagtgt tcagaaaaaa ggttctttgt gtatagccaa atgactgaaa gcactgatat  10080
atttaaaaac aaaaggcaat ttattaagga aatttgtacc atttcagtaa acctgtctga  10140
atgtacctgt atacgtttca aaaacacccc ccccccactg aatccctgta acctatttat  10200
tatataaaga gtttgcctta taaattt                                       10227
```

<210> SEQ ID NO 29
<211> LENGTH: 10227
<212> TYPE: DNA

<213> ORGANISM: Homo sapiens

<400> SEQUENCE: 29

```
gggcgcgcgc gctccctcct ctcggagagg gctgtggtaa aagccgtccg gaaaatggcc     60
gccgccgccg ccgccgccga gcggaggagg aggaggaggc gaggaggaga gactgctcca    120
taaaaataca gactcaccag ttcctgcttt gatgtgacat gtgactcccc agaatacacc    180
ttgcttctgt agaccagctc caacaggatt ccatggtagc tgggatgtta gggctcaggg    240
aagaaaagtc agaagaccag gacctccagg gcctcaagga caaacccctc aagtttaaaa    300
aggtgaagaa agataagaaa gaagagaaag agggcaagca tgagcccgtg cagccatcag    360
cccaccactc tgctgagccc gcagaggcag gcaaagcaga gacatcagaa gggtcaggct    420
ccgcccccggc tgtgccggaa gcttctgcct cccccaaaca gcggcgctcc atcatccgtg    480
accggggacc catgtatgat gaccccaccc tgcctgaagg ctggacacgg aagcttaagc    540
aaaggaaatc tggccgctct gctgggaagt atgatgtgta tttgatcaat ccccagggaa    600
aagcctttcg ctctaaagtg gagttgattg cgtacttcga aaaggtaggc gacacatccc    660
tggaccctaa tgattttgac ttcacggtaa ctgggagagg gagcccctcc cggcgagagc    720
agaaaccacc taagaagccc aaatctccca aagctccagg aactggcaga ggccggggac    780
gccccaaagg gagcggcacc acgagaccca aggcggccac gtcagagggt gtgcaggtga    840
aaagggtcct ggagaaaagt cctgggaagc tccttgtcaa gatgcctttt caaacttcgc    900
caggggggcaa ggctgagggg ggtggggcca ccacatccac ccaggtcatg gtgatcaaac    960
gccccggcag gaagcgaaaa gctgaggccg accctcaggc cattcccaag aaacggggcc   1020
gaaagccggg gagtgtggtg gcagccgctg ccgccgaggc caaaaagaaa gccgtgaagg   1080
agtcttctat ccgatctgtg caggagaccg tactccccat caagaagcgc aagacccggg   1140
agacggtcag catcgaggtc aaggaagtgg tgaagcccct gctggtgtcc accctcggtg   1200
agaagagcgg gaaaggactg aagacctgta agagccctgg gcggaaaagc aaggagagca   1260
gccccaaggg gcgcagcagc agcgcctcct caccccccaa gaaggagcac caccaccatc   1320
accaccactc agagtcccca aaggcccccg tgccactgct cccacccctg cccccacctc   1380
cacctgagcc cgagagctcc gaggacccca ccagcccccc tgagccccag gacttgagca   1440
gcagcgtctg caaagaggag aagatgccca gaggaggctc actggagagc gacggctgcc   1500
ccaaggagcc agctaagact cagcccgcgg ttgccaccgc cgccacggcc gcagaaaagt   1560
acaaacaccg aggggaggga gagcgcaaag acattgtttc atcctccatg ccaaggccaa   1620
acagagagga gcctgtggac agccggacgc ccgtgaccga gagagttagc tgactttaca   1680
cggagcggat tgcaaagcaa accaacaaga ataaaggcag ctgttgtctc ttctccttat   1740
gggtagggct ctgacaaagc ttcccgatta actgaaataa aaaatatttt tttttctttc   1800
agtaaactta gagtttcgtg gcttcagggt gggagtagtt ggagcattgg ggatgttttt   1860
cttaccgaca agcacagtca ggttgaagac ctaaccaggg ccagaagtag ctttgcactt   1920
ttctaaacta ggctccttca acaaggcttg ctgcagatac tactgaccag acaagctgtt   1980
gaccaggcac ctcccctccc gcccaaacct ttcccccatg tggtcgttag agacagagcg   2040
acagagcagt tgagaggaca ctcccgtttt cggtgccatc agtgccccgt ctacagctcc   2100
cccagctccc cccacctccc ccactcccaa ccacgttggg acagggaggt gtgaggcagg   2160
agagacagtt ggattcttta gagaagatgg atatgaccag tggctatggc ctgtgcgatc   2220
ccacccgtgg tggctcaagt ctggccccac accagcccca atccaaaact ggcaaggacg   2280
```

```
cttcacagga caggaaagtg gcacctgtct gctccagctc tggcatggct aggagggggg   2340
agtcccttga actactgggt gtagactggc ctgaaccaca ggagaggatg gcccagggtg   2400
aggtggcatg gtccattctc aagggacgtc ctccaacggg tggcgctaga ggccatggag   2460
gcagtaggac aaggtgcagg caggctggcc tggggtcagg ccgggcagag cacagcgggg   2520
tgagagggat tcctaatcac tcagagcagt ctgtgactta gtggacaggg gagggggcaa   2580
agggggagga gaagaaaatg ttcttccagt tactttccaa ttctccttta gggacagctt   2640
agaattattt gcactattga gtcttcatgt tcccacttca aaacaaacag atgctctgag   2700
agcaaactgg cttgaattgg tgacatttag tccctcaagc caccagatgt gacagtgttg   2760
agaactacct ggatttgtat atatacctgc gcttgtttta aagtgggctc agcacatagg   2820
gttcccacga agctccgaaa ctctaagtgt ttgctgcaat tttataagga cttcctgatt   2880
ggtttctctt ctccccttcc atttctgcct tttgttcatt tcatcctttc acttctttcc   2940
cttcctccgt cctcctcctt cctagttcat cccttctctt ccaggcagcc gcggtgccca   3000
accacacttg tcggctccag tccccagaac tctgcctgcc ctttgtcctc ctgctgccag   3060
taccagcccc accctgtttt gagccctgag gaggccttgg gctctgctga gtccgacctg   3120
gcctgtctgt gaagagcaag agagcagcaa ggtcttgctc tcctaggtag ccccctcttc   3180
cctggtaaga aaaagcaaaa ggcatttccc accctgaaca acgagccttt tcacccttct   3240
actctagaga agtggactgg aggagctggg cccgatttgg tagttgagga aagcacagag   3300
gcctcctgtg gcctgccagt catcgagtgg cccaacaggg gctccatgcc agccgacctt   3360
gacctcactc agaagtccag agtctagcgt agtgcagcag ggcagtagcg gtaccaatgc   3420
agaactccca agacccgagc tgggaccagt acctgggtcc ccagcccttc ctctgctccc   3480
ccttttccct cggagttctt cttgaatggc aatgttttgc ttttgctcga tgcagacagg   3540
gggccagaac accacacatt tcactgtctg tctggtccat agctgtggtg taggggctta   3600
gaggcatggg cttgctgtgg gtttttaatt gatcagtttt catgtgggat cccatctttt   3660
taacctctgt tcaggaagtc cttatctagc tgcatatctt catcatattg gtatatcctt   3720
ttctgtgttt acagagatgt ctcttatatc taaatctgtc caactgagaa gtaccttatc   3780
aaagtagcaa atgagacagc agtcttatgc ttccagaaac acccacaggc atgtcccatg   3840
tgagctgctg ccatgaactg tcaagtgtgt gttgtcttgt gtatttcagt tattgtccct   3900
ggcttcctta ctatggtgta atcatgaagg agtgaaacat catagaaact gtctagcact   3960
tccttgccag tctttagtga tcaggaacca tagttgacag ttccaatcag tagcttaaga   4020
aaaaaccgtg tttgtctctt ctggaatggt tagaagtgag ggagtttgcc ccgttctgtt   4080
tgtagagtct catagttgga ctttctagca tatatgtgtc catttcctta tgctgtaaaa   4140
gcaagtcctg caaccaaact cccatcagcc caatccctga tccctgatcc cttccacctg   4200
ctctgctgat gacccccccca gcttcacttc tgactcttcc ccaggaaggg aagggggtc    4260
agaagagagg gtgagtcctc cagaactctt cctccaagga cagaaggctc ctgcccccat   4320
agtggcctcg aactcctggc actaccaaag gacacttatc cacgagagcg cagcatccga   4380
ccaggttgtc actgagaaga tgtttatttt ggtcagttgg gtttttatgt attatactta   4440
gtcaaatgta atgtggcttc tggaatcatt gtccagagct gcttccccgt cacctgggcg   4500
tcatctggtc ctggtaagag gagtgcgtgg cccaccaggc ccccctgtca cccatgacag   4560
ttcattcagg gccgatgggg cagtcgtggt tgggaacaca gcatttcaag cgtcacttta   4620
tttcattcgg gccccacctg cagctccctc aaagaggcag ttgcccagcc tctttccctt   4680
```

```
ccagtttatt ccagagctgc cagtggggcc tgaggctcct tagggttttc tctctatttc   4740
cccctttctt cctcattccc tcgtctttcc caaaggcatc acgagtcagt cgcctttcag   4800
caggcagcct tggcggttta tcgccctggc aggcaggggc cctgcagctc tcatgctgcc   4860
cctgccttgg ggtcaggttg acaggaggtt ggagggaaag ccttaagctg caggattctc   4920
accagctgtg tccggcccag ttttggggtg tgacctcaat ttcaattttg tctgtacttg   4980
aacattatga agatgggggc ctctttcagt gaatttgtga acagcagaat tgaccgacag   5040
ctttccagta cccatggggc taggtcatta aggccacatc cacagtctcc cccacccttg   5100
ttccagttgt tagttactac ctcctctcct gacaatactg tatgtcgtcg agctcccccc   5160
aggtctaccc ctcccggccc tgcctgctgg tgggcttgtc atagccagtg ggattgccgg   5220
tcttgacagc tcagtgagct ggagatactt ggtcacagcc aggcgctagc acagctccct   5280
tctgttgatg ctgtattccc atatcaaaag acacagggga cacccagaaa cgccacatcc   5340
cccaatccat cagtgccaaa ctagccaacg gccccagctt ctcagctcgc tggatggcgg   5400
aagctgctac tcgtgagcgc cagtgcgggt gcagacaatc ttctgttggg tggcatcatt   5460
ccaggcccga agcatgaaca gtgcacctgg gacagggagc agccccaaat tgtcacctgc   5520
ttctctgccc agcttttcat tgctgtgaca gtgatggcga aagagggtaa taaccagaca   5580
caaactgcca agttgggtgg agaaaggagt ttctttagct gacagaatct ctgaatttta   5640
aatcacttag taagcggctc aagcccagga gggagcagag ggatacgagc ggagtcccct   5700
gcgcgggacc atctggaatt ggtttagccc aagtggagcc tgacagccag aactctgtgt   5760
cccccgtcta accacagctc cttttccaga gcattccagt caggctctct gggctgactg   5820
ggccagggga ggttacaggt accagttctt taagaagatc tttgggcata tacattttta   5880
gcctgtgtca ttgccccaaa tggattcctg tttcaagttc acacctgcag attctaggac   5940
ctgtgtccta gacttcaggg agtcagctgt ttctagagtt cctaccatgg agtgggtctg   6000
gaggacctgc ccggtggggg ggcagagccc tgctccctcc gggtcttcct actcttctct   6060
ctgctctgac gggatttgtt gattctctcc attttggtgt ctttctcttt tagatattgt   6120
atcaatcttt agaaaaggca tagtctactt gttataaatc gttaggatac tgcctccccc   6180
agggtctaaa attacatatt agaggggaaa agctgaacac tgaagtcagt tctcaacaat   6240
ttagaaggaa aacctagaaa acatttggca gaaaattaca tttcgatgtt tttgaatgaa   6300
tacgagcaag cttttacaac agtgctgatc taaaaatact tagcacttgg cctgagatgc   6360
ctggtgagca ttacaggcaa ggggaatctg gaggtagccg acctgaggac atggcttctg   6420
aacctgtctt ttgggagtgg tatggaaggt ggagcgttca ccagtgacct ggaaggccca   6480
gcaccaccct ccttcccact cttctcatct tgacagagcc tgccccagcg ctgacgtgtc   6540
aggaaaacac ccagggaact aggaaggcac ttctgcctga ggggcagcct gccttgccca   6600
ctcctgctct gctcgcctcg gatcagctga gccttctgag ctggcctctc actgcctccc   6660
caaggccccc tgcctgccct gtcaggaggc agaaggaagc aggtgtgagg gcagtgcaag   6720
gagggagcac aacccccagc tcccgctccg ggctccgact tgtgcacagg cagagcccag   6780
accctggagg aaatcctacc tttgaattca agaacatttg ggaatttgg aaatctcttt   6840
gcccccaaac ccccattctg tcctaccttt aatcaggtcc tgctcagcag tgagagcaga   6900
tgaggtgaaa aggccaagag gtttggctcc tgcccactga tagcccctct ccccgcagtg   6960
tttgtgtgtc aagtggcaaa gctgttcttc ctggtgaccc tgattatatc cagtaacaca   7020
tagactgtgc gcataggcct gctttgtctc ctctatcctg ggcttttgtt ttgcttttta   7080
```

-continued

```
gttttgcttt tagtttttct gtccctttta tttaacgcac cgactagaca cacaaagcag   7140
ttgaattttt atatatatat ctgtatattg cacaattata aactcatttt gcttgtggct   7200
ccacacacac aaaaaaagac ctgttaaaat tatacctgtt gcttaattac aatatttctg   7260
ataaccatag cataggacaa gggaaaataa aaaaagaaaa aaaagaaaaa aaaacgacaa   7320
atctgtctgc tggtcacttc ttctgtccaa gcagattcgt ggtcttttcc tcgcttcttt   7380
caagggcttt cctgtgccag gtgaaggagg ctccaggcag cacccaggtt ttgcactctt   7440
gtttctcccg tgcttgtgaa agaggtccca aggttctggg tgcaggagcg ctcccttgac   7500
ctgctgaagt ccggaacgta gtcggcacag cctggtcgcc ttccacctct gggagctgga   7560
gtccactggg gtggcctgac tcccccagtc cccttcccgt gacctggtca gggtgagccc   7620
atgtggagtc agcctcgcag gcctccctgc cagtagggtc cgagtgtgtt tcatccttcc   7680
cactctgtcg agcctggggg ctggagcgga gacgggaggc ctggcctgtc tcggaacctg   7740
tgagctgcac caggtagaac gccagggacc ccagaatcat gtgcgtcagt ccaaggggtc   7800
ccctccagga gtagtgaaga ctccagaaat gtccctttct tctcccccat cctacgagta   7860
attgcatttg cttttgtaat tcttaatgag caatatctgc tagagagttt agctgtaaca   7920
gttctttttg atcatctttt tttaataatt agaaacacca aaaaaatcca gaaacttgtt   7980
cttccaaagc agagagcatt ataatcacca gggccaaaag cttccctccc tgctgtcatt   8040
gcttcttctg aggcctgaat ccaaaagaaa aacagccata ggccctttca gtggccgggc   8100
tacccgtgag cccttcggag gaccagggct ggggcagcct ctgggcccac atccggggcc   8160
agctccggcg tgtgttcagt gttagcagtg ggtcatgatg ctctttccca cccagcctgg   8220
gataggggca gaggaggcga ggaggccgtt gccgctgatg tttggccgtg aacaggtggg   8280
tgtctgcgtg cgtccacgtg cgtgttttct gactgacatg aaatcgacgc ccgagttagc   8340
ctcacccggt gacctctagc cctgcccgga tggagcgggg cccacccggt tcagtgtttc   8400
tggggagctg gacagtggag tgcaaaaggc ttgcagaact tgaagcctgc tccttccctt   8460
gctaccacgg cctcctttcc gtttgatttg tcactgcttc aatcaataac agccgctcca   8520
gagtcagtag tcaatgaata tatgaccaaa tatcaccagg actgttactc aatgtgtgcc   8580
gagcccttgc ccatgctggg ctcccgtgta tctggacact gtaacgtgtg ctgtgtttgc   8640
tccccttccc cttccttctt tgccctttac ttgtctttct ggggtttttc tgtttgggtt   8700
tggtttggtt tttatttctc cttttgtgtt ccaaacatga ggttctctct actggtcctc   8760
ttaactgtgg tgttgaggct tatatttgtg taatttttgg tgggtgaaag gaattttgct   8820
aagtaaatct cttctgtgtt tgaactgaag tctgtattgt aactatgttt aaagtaattg   8880
ttccagagac aaatatttct agacactttt tctttacaaa caaaagcatt cggagggagg   8940
gggatggtga ctgagatgag aggggagagc tgaacagatg acccctgccc agatcagcca   9000
gaagccaccc aaagcagtgg agcccaggag tcccactcca agccagcaag ccgaatagct   9060
gatgtgttgc cactttccaa gtcactgcaa aaccaggttt tgttccgccc agtggattct   9120
tgttttgctt cccctccccc cgagattatt accaccatcc cgtgctttta aggaaaggca   9180
agattgatgt ttccttgagg ggagccagga ggggatgtgt gtgtgcagag ctgaagagct   9240
ggggagaatg gggctgggcc cacccaagca ggaggctggg acgctctgct gtgggcacag   9300
gtcaggctaa tgttggcaga tgcagctctt cctggacagg ccaggtggtg ggcattctct   9360
ctccaaggtg tgccccgtgg gcattactgt ttaagacact tccgtcacat cccaccccat   9420
cctccagggc tcaacactgt gacatctcta ttccccaccc tccccttccc agggcaataa   9480
```

-continued

```
aatgaccatg gagggggctt gcactctctt ggctgtcacc cgatcgccag caaaacttag    9540

atgtgagaaa accccttccc attccatggc gaaaacatct ccttagaaaa gccattaccc    9600

tcattaggca tggttttggg ctcccaaaac acctgacagc ccctccctcc tctgagaggc    9660

ggagagtgct gactgtagtg accattgcat gccgggtgca gcatctggaa gagctaggca    9720

gggtgtctgc cccctcctga gttgaagtca tgctcccctg tgccagccca gaggccgaga    9780

gctatggaca gcattgccag taacacaggc caccctgtgc agaagggagc tggctccagc    9840

ctggaaacct gtctgaggtt gggagaggtg cacttggggc acagggagag gccgggacac    9900

acttagctgg agatgtctct aaaagccctg tatcgtattc accttcagtt tttgtgtttt    9960

gggacaatta ctttagaaaa taagtaggtc gttttaaaaa caaaaattat tgattgcttt   10020

tttgtagtgt tcagaaaaaa ggttctttgt gtatagccaa atgactgaaa gcactgatat   10080

atttaaaaac aaaaggcaat ttattaagga aatttgtacc atttcagtaa acctgtctga   10140

atgtacctgt atacgtttca aaaacacccc ccccccactg aatccctgta acctatttat   10200

tatataaaga gtttgcctta taaattt                                       10227
```

MECP2E1 GENE

RELATED APPLICATIONS

This application is a continuation-in-part of U.S. application Ser. No. 11/352,153, filed Feb. 9, 2006, now U.S. Pat. No. 7,670,773, issued Mar. 2, 2012, which is a continuation of International Application No. PCT/CA2005/000198 which designated the United States and was filed on Feb. 17, 2005, published in English, which claims the benefit of U.S. Provisional Application No. 60/544,311, filed on Feb. 17, 2004. The entire teachings of the above applications are incorporated herein by reference.

BACKGROUND OF THE INVENTION

Neuropsychiatric disorders account for six of the ten highest impact diseases worldwide, according to the World Health Organization. Cost to the US economy is $100 billion—one of every four persons entering physician offices has a diagnosable mental disorder.

Rett syndrome (RTT) (OMIM #312750) is characterized by onset, in girls, of a gradual slowing of neurodevelopment in the second half of the first year of life towards stagnation by age four, followed by regression and loss of acquired fine motor and communication skills. A pseudostationary period follows during which a picture of preserved ambulation, aberrant communication and stereotypic hand wringing approximates early autism. Regression, however, remains insidiously ongoing and ultimately results in profound mental retardation.

Up to 80% of patients with RTT have mutations in exons 3 and 4 of the 4-exon MECP2 gene (FIG. 1*a*) encoding the MeCP2 transcriptional repressor. Mutations in the remaining 20% of patients has remained elusive. In the known transcript of the gene all four exons are utilized, the translation start site is in exon 2, and exon 1 and most of exon 2 form the 5' untranslated region (UTR). For clarity, this transcript is named MECP2E2 (previously MECP2A), and its encoded protein MeCP2E2 (previously MeCP2A).

No mutation specific to the MeCP2E2-defining exon 2 has been found to date despite several hundred patients analyzed for mutations in this exon. These studies did not include exon 1 as it was considered non-coding.

Non-inactivating MECP2 mutations have also been associated with phenotypes that overlap RTT such as mental retardation and autism. There is a need for the identification of further mutations to account for the remaining 20% of RTT patients so that methods of diagnosing and treating RTT can be identified.

Mutations in the Rett syndrome gene, MECP2, have also been found among autism patients as well as in patients with childhood onset psychosis, Angelman syndrome, non-syndromic mental retardation and neo-natal encepalopathy, demonstrating that there may be diverse phenotypic consequences of mutations in MECP2.

SUMMARY OF THE INVENTION

The present inventors have identified a novel open reading frame of the MECP2 gene, that is called MECP2E1. Inspection of the 5'UTR revealed that, whereas exon 2 has a number of in-frame stops upstream of the ATG, exon 1 contains an open reading frame across its entire length including an ATG. This open reading frame encodes a transcript composed of exons 1, 3 and 4 of the MECP2 gene. MECP2E1 is similar to MECP2E2 (GenBank accession # NM_004992, (SEQ ID NO. 1) except with nucleotides 71-193 absent, corresponding to the splicing out of exon 2.

Accordingly, the present invention provides an isolated nucleic acid molecule comprising a sequence encoding the MeCP2E1 protein. The invention also includes the corresponding polypeptide, MeCP2E1.

In one embodiment, the purified and isolated nucleic acid molecule comprises (a) a nucleic acid sequence encoding a protein as shown in SEQ ID No. 4;

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, an isolated nucleic acid molecule is provided having a sequence as shown in SEQ ID No. 3 or a fragment or variant thereof.

The inventors have found that patients with a neuropsychiatric disorder or developmental disorder such as Rett's syndrome and mental retardation, had mutations in exon 1 of the MECP2E1 gene. Accordingly, the present invention provides a method of detecting a neuropsychiatric disorder or developmental disorder comprising detecting a mutation or deletion in exon 1 of the MECP2E1 sequence (SEQ ID No. 3). A mutation can be detected by sequencing PCR products from genomic DNA using primers X1F/X1R: mutation screening primers (FIG. 1). Detection of instertion or deletion mutations may require the cloning of the PCR product into a suitable plasmid vector, followed by transfection into *E. Coli*, and sequencing of clones from isolated colonies. Alternatively, a mutation can be detected by multiple ligation-dependent probe amplification (MLPA) using 20 probe pairs that target the four MECP2 exons, six X-linked control regions and ten autosomal control regions. A mutation or deletion can also be detected by assaying for the protein product encoded by MECP2E1.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawings will be provided by the Office upon request and payment of the necessary fee.

The invention will now be described in relation to the drawings in which:

FIG. 1 shows MECP2 5' splice variants. a) Structure of the MECP2 gene. Numbered boxes indicate exons; asterisks indicate in-frame stop codons. In the traditional MECP2E2 splice variant, the start codon is in exon 2. In MECP2E1, exon 2 is not present and the start codon is in exon 1. HF/HR1 and MF/MR: human and mouse primer pairs used in the rtPCR experiments shown in panel c. HR2: a second human reverse primer, which confirms the results obtained with HR1 (data not shown). X1F/X1R: mutation screening primers (see FIG. 2). Primer sequences (5'-3'): HF-ctcggagagagggctgtg (SEQ ID No. 5), HR1-cttgaggggtttgtccttga (SEQ ID No. 6), HR2-cgtttgatcaccatgacctg (SEQ ID No. 7), MF-aggaggcgaggaggagagac (SEQ ID No. 8), MR-ctggctctgcagaatggtg (SEQ ID No. 9), X1F-ccatcacagccaatgacg (SEQ ID No. 19), X1R-agggggagggtagagaggag (SEQ ID No. 20). b) Examples of MECP2 ESTs. c) PCR results using primers in (a) (HF/HR1 and MF/MR) on cDNA from indicated adult tissues (except where indicated otherwise) and cell cultures; d.p.c.: days postcoitum. d) Transcript-specific real-time quantitative PCR (SYBR Green detection method) on cDNA from indicated tissues or cell cultures. e) 3' myc-tagged MeCP2E1 (and MeCP2E2) localize principally in the nucleus, and in indeterminate puncti in the cytoplasm. f) N-termini of indicated proteins; dashes represent no amino acids.

DETAILED DESCRIPTION OF THE INVENTION

Figure 2:
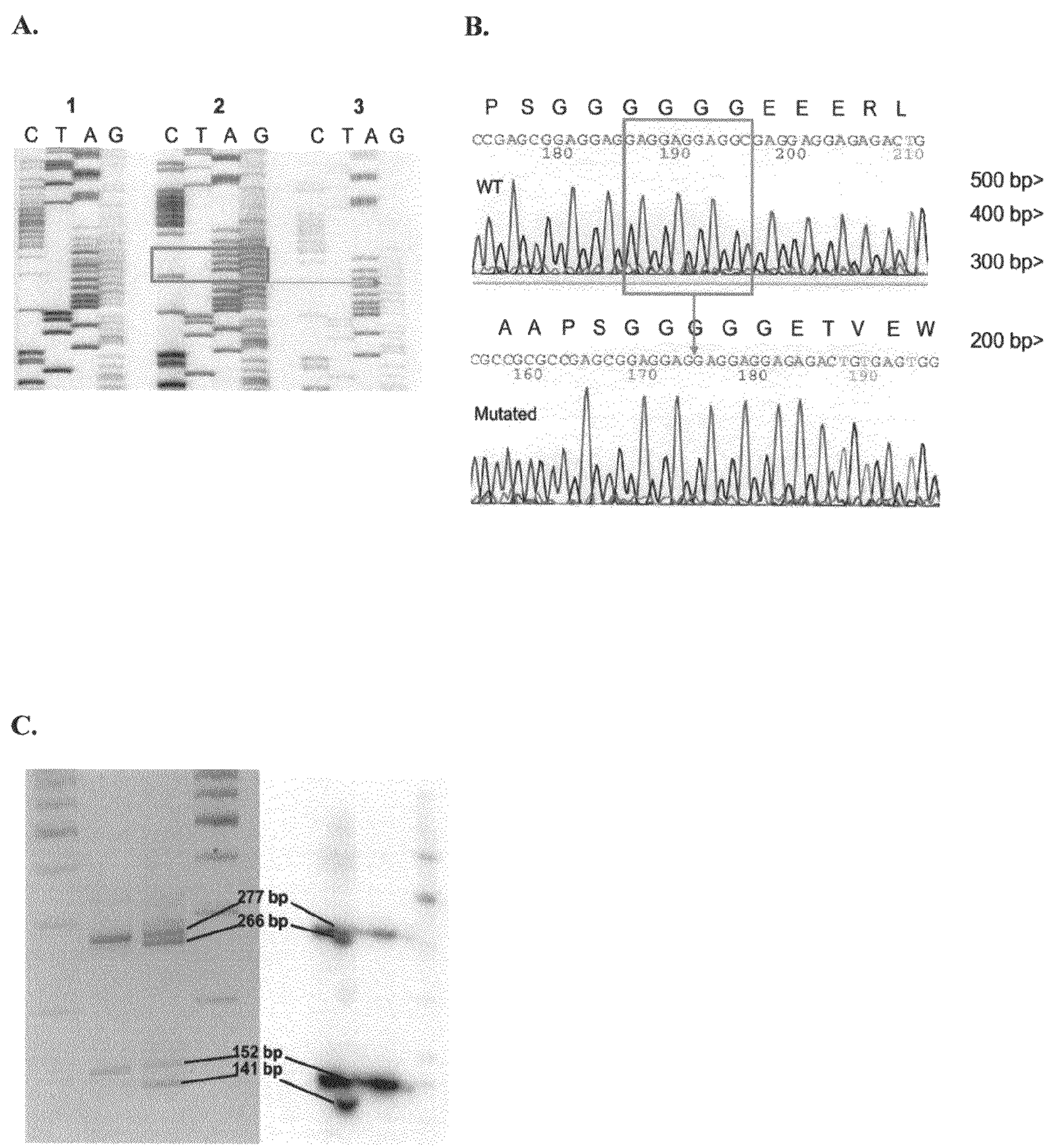
FIG. 2 shows a deletion mutation in patient V1.a1) Sequence of PCR product from genomic DNA using primers X1F/X1R (FIG. 1*a*). Note mixed sequence. a2) and a3) Sequences of clones of the patient's wild-type and mutant alleles respectively; red box indicating the 11 nucleotides deleted in the mutated allele. b) Electropherograms of the same cloned wild-type and deleted alleles. c) PCR on indicated cDNAs using primers HF/HR1 (FIG. 1*a,c*). Lanes 1 and 2 (on 2.5% high resolution agarose) are from control and patient whole blood respectively. Lanes 3 to 8 (on 6% denaturing polyacrylamide) are from control blood (3), patient blood (4), control fetal brain (5), control adult brain (6), control testis (7) and control genomic DNA (8). Note that expression of the patient's MECP2E2 transcript with the 11 bp exon 1 deletion (band at 266 bp) is not diminished compared to the non-deleted allele (277 bp). The 141 and 152 bp bands are the deleted and non-deleted MECP2E1 transcripts respectively.

The present inventors have identified a MECP2 splice variant that contributes to new coding sequence that may contain mutations in patients with neuropsychiatric disorders such as Rett's syndrome and mental retardation.

I. Nucleic Acid Molecules of the Invention

As hereinbefore mentioned, the present invention relates to isolated MECP2E1 nucleic acid molecules. The term "isolated" refers to a nucleic acid substantially free of cellular material or culture medium when produced by recombinant DNA techniques, or chemical precursors, or other chemicals when chemically synthesized.

The term "nucleic acid" is intended to include DNA and RNA and can be either double stranded or single stranded. The term is also intended to include a strand that is a mixture of nucleic acid molecules and nucleic acid analogs and/or nucleotide analogs, or that is made entirely of nucleic acid analogs and/or nucleotide analogs.

Broadly stated, the present invention provides an isolated nucleic acid molecule containing a sequence encoding the MECP2E1 transcript of the MECP2 gene. Accordingly, the present invention provides an isolated nucleic acid molecule containing a sequence encoding MECP2E1 shown in SEQ ID No. 4 or a fragment, variant, or analog thereof.

In one embodiment, the purified and isolated nucleic acid molecule comprises (a) a nucleic acid sequence encoding a MECP2E1 protein as shown in SEQ ID No. 4;

(b) a nucleic acid sequence complementary to (a);

(c) a nucleic acid sequence that has substantial homology to (a) or (b);

(d) a nucleic acid sequence that is an analog to a nucleic acid sequence of (a), (b), or (c);

(e) a fragment of (a) to (d) that is at least 15 bases, preferably 20 to 30 bases, and which will hybridize to a nucleic acid sequence of (a), (b), (c) or (d) under stringent hybridization conditions; or (f) a nucleic acid molecule differing from any of the nucleic acids of (a) to (c) in codon sequences due to the degeneracy of the genetic code.

In a specific embodiment of the invention, the isolated nucleic acid molecule has a sequence as shown in SEQ ID No. 3 or a fragment or variant thereof.

The term "MECP2E1" means an isoform of the MECP2 gene that contains exons 1, 3 and 4 but lacks exon 2. This gene was previously referred to as MECP2B but is now called MECP2E1 indicating the translation start site in exon one. The term "MECP2E1" includes the nucleic acid sequence as shown in SEQ ID No. 3 as well as mutations, variants and fragments thereof that are associated with neuropsychiatric disorders and developmental disorders. MECP2E1" can also be referred to as "MECP2_e1." The "MeCP2E1" protein can also be referred to as "MeCP2_e1." MECP2E2 is the transcript of the gene that contains exons 1, 2, 3 and 4. "MECP2E2" can also be referred to as "MECP2_e2." The "MeCP2E2" protein can also be referred to as "MeCP2_e2."

The term "MECP2E1" means an isoform of the MECP2 gene that contains exons 1, 3 and 4 but lacks exon 2. This gene was previously referred to as MECP2B but is now called MECP2E1 indicating the translation start site in exon one.

Figure 6:
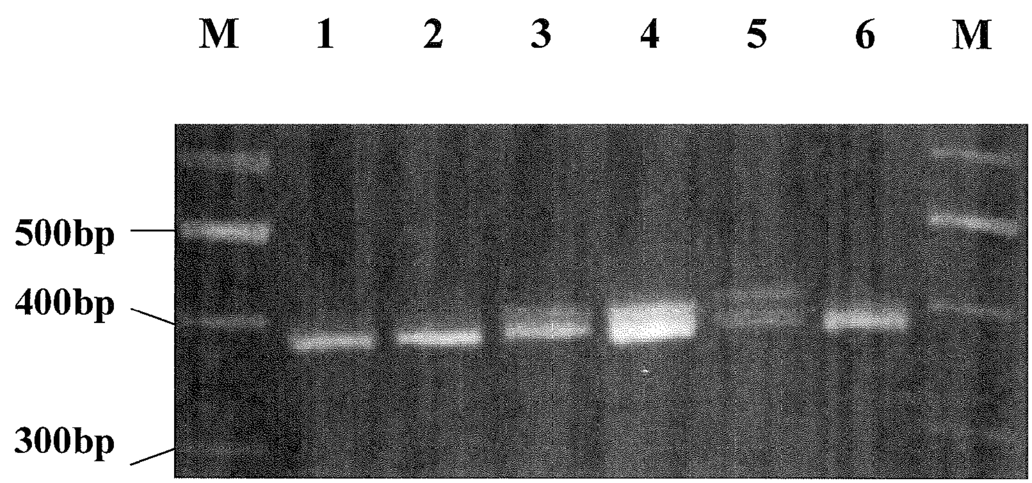
FIG. 6 shows a high resolution agarose gel (2.2%) of PCR product for MECP2 exon 1 for negative controls (Lanes 1 and 2), 3 bp insertion (Lanes 3 and 4), 9 bp insertion (Lane 5) and 2 bp deletion (Lane 6). Size ladder (M) 100 bp ladder (MBI Fermentas), flanks the PCR lanes.

The term "MECP2E1" includes the nucleic acid sequence as shown in FIG. 6(*a*) (SEQ ID No. 3) as well as mutations, variants and fragments thereof that are associated with neuropsychiatric disorders and developmental disorders. "MECP2E1" can also be referred to as "MECP2_e1." The "MeCP2E1" protein can also be referred to as "MeCP2_e1." MECP2E2 is the transcript of the gene that contains exons 1, 2, 3 and 4. "MECP2E2" can also be referred to as "MECP2_e2." The "MeCP2E2" protein can also be referred to as "MeCP2e2."

It will be appreciated that the invention includes nucleic acid molecules encoding truncations of the MeCP2E1 proteins of the invention, and analogs and homologs of the MeCP2E1 proteins of the invention and truncations thereof, as described below.

Further, it will be appreciated that the invention includes nucleic acid molecules comprising nucleic acid sequences having substantial sequence homology with the nucleic acid sequences of the invention and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80-90% identity with the nucleic acid sequences of the invention.

Sequence identity is most preferably assessed by the algorithm of the BLAST version 2.1 program advanced search (BLAST is a series of programs that are available online at www.ncbi.nlm.nih.gov/BLAST. The advanced blast search (1 www.ncbi.nlm.nih.gov/blast/blast.cgi?Jform=1) is set to default parameters. (i.e. Matrix BLOSUM62; Gap existence cost 11; Per residue gap cost 1; Lambda ratio 0.85 default).). For example, if a nucleotide sequence (called "Sequence A") has 90% identity to a portion of the nucleotide sequence in SEQ ID No. 3, then Sequence A will be identical to the referenced portion of the nucleotide sequence in SEQ ID No. 3, except that Sequence A may include up to 10 point mutations, such as substitutions with other nucleotides, per each 100 nucleotides of the referenced portion of the nucleotide sequence in SEQ ID No. 3. Nucleotide sequences functionally equivalent to the MECP2E1 transcript can occur in a variety of forms as described below.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence shown in SEQ ID No. 3, with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule shown in SEQ ID No. 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Another aspect of the invention provides a nucleic acid molecule, and fragments thereof having at least 15 bases, which hybridizes to the nucleic acid molecules of the invention under hybridization conditions. Such nucleic acid molecules preferably hybridize to all or a portion of MECP2E1 or its complement under stringent conditions as defined herein (see Sambrook et al. (most recent edition) Molecular Cloning: A Laboratory Manual, Cold Spring Harbor Laboratory Press, Cold Spring Harbor, N.Y.; Ausubel et al. (eds.), 1995, Current Protocols in Molecular Biology, (John Wiley & Sons, NY)). The portion of the hybridizing nucleic acids is typically at least 15 (e.g. 20, 25, 30 or 50) nucleotides in length. The hybridizing portion of the hybridizing nucleic acid is at least 80% e.g. at least 95% or at least 98% identical to the sequence or a portion or all of a nucleic acid encoding a MeCP2E1 polypeptide, or its complement. Hybridizing nucleic acids of the type described herein can be used, for example, as a cloning probe, a primer (e.g. a PCR primer) or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g. SSC or SSPE). Then, assuming that 1% mismatching results in a 1 degree Celsius decrease in the Tm, the temperature of the final wash in the hybridization reaction is reduced accordingly (for example, if sequences having greater than 95% identity with the probe are sought, the final wash temperature is decreased by 5 degrees Celsius). In practice, the change in Tm can be between 0.5 degrees Celsius and 1.5 degrees Celsius per 1% mismatch. Low stringency conditions involve hybridizing at about: 1×SSC, 0.1% SDS at 50° C. High stringency conditions are: 0.1×SSC, 0.1% SDS at 65° C. Moderate stringency is about 1×SSC 0.1% SDS at 60 degrees Celsius. The parameters of salt concentration and temperature can be varied to achieve the optimal level of identity between the probe and the target nucleic acid.

Isolated and purified nucleic acid molecules having sequences which differ from the nucleic acid sequence shown in SEQ ID No. 3 due to degeneracy in the genetic code are also within the scope of the invention. The genetic code is degenerate so other nucleic acid molecules, which encode a polypeptide identical to the MeCP2E1 amino acid sequence (SEQ ID No. 4) may also be used.

The present invention also includes mutated forms of MEC2P2E1 associated with a neuropsychiatric disorder or developmental disorder including the specific mutations listed in Table 1. Specifically, the following mutations are associated with Rett's syndrome: (1) an 11 bp deletion in nucleotides 38 to 54 shown in SEQ ID No. 1; (2) a deletion of exon 1 containing nucleotides 1-69 shown in SEQ ID No. 1; (3) a adenosine to threonine change at nucleotide position 8 shown in SEQ ID No. 1; and (4) a deletion in the sequence TG at nucleotide positions 70-71 in SEQ ID No. 1 (5) an adenine to guanine change at nucleotide position 8 shown in SEQ ID No. 1; (6) a cytosine to thymine change at nucleotide position 12 shown in SEQ ID No. 1; and (7) a deletion in the sequence TG at nucleotide positions 69 and 70 in SEQ ID No. 1.

The following mutations are associated with developmental delay: (1) an insertion of one or more copies of the trinucleotide sequence GCC between nucleotides 11 and 29 shown in SEQ ID No. 1; (2) a deletion of one or more copies of the trinucleotide sequence GCC between nucleotides 11 and 29 shown in SEQ ID No. 1; (3) an insertion of the nucleotide sequence GGA between nucleotides 38 and 54 shown in SEQ ID No. 1; (4) a deletion of the nucleotide sequence GC at nucleotides −38 and −39 upstream of nucleotide 1 shown in SEQ ID No. 1; and (5) a deletion of the nucleotide sequence AG at nucleotides −19 and −20 upstream of nucleotide 1 shown in SEQ ID No. 1.

With respect to mutations (4) and (5) in the developmental delay group, these are upstream of nucleotide 1 shown in SEQ ID No. 1 GenBank Accession number BX538060 has the upstream sequences. Therefore, for greater clarity mutation (4), that consists of a deletion of the nucleotide sequence GC at nucleotides −38 and −39, corresponds to nucleotides 11-12 of sequence BX538060; and mutation (5), that consists of a deletion of the nucleotide sequence AG at nucleotides −19 and −20, corresponds to nucleotides 30-31 of BX538060.

Nucleic acid molecules from MECP2E1 can be isolated by preparing a labeled nucleic acid probe based on all or part of the nucleic acid sequences as shown in SEQ ID No. 3, and using this labelled nucleic acid probe to screen an appropriate DNA library (e.g. a cDNA or genomic DNA library). Nucleic acids isolated by screening of a cDNA or genomic DNA library can be sequenced by standard techniques. Another method involves comparing the MECP2E1 sequence to other sequences, for example using bioinformatics techniques such as database searches or alignment strategies, and detecting the presence of a MECP2E1 nucleic acid sequence.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in SEQ ID No. 3 for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the MeCP2E1 protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in SEQ ID No. 3 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated MeCP2E1 protein encoded by the nucleic acid molecules of the invention. Within the context of the present invention, a protein of the invention may include various structural forms of the primary protein which retain biological activity.

Broadly stated, the present invention provides an isolated protein encoded by exon 1, 3 and 4 of the MECP2 gene.

In a preferred embodiment of the invention, the MeCP2E1 protein has the amino acid sequence as shown in SEQ ID No. 4 or a fragment or variant thereof.

The invention also includes mutated forms of the MeCP2E1 protein that are associated with a neuropsychiatric disorder or developmental disorder. Specifically, the invention includes the mutations in MECP2E1 described in Table 1.

In addition to full length amino acid sequences, the proteins of the present invention also include truncations of the protein, and analogs, and homologs of the protein and truncations thereof as described herein. Truncated proteins may comprise peptides of at least fifteen amino acid residues.

Analogs or variants of the protein having the amino acid sequence shown in SEQ ID No. 4 and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequence shown in SEQ ID No. 4. Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ ID No. 4. The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence having the exon 1 region shown in SEQ ID No. 4 and/or truncations thereof as described herein.

A homologous protein includes a protein with an amino acid sequence having at least 70%, preferably 80-90% identity with the amino acid sequence as shown in SEQ ID No. 4 and includes the exon 1 region characteristic of the MeCP2E1 protein. As with the nucleic acid molecules of the invention, identity is calculated according to methods known in the art. Sequence identity is most preferably assessed by the algorithm of BLAST version 2.1 advanced search. BLAST is a series of programs that are available online at www.ncbi.nlm.nih.gov/BLAST. The advanced BLAST search (www.ncbi.nlm.nih.gov/blast/blast.cgi?Jform=1) is set to default parameters (i.e. Matrix BLOSUM62, Gap existence cost 11; Per residue gap cost 1; Lambda ration 0.85 default).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner which allows for expression, by transcription of the DNA molecule, of an RNA molecule which is antisense to a nucleotide sequence comprising the nucleotides as shown SEQ ID No. 3. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Applications

A. Diagnostic Applications

As previously mentioned, the present inventors have isolated a novel splice variant of the MECP2 gene, MECP2E1, and have shown that exon 1 is deleted or mutated in people with neuropsychiatric disorders or developmental disorders such as Rett's syndrome or mental retardation. As a result, the present invention also includes a method of detecting a neuropsychiatric or developmental disorder by detecting a mutation or deletion in the MECP2E1 nucleic acid or MeCP2E1 protein.

The term "neuropsychiatric disorder" as used herein includes, but is not limited to, autism/autism spectrum disorder, epilepsy, Angelman syndrome, Prader-Willi syndrome, encephalopathy, schizophrenia, bipolar affective disorder, depression, obsessive compulsive disorder, panic disorder, attention deficit hyperactivity disorder, and ataxia.

The term "developmental disorder" includes but is not limited to, mental retardation.

i) Detecting Mutations in the Nucleic Acid Sequence

In one embodiment, the present invention provides a method for detecting a neuropsychiatric or developmental disorder comprising detecting a deletion or mutation in exon 1 of the MECP2 gene in a sample obtained from an animal, preferably a mammal, more preferably a human.

The Examples and Table 1 summarize some of the mutations found in MECP2E1 in patient's with Rett's syndrome or developmental delay. (They are also described in Section I). Screening assays can be developed for each of the mutations. Examples of methods that can be used to detect mutations include sequencing, polymerase chain reaction, reverse transcription-polymerase chain reaction, denaturing HPLC, electrophoretic mobility, nucleic acid hybridization, fluorescent in situ hybridization and multiplex ligation-dependent probe amplification. Details of screening assays that may be employed are provided in Examples 3, 4 or 5.

Rett's syndrome has been shown to be caused by deletions in exon 1 of MECP2. Patients homozygous for these deletions can be detected by PCR-amplifying and sequencing exon 1 and flanking sequences using X1F/X1R primers. Consequently, the present invention includes a method for determining a deletion in exon 1 of the MECP2 gene by a method comprising:

(a) amplifying the nucleic acid sequences in the sample with primers X1F (5'-CCATCACAGCCAATGACG-3') (SEQ ID No. 19) and X1R (5'-AGGGGGAGGGTAGAGAGGAG-3') (SEQ ID No. 20) in a polymerase chain reaction;

(b) amplifying the nucleic acid sequences from a control with same primers;

(c) sequencing the amplified sequences; and (d) comparing the sample sequences to the control sequences wherein deletion of nucleotides in the sample sequence compared to the control sequence indicates that the sample is from an animal with Rett's syndrome.

Additional exon 1 mutations not detectable by the PCR reaction, can be identified using multiplex ligation-dependent probe amplification (MLPA) in all four exons. MLPA analysis is described in reference 5 and in Schouten, U.S. application Ser. No. 10/218,567, (publication number 2003/0108913) which are incorporated herein in by reference. Accordingly, the present invention includes a method for determining a deletion in exon 1 of the MECP2 gene by performing MLPA analysis with 20 probe pairs that target the four MECP2 exons, six X-linked control regions and ten autosomal control regions.

One skilled in the art will appreciate that other methods, in addition to the ones discussed above and in the examples, can be used to detect mutations in exon 1 of the MECP2 gene. For example, in order to isolate nucleic acids from a sample, one can prepare nucleotide probes from the nucleic acid sequences of the invention. In addition, the nucleic acid probes described herein (for example, see FIG. 1) can also be used. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Accordingly, the present invention also relates to a method of detecting the presence of a nucleic acid molecule containing exon 1 of the MECP2 gene in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes.

Hybridization conditions which may be used in the methods of the invention are known in the art and are described for example in Sambrook J, Fritch E F, Maniatis T. In: Molecular Cloning, A Laboratory Manual, 1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

Prior to hybridizing a sample with DNA probes, the sample can be treated with primers that flank the MECP2 gene in order to amplify the nucleic acid sequences in the sample. The primers used may be the ones described in the present application. For example, primers specific for human MECP2 include HF (ctcggagagagggctgtg) (SEQ ID No. 5), HR1 (cttgaggggtttgtccttga) (SEQ ID No. 6), HR2 (cgtttgatcaccatgacctg) (SEQ ID No. 7). Primers for mouse MECP2 include MF (aggaggcgaggaggagagac) (SEQ ID NO. 8) and MR (ctggctctgcagaatggtg) (SEQ ID No. 9). In addition, the sequence of the MECP2 gene provided herein also permits the identification and isolation, or synthesis of new nucleotide sequences which may be used as primers to amplify a nucleic acid molecule of the invention. The primers may be used to amplify the genomic DNA of other species. The PCR amplified sequences can be examined to determine the relationship between the genes of various species.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl chloride, fluorescein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain noncomplementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule of the invention is provided comprising treating the sample with primers which are capable of amplifying the nucleic acid molecule or a predetermined oligonucleotide fragment thereof in a polymerase chain reaction to form amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis et al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp 3-12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UV) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp 3-12, Academic Press 1989, which is incorporated herein by reference. Preferably, the PCR utilizes polymerase obtained from the thermophilic bacterium *Thermus aquatics* (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol. 1(1), page 5, and European Published Application No. 0320308, published Jun. 14, 1989, and U.S. Pat. No. 5,130,238 to Malek).

(ii) Detecting the MeCP2E1 Protein

In another embodiment, the present invention provides a method for detecting a neuropsychiatric or developmental disorder comprising detecting a deletion or mutation in the MeCP2E1 protein in a sample from an animal.

The MeCP2E1 protein of the present invention may be detected in a biological sample using antibodies that are specific for MeCP2E1 using various immunoassays that are discussed below.

Conventional methods can be used to prepare the antibodies. For example, by using a peptide from the MeCP2E1 protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein of the invention, or peptide thereof. Antibodies can be fragmented using conventional techniques and the fragments screened for utility in the same manner as described above. For example, $F(ab')_2$ fragments can be generated by treating antibody with pepsin. The resulting $F(ab')_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CipA protein (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, V11 regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S-35, Cu-64, Ga-67, Zr-89, Ru-97, Tc-99m, Rh-105, Pd-109, In-111, I-123, I-125, I131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immunoprecipitation, latex agglutination, hemagglutination, and histochemical tests. Thus, the antibodies may be used to identify or quantify the amount of a protein of the invention in a sample in order to diagnose the presence of Rett's syndrome.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of MeCP2E1 can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of MeCP2E1 can be determined by measuring the amount of antibody bound to the protein using substances that interact specifically with the antibody to cause agglutination or precipitation. In particular, labelled antibody against an antibody specific for a protein of the invention, can be added to the reaction mixture. The presence of a protein of the invention can be determined by a suitable method from among the already described techniques depending on the type of labelling agent. The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention the kit includes antibodies of the invention and reagents required for binding of the antibody to a protein of the invention in a sample.

The kits may include nucleic acid molecules, proteins or antibodies of the invention (described above) to detect or treat neuropsychiatric disorders and developmental disorders together with instructions for the use thereof.

The methods and kits of the present invention may be used to detect neuropsychiatric and developmental disorders such as Rett's syndrome and mental retardation. Samples which may be tested include bodily materials such as blood, urine, serum, tears, saliva, feces, tissues, organs, cells and the like. In addition to human samples, samples may be taken from mammals such as non-human primates, etc.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. Therapeutic Applications

As mentioned previously, the nucleic acid molecules of the present invention are deleted or mutated in people with neuropsychiatric disorders and developmental disorders. Accordingly, the present invention provides a method of treating or preventing neuropsychiatric disorders and developmental disorders by administering a nucleic acid sequence containing a sufficient portion of the MECP2E1 splice variant to treat or prevent neuropsychiatric disorders and developmental disorders. The present invention includes a use of a nucleic acid molecule or protein of the invention to treat or detect neuropsychiatric disorders and developmental disorders.

Recombinant molecules comprising a nucleic acid sequence or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

The nucleic acid sequences may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

C. Experimental Models

The present invention also includes methods and experimental models for studying the function of the MECP2 gene and MeCP2E1 protein. Cells, tissues and non-human animals that lack the MECP2E1 splice variant or partially lack in MeCP2E1 expression may be developed using recombinant expression vectors having a specific deletion or mutation in the MECP2E1 gene. A recombinant expression vector may be used to inactivate or alter the MECP2 gene by homologous recombination and thereby create a MECP2E1 deficient cell, tissue or animal. In particular, a targeted mutation could be designed to result in deficient MECP2E1 while MECP2E2 remains unaltered. This can be accomplished by targeting exon 1 of the MECP2 gene.

Null alleles may be generated in cells, such as embryonic stem cells by deletion mutation. A recombinant MECP2 gene may also be engineered to contain an insertion mutation which inactivates MECP2E1. Such a construct may then be introduced into a cell, such as an embryonic stem cell, by a technique such as transfection, electroporation, injection etc. Cells lacking an intact MECP2 gene may then be identified, for example by Southern blotting, Northern Blotting or by assaying for MECP2E1 using the methods described herein. Such cells may then be fused to embryonic stem cells to generate transgenic non-human animals deficient in MECP2E1. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on MECP2E1 expression. The present invention also includes the preparation of tissue specific knock-outs of the MECP2E1 variant.

The following non-limiting examples are illustrative of the present invention:

EXAMPLES

Example 1

Identification of MEC2E1 Splice Variant

Inspection of the 5'UTR revealed that, whereas exon 2 has a number of in-frame stops upstream of the ATG, exon 1 contains an open reading frame across its entire length including an ATG. Submitting a theoretical construct composed of exons 1, 3 and 4 to the ATGpr program (www.hri.co.jp/atgpr/), which predicts the likelihood of an ATG to be an initiation codon based on significance of its surrounding Kozak nucleotide context, returned a reliability score of 97% compared to 64% for MECP2E2. A search in EST databases identified eight examples of our theorized transcript (named MECP2E1) (FIG. 1*b*) (vs. 14 examples of MECP2E2). MECP2E1 would be predicted to encode a new variant, MeCP2E1, with an alternative longer N-terminus determined by exon 1.

Example 2

Expression of MECP2E1

To confirm that MECP2E1 is in fact expressed and not an artifact of cDNA library preparations, cDNA from a variety of tissues was PCR-amplified using a 5'-primer in exon 1 and a 3'-primer in exon 3 (FIG. 1*a*). Two PCR products corresponding to MECP2E2 and MECP2E1 by size and sequence were obtained in all tissues, including fetal and adult brain, and in brain subregions (FIG. 1*c*). Results in mouse were similar (FIG. 1*c*). The expression levels of the two transcripts in adult human brain were quantified. MECP2E1 expression is 10 times higher than MECP2E2 (FIG. 1*d*). The subcellular localization of MeCP2E1 following transfection of 3' myc-tagged MECP2E1 into COS-7 cells was found to be principally in the nucleus (FIG. 1*e*).

MECP2E1 was not detected in previous expression studies. Northern analyses reveal three transcripts, 1.9, 5 and 10.1 kb, with the differences in size due to alternative polyadenylation signal usage (4,6,8) (FIG. 1*a*). MECP2E1 differs from MECP2E2 in lacking the 124-nucleotide exon 2. At the 5 and 10.1 kb positions on the gel, the two transcripts would not be separable. In the 1.9 kb range, published northern blots do show a thick or double band likely corresponding to the two transcripts. Likewise, conventional western blot analysis would not allow resolution of the two MeCP2 isoforms (molecular weight difference <0.9 kD; FIG. 1*f*).

Example 3

Mutations in MECP2E1 in Rett's Syndrome

To determine whether the new coding region is mutated in Rett's syndrome, Exon 1 and flanking sequences were PCR-amplified and sequenced in 19 girls with typical RTT in whom no mutations had been found in the other exons. One patient (V1) was found to carry an 11 bp deletion mutation in exon 1 (FIG. 2). The deletion occurs within the predicted exon 1 open reading frame of MECP2E1 and leads to a frame shift that results in a missense amino acid sequence followed by a premature stop codon after amino acid 36. It does not affect the coding sequence of MECP2E2. This sequence change was not found in 200 control individuals including the patient's parents and brother.

Figure 3:
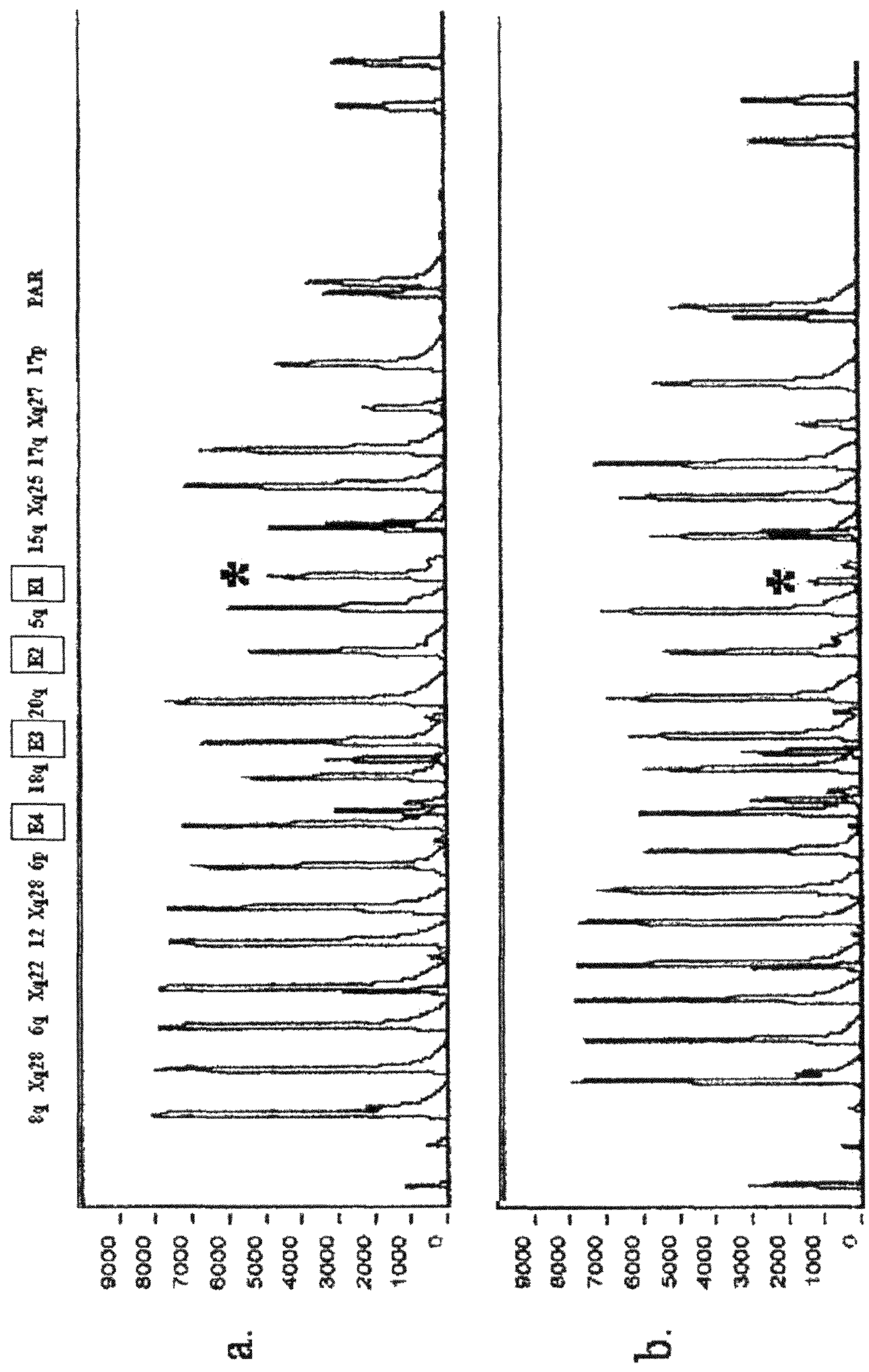
FIG. 3 shows a deletion mutation in patient V2. MECP2 Multiplex ligation-dependent probe amplification (MLPA) peak profiles are shown. Control loci are listed along the top. Boxed regions (E1-E4) indicate MECP2 exons 1-4. a) MLPA profile of normal control. b) MLPA profile of patient V2 shows a hemizygous exon 1 deletion (asterisk). The result was consistently reproducible and sequencing ruled out the possibility of a SNP interfering with the ligation efficiency of the MLPA reaction.

To search, in the remaining patients, for additional exon 1 deletions not detectable by our PCR reaction, multiplex ligation-dependent probe amplification (MLPA) (5) was performed in all four exons and detected a hemizygous deletion of exon 1 in one patient (Patient V2; FIG. 3). Finally, an additional patient with an MLPA-detected deletion restricted to exon 1 was recently documented in abstract form, though the effect on MECP2E1 was not realized (S. Boulanger et al. *Am J Hum Genet.* 73, 572 (2003)).

In contrast, no mutation specific to the MeCP2E2-defining exon 2 has been found to date despite several hundred patients analyzed for mutations in this exon (31 publications; most reviewed in ref 3). These studies did not include exon 1 as it was considered non-coding.

Exon 1 deletions result in absent or truncated MeCP2E1 proteins. However, they also result in shortening of MECP2E2's 5'UTR and may possibly affect its expression. This possibility was tested in patient V1 by RT-PCR on whole blood. No diminution of MECP2E2 expression was present (FIG. 2*c*). In conclusion, mutation data indicate that inactivation of MeCP2E1 is sufficient in RTT, but the same cannot be said, to date, of MeCP2E2.

Materials and Methods

PCR, manual sequencing, cloning, rtPCR, gel blotting. PCR amplification was performed using $[NH_4]_2SO_4$-containing PCR buffer (MBI Fermentas) with 1M betaine, 200 μM dNTPs including 50% deaza dGTP, with a 95° C. denaturing step for 3 minutes, followed by cycling at 95° C. for 30 secs, 55° C. for 30 secs, 72° C. for 45 secs for 30 cycles, followed by a 7 minute soak step at 72° C. Manual sequencing was performed, following extraction from a 1% agarose gel, using the Thermosequenase™ kit (USB/Amersham) and run on a 6% denaturing polyacrylamide gel for 3 hours. PCR products were cloned using the pDRIVE vector (Qiagen PCR cloning kit). Whole blood RNA was extracted using the PAXgene Blood RNA Kit (Qiagen). Reverse transcription was performed with random hexamers and a standard Superscript III protocol (Invitrogen). Human brain subregion cDNA was obtained from OriGene. The polyacrylamide gel in (FIG. 2*c*) was blotted onto Hybond N+ (Amersham) and hybridized with primer HF labeled at the 3' end with $[\alpha^{32}P]$-dCTP using deoxynucleotidyl transferase (MBI Fermentas).

Figure 4:
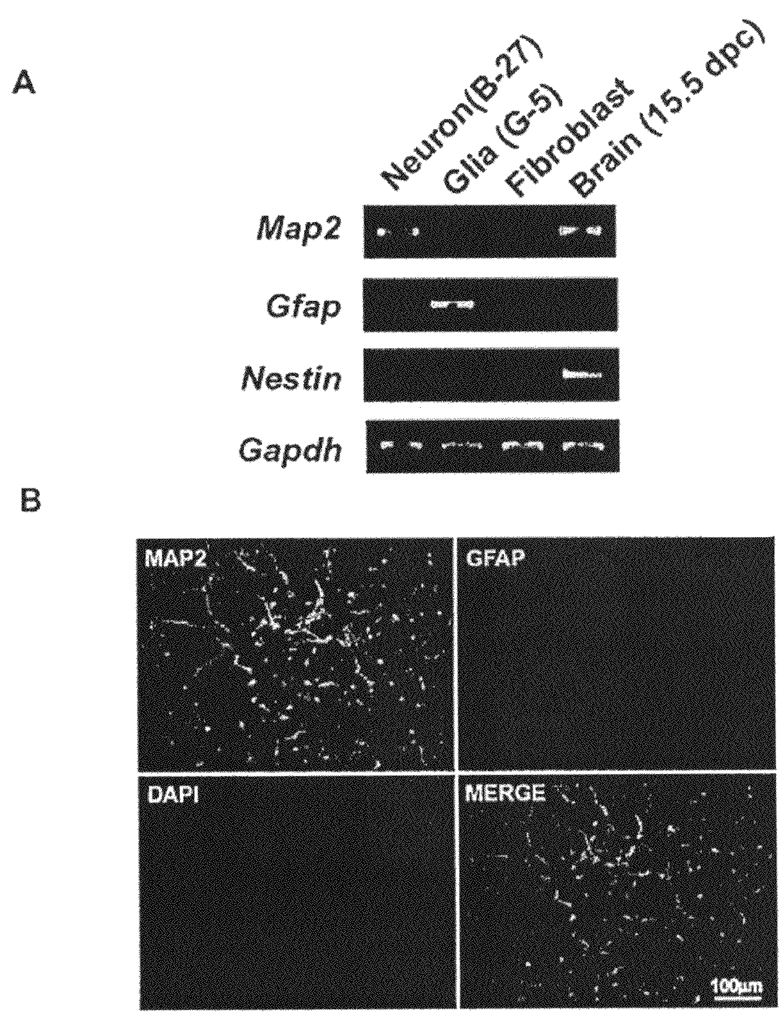
FIG. 4 shows the characterization of the primary brain cell cultures by rtPCRR (A) and IF (B). (A) Map2, Gfap and Nestin expressions indicate that the cultures in B-27 medium were composed primarily of neurons and those in G-5 medium were glial cells. Fibroblasts from the same embryos were also cultured and used as negative controls. Whole brain tissue (15.5 dpc) was used as a positive control for Map2 and Nestin. (B) Double staining for neurons was performed with mouse anti-MAP2 and rabbit anti-GFAP antibodies. They were also counterstained with DAPI (blue). Most of the cells are neurons, which stained positively for MAP2 (green), and an insignificant percentage of contamination with glial cells stained positively for GFAP (red) was detected.

Preparation of neuronal and glial cultures. Cerebral cortices were prepared from 15.5 days postcoitum (15.5 dpc) embryos of CD-1 mice. The procedure of Yamasaki et al. (Yamasaki et al. Hum Mol Genet. 12: 837-847, 2003) was used. Briefly, fetal cerebral cortices without meninges were dissociated by mechanical trituration and digested with 0.25% trypsin with EDTA. After adding fetal bovine serum (FBS; GIBCO BRL), filtered cells were collected by centrifugation. The cell pellet was resuspended in Neurobasal (GIBCO BRL) medium supplemented with B-27 (GIBCO BRL) for growth of neurons or with G-5 (GIBCO BRL) for growth of glial cells. Cells were plated on polyethyleneimine-coated plastic dishes at a density of $2\times10^6$ cells/ml. Cultures of neurons and glial cells were maintained in 5% $CO_2$ at 37° C. for 6 days and 12 days, respectively. Isolated brain cells were characterized by RT-PCR and immunofluorescence (IF) using the markers MAP2 (microtubule-associated protein 2) for neurons, GFAP (glial fibrillary acidic protein) for glial cells and NESTIN for progenitor cells. For IF, the following specific antibodies were used: mouse monoclonal anti-MAP2 (CHEMICON), and rabbit polyclonal anti-GFAP (DAKO). The primers used for rtPCR were same as Yamasaki et al. To obtain a semi-quantitative PCR, optimal cDNA concentration and number of cycles were determined according to Gapdh amplification as an internal control. FIG. 4 shows the characterization of the primary brain cell cultures by rtPCR (A) and IF (B).

Quantitative rtPCR. To determine the quantity of the MECP2 transcripts in different tissues, we developed transcript-specific real-time quantitative PCR assays using SYBR Green detection method (PE Applied Biosystems, ABI PRISM 7900 Sequence Detection System). The following MECP2E2-specific forward primer (25 nM) (in exon 2) was designed: 5'-ctcaccagttcctgctttgatgt-3' (SEQ ID No. 12). The MECP2E1-specific primer (25 nM) was placed at the junction of exons 1 and 3: 5'-aggagagactggaagaaaagtc-3' (SEQ ID No. 10). Both assays used the same reverse primer (25 nM) in exon 3: 5'-cttgaggggtttgtccttga-3' (SEQ ID No. 11), producing fragments of 161-(MECP2E2) and 65-bp (MECP2E1). The corresponding transcript-specific primers (25 nM) for the mouse mecp2 transcripts (mecp2e2 167 bp and mecp2e 1 71 bp) were 5'-ctcaccagttcctgctttgatgt-3' (SEQ ID No. 12) (MECP2E2); 5'-aggagagactggaggaaaagtc-3' (SEQ ID No. 13) (MECP2E1) and the common reverse primer 5'-cttaaacttcagtggcttgtctctg-3' (SEQ ID No. 14). PCR conditions were: 2 min 50 C, 10 min 95 C and 40 cycles of 15 sec 95 C, 85 s 60 C. The PCR reactions were performed in separate tubes; and absolute quantitation of the MECP2E2 and E1 transcripts was performed from cDNA from human adult brain, cerebellum, fibroblast and lymphoblast (Clontech, Palo Alto, USA), as well as from murine neuronal and glial cell cultures (see above). Results were analyzed using the standard curve method according to the manufacturer's instructions (PE Applied Biosystems, ABI PRISM 7900 Sequence Detection System). The standard curve was developed using dilutions of the transcript-specific purified PCR products.

Immunofluorescence light microscopy. 3'-myc-tagged MECP2E2 and MECP2E1 constructs (pcDNA3.1A-MECP2E2-myc and pcDNA3.1A-MECP2E1-myc) were generated by PCR amplification of full-length cDNA of each transcript with BamHI (5') and XbaI (3') restriction sites attached and subsequent cloning in-frame with myc into pcDNA3.1 version A (Invitrogen). The forward primer for MECP2E2 contained the start codon in exon 2 (5'-tatggatccATGgtagctgggat-3') (SEQ ID No. 15), while the forward primer for MECP2E1 included the start codon in exon1 (5'-tatggatccggaaaATGgccg-3') (SEQ ID No. 16) (BamHI restriction site underlined, start codon uppercase). The reverse primer was the same for both amplifications (5'-gcgtctagagctaactctct-3') (SEQ ID No. 17) (XbaI restriction site underlined). The template used for PCR was small intestine cDNA for MECP2E2 and skeletal muscle cDNA for MECP2E1. pcDNA3.1A-MECP2E2-myc and pcDNA3.1A-MECP2E1-myc (tug) were transfected into COS-7 cells using lipofectamine (Invitrogen) and the lipid-DNA complex was exposed in DMEM (GIBCO) for 5 hours. Forty-eight hours post-transfection the cultures were rinsed in PBS and fixed for 15 min at −20° C. in an acetone:methanol (1:1) mix, blocked for 1 hour (10% BSA in PBS) and incubated with anti-myc (Santa Cruz Biotechnology, 1:50 in blocking buffer) for 45 min at room temperature. After washing with PBS, slides were incubated with secondary antibody (FITC-labeled goat anti-mouse (Jackson Immunoresearch labs), 1:400, detectable through the green filter) in blocking solution, mounted with Dako Anti-Fade and analyzed by immunofluorescence light microscopy.

MLPA analysis. MLPA was performed as described by Schouten et al., supra and as described by Schouten, supra. MECP2 test kits from MRC-Holland, Amsterdam, Netherlands (www.mrc-holland.com) were utilized and consisted of 20 probe pairs that target the four MECP2 exons, six X-linked control regions and ten autosomal control regions. Briefly, 100-200 ng of genomic DNA was denatured and hybridized with the probe mix overnight at 60° C. The following morning the paired probes were ligated using heat stable Ligase-65 at 54° C. for 15 minutes. The ligation was followed with PCR with a common primer pair that hybridizes to the terminal end of each ligation product. One PCR primer was FAM-labeled and conditions for the PCR were as follows: 95° C. 30 s, 60° C. 30 s and 72° C. 1 min. The resulting amplicons were analyzed on an ABI 3100 capillary electrophoresis instrument and ABI Genescan software. All data management and comparisons to normal controls were done with Excel software.

Discussion

Recently, studies in frog (*Xenopus laevis*) afforded important insight into the role of MeCP2 in neurodevelopmental transcription regulation. MeCP2 was shown to be a component of the SMRT complex involved in the regulation of genes involved in neuronal differentiation following developmental stage-specific mediation by Notch-Delta. The frog Mecp2 transcript targeted for silencing in these experiments is an orthologue of MECP2E1 (FIG. 10. In fact, MeCP2E1 appears to be the only form of MeCP2 in non-mammalian vertebrates (FIG. 10.

The new MeCP2 N-terminus is a distinctive 21 amino acid peptide including polyalanine and polyglycine tracts (MAAAAAAAPSGGGGGGEEERL) (SEQ ID No. 18) (FIG. **1*f*). A similar N-terminus occurs in the ERK1 (MAPK3) extracellular signal-regulated kinase (FIG. 10**, a key common component of multiple signal transduction pathways. Intriguingly, in neurons, both ERK1 and MeCP2 have been shown to be present in the post-synaptic compartment, in addition to the nucleus, and the former shown to translocate between the two compartments to link synaptic activity to transcriptional regulation. It is possible that MeCP2E1 similarly links synaptic function, in this case neurodevelopmental synaptic contact guidance, with transcriptional regulation. The only other proteins in which consecutive polyalanine and polyglycine tracts are found are in some members of the homeobox (HOX) family. These, like MeCP2, are developmental transcription regulators.

Finally, non-inactivating MECP2 mutations have been associated with phenotypes that overlap RTT such as mental retardation and autism. The MeCP2 variant discovered in this study is a candidate for involvement in these disorders.

Example 4

Mutations in MECP2E1 in Mental Retardation

Figure 5:
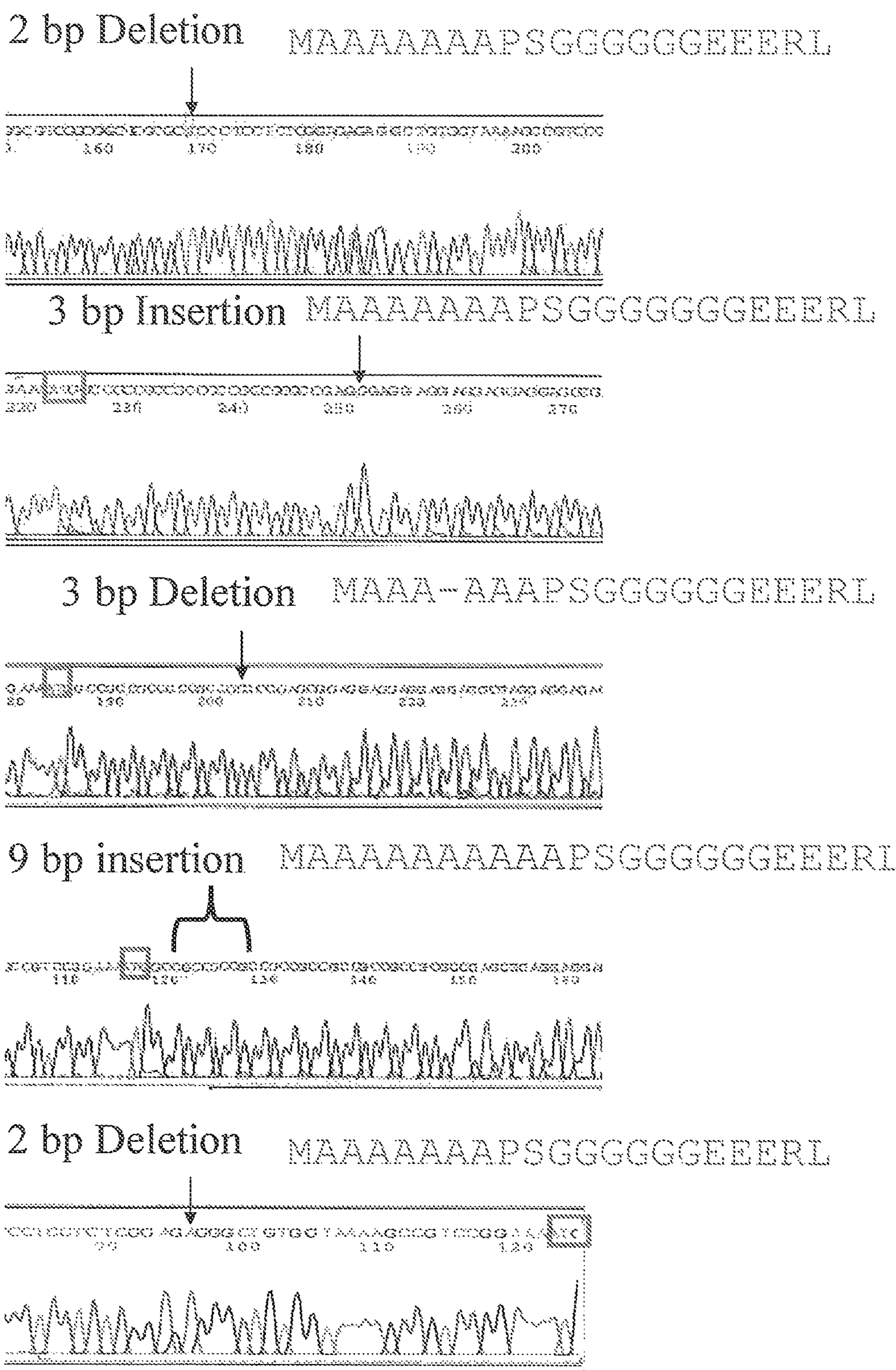
FIG. 5 shows the nucleotide sequence of the five MECP2 exon 1 variants identified in female MR patients. All sequences were obtained from single colonies, after cloning the heterozygious PCR product into the pDRIVE vector (Qiagen). The ATG start codon is indicated by a red box, where possible. The resulting amino acid sequence is also indicated, with wild type sequence shown in red, and changes indicated in green type.

The inventors screened the MECP2E1 gene in N=401 autism probands, and in N=493 patients with non-specific mental retardation. Autism probands recruited through the Hospital for Sick Children in Toronto (N=146; 114 male, 32 female) and from London, UK (N=13; 10 male, 3 female) were also screened, as well as probands from multiplex families from the Autism Genetic Resource Exchange (AGRE; N=242; 100 female, 142 male). Local institutional ethics board approval was obtained, and written consent given by participants. Anonymized DNA samples were also obtained for 293 female and 200 male patients with non-specific developmental delay/mental retardation who had been referred for fragile-X testing (but tested negative) to the Department of Pediatric Laboratory Medicine at the Hospital for Sick Children. Polymerase chain reaction followed by denaturing high performance liquid chromatography (DHPLC) was used for mutation detection, with PCR primers and conditions as described previously in Example 3. PCR product from female individuals suspected of carrying a sequence variant was cloned into the pDRIVE vector (Qiagen), and at least four clones sequenced using automated BigDye™ Sequencing (ABI 3100) in forward and reverse directions. PCR products from males were excised from agarose gel, column purified, then sequenced, also using automated BigDye™ Sequencing (ABI 3100) in both forward and reverse directions. No mutations were identified among the autism screening set, however sequence variants were identified among eight of the female MR cases (see FIG. 5), three of which result in insertion or deletion of amino acids within the polyalanine repeat stretch, and two of which result in insertion of a glycine residue within the polyglycine repeat at the N-terminal portion of MECP2E1. The first individual identified was heterozygous for a deletion of a GpC dinucleotide positioned 45-46 bp upstream of the putative MECP2E1 start codon. This deletion could disrupt a potential SP1 transcription factor binding site (as predicted using AliBaba2.1 at http://www.gene-regulation.com/pub/programs/alibaba2/index.html), and may also eliminate potentially methylatable cytosine residues. Another individual is heterozygous for an ApG dinucleotide deletion 26 bp upstream of the MECP2E1 start codon. Two individuals are heterozygous for a GGA trinucleotide insertion within a poly[GGA] stretch, which would result in an additional glycine residue within the predicted polyglycine stretch. A fifth individual is heterozygous for a GCC trinucleotide deletion within a triplet repeat stretch encoding polyalanine. Two individuals are heterozygous for a 9 bp insertion, also within the GCC trinucleotide repeat/polyalanine region, and would result in the polyalanine stretch being extended from seven to ten residues.

The amino acid sequence variation in ±2% of female non-specific MR cases in a new isoform of a protein that has previously been associated with a mental retardation syndrome, is extremely intriguing. Moreover, the fact that the variation occurs within a part of the protein that is conserved across many vertebrate species also adds to the interest (100% identity to chimpanzee, orang-utan, macaque, cat and dog MeCP2E1 amino acid sequence). It would be particularly useful to know whether there are any specific phenotypic features among the individuals with the variants, how severe the symptoms are an whether there are overlaps with or distinctions from the Rett syndrome phenotypes. However, since the DNAs were anonymized, it is not possible, in this instance, to correlate the mutations discovered with phenotypic features or severity. In an attempt to address this issue, a second sample set of MR cases (188 female and 96 male) from the Greenwood Genetic Center, S.C., were screened, followed by sequencing. No variants were found in the males, and two of the females carried the GGA insertion encoding an extra glycine residue.

In the present study, three female MR patients were identified with a 3 bp insertion leading to an extra glycine residue within the polyglycine stretch at the N-terminal end of MeCP2E1. No disease association has previously been reported with expansion within a glycine repeat. The function of polyglycine stretches, either within the context of the MeCP2E1 protein or more generally, is not known, although a study of the Toc75 protein in plants suggests that a polyglycine stretch in the protein is essential for correct targeting of the protein to the chloroplast outer envelope. A similar function of protein trafficking may also be the case for mammalian proteins with polyglycine stretches, and for MeCP2E1.

The variants within the polyalanine tracts are of particular interest, as they are rarely polymorphic, and because a number of small expansions (or duplications) within such tracts have been reported to cause diseases, ranging from cleidocranial dysplasia (RUNX2), oculopharyngeal muscular dystrophy (PABPN1) and mental retardation (ARX; this gene is also X-chromosomal and has a very broad array of phenotypes-see above). The majority of polyalanine disease genes encode transcription factors, although PABPN1 gene encodes a polyadenylate binding protein. On the one hand, amongst these diseases, the smallest pathogenic repeats within the transcription factor genes are generally greater than 20 alanines in length, thus it could be considered improbable that a stretch of alanines as short as that encoded by MECP2E1 could be pathogenic, and a change of 1 or 3 alanine residues could be considered likely to be rare polymorphisms. There is currently some uncertainty as to whether small expansion of 1 or 3 alanine residues within the ARX gene may be pathogenic or innocent variants. On the other hand, oculopharyngeal muscular dystrophy is caused by mutations within a GCG tract in the PABPN1 gene, that expand a polyalanine tract from just 10 alanine residues to between 12 and 17 alanine residues. Moreover, as with the polyalanine tract in MeCP2E1, the polyalanine tract in PABPN1 is right at the N-terminal end of the gene, and thus it is possible that smaller mutations within repeat stretches within the N-terminal portion of a protein may be more detrimental than larger mutations located in the central portions of proteins.

A recently published study screened for mutations in MECP2 exon 1 among 97 Rett patients with no mutation in exons 2, 3 or 4, and among 146 controls. One of the Rett patients was found to have a 6 bp insertion within the polyalanine-encoding [GCC] stretch, but no such variations were observed among the controls. The variant was inherited from an unaffected mother, and it was concluded that the variant is thus unlikely to be etiologically relevant. However, it has also been demonstrated recently that even subtle changes in expression of MECP2 in mice can have profound neurological and behavioural consequences. It is apparent that patients with the same MECP2 mutation may have very different phenotypic features and severity, and it is likely that variation in X-inactivation pattern plays a role in this discordancy. Thus it is quite feasible that variation in exon 1, either within the repeat stretches resulting in change in length of polyalanine or polyglycine stretch, or in the region just upstream of the start codon, may affect function or expression levels resulting in a neuropathological phenotype.

Example 5

Additional Mutations in MECP2E1 in Rett's Syndrome

The entire coding regions of exons 1, 2, 3 and 4 and their intronic flanking sequences were analyzed. Exons 2 to 4 were amplified by PCR with primer pairs designed with the use of genomic sequence information from the Human Genome Project working draft site (UCSC, www.genome.ucsc.edu) and the Lasergene Primer select program. The PCR products were loaded on 2% agarose gel to confirm amplification before analysis for base changes by dHPLC (WAVE Nucleic Acid Fragment Analysis System from Transgenomic, San Jose, Calif.). Solvent A consisted of 0.1 mol/L triethylammonim acetate (TEAA) and 25% acetonitrile and solvent B contained 1M TEAA, 25% acenonitril. PCR products showing a chromatographic variation on dHPLC were sequenced directly on an automatic sequencer (Gene Reader 4200). The sequencing data was analyzed using DNA Star software SeqMan (Lasergene). Exon 1 was PCR amplified and sequenced in all patients as recently described.

The first exon 1 mutation consists of two missing base pairs at the exon 1 intron 1 boundary. Because of the nature of the sequence in this region, we cannot resolve whether the missing two nucleotides are the first two base pairs of intron 1 (GT) or the last nucleotide of exon 1 (T) and the first nucleotide of intron 1 (G). In either case, the missing pair of nucleotides destroys the predicted consensus splice site and results in readthrough of intron 1 (data not shown). In the second patient with an exon 1 mutation a 1A→T substitution (ATG->TTG) changes the first Methionine codon into a Leucine. The prediction is that MECP2E1 translation would be greatly or totally hindered due to absence of a start codon. MECP2E2 would be normally made (and appears unable to rescue the disease phenotype).

Example 6

Additional Mutations in MECP2E1 in Rett's Syndrome

Patients

Thirty-five samples from females were referred to Children's Mercy Hospital for RTT testing in a two year period spanning September of 2004 through September of 2006 (See, for example, Saunders, C. J., et al., "Novel Exon 1 Mutations in MECP2 Implicate Isoform MeCP2_e1 in Classical Rett Syndrome," *American Journal of Medical Genetics,* 149A: 1019-1023 (2009)). These patients had various clinical presentations, including autism, mental retardation, developmental delay, and "Angelman-like", and only 9 patients fit the criteria for classical (N=7) or variant (N=2) RTT. Permission to review patient charts was obtained through the Children's Mercy Hospitals and Clinics' Institutional Review Board. In addition, 16 female patients were ascertained through either the Hospital for Sick Children or Centre for Addiction and Mental Health in Toronto, either with autism and developmental delay (N=14) or Rett syndrome (N=2). This ascertainment was subsequent to the study reported by Mnatzakanian, G. et al., "A previously unidentified MECP2 open reading frame defines a new protein isoform relevant to Rett syndrome," *Nat. Genet.,* 36: 339-341 (2004) and there is no overlap of subjects between that and the current study. Screening for mutations in MECP2 identified four patients with mutations involving exon 1.

Patient 1 was a 20-year-old at the time of testing who had a long standing clinical diagnosis of RTT but had never undergone confirmatory DNA testing. She met the criteria for classical RTT, with the exception of acquired microcephaly (head circumference is at 15%). Following normal perinatal development, she sat at 6 months, walked at 14 months, used simple words at 18 months, around which time she began to regress. She lost all speech in addition to purposeful hand movements, which were replaced by a sifting activity. She now walks with a shuffling gait, exhibits some aggressive behavior, is nonverbal, and has medically intractable epilepsy.

Patient 2 was 7 years old at the time of testing. She met the criteria for classical RTT, with the exception of acquired microcephaly (head circumference 50%). She had a period of normal development, such as smiling, rolling over, and sitting at appropriate times, but around 10 months she exhibited global developmental delay. There was no clear regression in her skills at that point. Around the age of 2, she developed a stereotypic midline hand movement involving her left hand in her mouth and her right hand twirling her hair or rubbing her hair between her fingers. She commando crawls for mobility and will take steps with assistance. She is very hirsute and has precocious puberty with pubic hair development beginning at age 5. She has episodic seizures that do not require daily medication. She had previously tested negative for MECP2 mutations in exons 2-4, MECP2 duplications and deletions, and research testing involving sequencing of the MECP2 promoter region. The family came to the clinic in pursuit of mutation screening for the cyclin-dependent kinase-like 5 (CDKL5) gene, but upon closer examination of the patient's medical record, it was discovered that exon 1 of MECP2 had not been sequenced.

Patient 3 was a 16-year-old female with a clinical diagnosis of Rett syndrome since 20 months of age. She had microcephaly, developmental regression, severe cognitive insufficiency, midline hand movements, general tonic-clonic seizure disorder, loss of gait, diffuse hypertonicity, scoliosis treated with surgery, GE reflux requiring gastrostomy tube, and multiple hospitalizations for bacterial pneumonia. On her last admission for pneumonia, she succumbed to respiratory insufficiency and was not resuscitated. Brain autopsy showed microencephaly, subpial gliosis, minimal loss of Purkinje cells with gliosis, and isolated eosinophilic neurons in the dentate nucleus and brain stem. Previous testing for MECP2 exons 2-4 was negative.

Patient 4 had a clinical diagnosis of Rett syndrome since age 10. At birth, she had a normal head circumference but poor muscle tone. Global developmental delays, intense eye contact and screaming spells were noted in infancy. Teeth grinding, hand flapping, and deterioration in fine motor skills began from age 3 to 4. Speech development was slow but she acquired a vocabulary of about 25 words before the onset of loss of speech at age 6 and she became non-verbal by age 10. She first walked at age 14 months following intensive physiotherapy, and still walks unassisted despite occasional loss of balance due to mild gait dyspraxia. Other significant medical history included scoliosis (treated with surgery) and chronic constipation. There is no history of seizures or acquired microcephaly. When the patient was 28 years old, the family sought molecular genetic testing to confirm the clinical diagnosis of Rett syndrome.

Research ethics board approval was obtained for the study, and written consent obtained for the four patients described here.

Sequence Analysis

DNA from blood, or in the case of patient 3, cultured fibroblast cells, was extracted by a manual salting out procedure (Lahiri, D. K. and Numberger, J. I., "A rapid non-enzymatic method for the preparation of HMW DNA from blood for RFLP studies," *Nucleic Acids Res.,* 19: 5444 (1991)). For most of the 35 subjects the entire MECP2 coding region (exons 1-4) was analyzed (primers and PCR conditions available upon request); for Patients 2 and 3, only exon 1 was analyzed since the remaining coding region had been previously tested by an outside laboratory. Exon 1 of the MECP2 gene was PCR-amplified as described previously (Mnatzakanian, G. et al., "A previously unidentified MECP2 open reading frame defines a new protein isoform relevant to Rett syndrome," *Nat. Genet.,* 36: 339-341 (2004)) and verified on a 2% agarose gel. Fragments were purified using ExoSAPit (USB Corp., Cleveland Ohio). Purified products were sequenced in both forward and reverse directions by automated fluorescent dye-terminator sequencing using Big Dye v3.0 (Applied Biosystems, Foster City, Calif.) and run on an ABI310 (Applied Biosystems). For Patient 2, allele-specific sequence was obtained after cloning the heterozygous PCR product into a TA cloning vector (Invitrogen, Carlsbad, Calif.). The sequence data was compared to the MECP2 reference sequence AF030876 using Sequencher software (Gene Codes, Ann Arbor, Mich.).

In silico analysis of efficiency of translation start sites affected by exon 1 mutations was performed on MEPC2 mRNA sequences using NetStart (www.cbs.dtu.dk/services/NetStart).

X-Chromosome Inactivation

X-chromosome inactivation was assessed on genomic DNA from peripheral blood leukocytes by methylation-sensitive restriction digestion followed by PCR amplification across the androgen receptor [CAG] repeat region, according to the method described by Plenge, R. M. et al., "Skewed X-chromosome inactivation is a common feature of X-linked mental retardation disorders," *Am J Hum Genet.,* 71: 168-173 (2002).

Results

In 51 samples tested for RTT, four unrelated patients with exon 1 mutations were identified.

In Patient 1, a mutation was detected, c.1A>T in SEQ ID No. 1 that disrupts the initiation codon, changing it to a leucine. SEQ ID No. 1 contains non-coding exon sequence upstream of the start codon, so the mutation is located at position 8 in SEQ ID No. 1 which corresponds to the first position in the coding exon of SEQ ID No. 1. In silico analysis of translation initiation using NetStart predicts that translation of MeCP2_e1 would be ablated, but without any negative affect on translation of MeCP2_e2. The patient's mother tested negative for this mutation, however the father's DNA was not available for testing. X-chromosome inactivation in peripheral blood leukocytes appeared to be random.

Patient 2 has a mutation, c.62+1delTG in SEQ ID No. 1, affecting the splice donor (Amir, R. E. et al., "Mutations in exon 1 of MECP2 are a rare cause of Rett syndrome," *J Med. Genet.,* 42: e15 (2005)). SEQ ID No. 1 contains non-coding exon sequence upstream of the start codon, so the mutation is located at positions 69 and 70 in SEQ ID No. 1 which corresponds to positions 62 and 63 in the coding exon of SEQ ID No. 1. Analysis of parental DNA revealed that it arose as a de novo mutation, not present in either parent. This mutation is predicted to disrupt splicing of the MECP2E1 mRNA, and may also affect the translation of the MeCP2_e2 isoform from the exon 2-containing mRNA, MECP2E2 (Amir, R. E. et al., "Mutations in exon 1 of MECP2 are a rare cause of Rett syndrome," *J Med. Genet.,* 42: e15 (2005) and Saxena, A. et al., "Lost in translation: translational interference from a recurrent mutation in exon 1 of MECP2," *J Med. Genet.,* 43: 470-477 (2006)). This patient had a random pattern of X-chromosome inactivation in peripheral blood leukocytes.

Patient 3 had a C>T transition (c.5C>T) in SEQ ID No. 1 resulting in a missense mutation, A2V. SEQ ID No. 1 contains non-coding exon sequence upstream of the start codon, so the mutation is located at position 12 in SEQ ID No. 1 which corresponds to the fifth position in the coding exon of SEQ ID No. 1. Though an alanine to valine substitution is conservative in retaining a nonpolar side chain, this is a residue that is perfectly conserved throughout evolution and marks the beginning of a polyalanine stretch which is present in all vertebrate species (Harvey, C. G. et al., "Sequence Variants Within Exon 1 of MECP2 Occur in Females With Mental Retardation," *Am J Med Genet* (*Neuropsychiatr Genet*), 144: 355-360 (2007)). Though the role of this repeat is unknown, it contains multiple binding sites for the SP 1 transcription factor, the alterations of which would affect the rate of gene transcription. This patient's parents both tested negative for this mutation, indicating this is a de novo mutation.

Patient 4 had a A>G transition (c.1 A>G) in SEQ ID No. 1 resulting in the start methionine codon being substituted by a valine codon. SEQ ID No. 1 contains non-coding exon sequence upstream of the start codon, so the mutation is located at position 8 in SEQ ID No. 1 which corresponds to the first position in the coding exon of SEQ ID No. 1. Both parents were negative for this mutation. As with Patient 1, this mutation is predicted to ablate translation of MeCP2_e1, but without any negative affect on translation of MeCP2_e2. X-chromosome inactivation in peripheral blood leukocytes showed skewing, 90:10.

The presence of these missense/start codon mutations in classic Rett patients, uniquely affecting the MeCP2_e1 isoform, clearly indicates the importance of this isoform in the etiology of Rett syndrome. None of these sequence changes were identified in a previous study that screened MECP2 exon 1 in 1,811 subjects with developmental delay or autism, and 498 healthy adult control individuals (Harvey, C. G. et al., "Sequence Variants Within Exon 1 of MECP2 Occur in Females With Mental Retardation," *Am J Med Genet* (*Neuropsychiatr Genet*), 144: 355-360 (2007)).

Discussion

MECP2 was sequenced in 51 females with various clinical presentations, including developmental delay, autism, atypical and classical RTT, referred to the laboratory for testing. In patients with identified mutations, X-chromosome inactivation was analyzed. Four, patients were identified with exon 1 mutations (c.1A>T; c.1A>G; c.5C>T), two of which affected the start codon, one a missense change, and one patient had a previously reported splice site mutation, c.62+1delGT. The 4 patients fit criteria for classical RTT, and thus these findings add support to previous reports that exon 1 mutations may be associated with a severe phenotype. Also, these findings add significant weight to the mounting evidence suggesting that the MeCP2_e 1 isoform is the etiologically relevant form of the protein.

As discussed above, three mutations were detected within exon 1 of the MECP2 gene in 35 clinical samples referred to CMH for MECP2 sequencing, and in one out of 16 samples from the Toronto patient set. All four were associated with classical RTT. Two of these patients had previously tested negative by molecular testing, which at the time included sequencing of exons 2-4 of the MECP2 gene. Following the reports of the second MeCP2 isoform (MeCP2_e1) and the clinical utility of sequencing exon 1, these patients were tested for exon 1 mutations. The total number of distinct exon 1 mutations detected by sequencing is now 10. Two of these mutations, c.47_57del11nt and c.62+1delGT, have been found in more than one patient (see Table 2). This brings the number of Rett patients known to have a mutation within exon 1 of MECP2 to 14.

All mutations localized to exon 1 reported until recently have been either small insertions or deletions or large deletions removing the entire exon. The c.1A>T and c.1A>G mutations, which are single base pair changes, are the first point mutations to be reported in exon 1 of the MECP2 gene (also see Gauthier, J. et al., "Clinical stringency greatly improves mutation detection in Rett syndrome," Can *J Neurol Sci,* 32: 321-6 (2005)). The c.1A>T and c.1A>G mutations alter the initiation codon, which would mostly likely result in absent translation of MeCP2_e1 MeCP2_e2 would be presumably unaffected but is clearly unable to compensate, as evidenced by the patients' classic RTT symptoms. Patient 3 had a C>T transition (c.5C>T) resulting in a missense mutation, A2V. This alanine is a perfectly conserved residue that marks beginning of a polyalanine stretch that is present in all vertebrate species (Harvey, C. G. et al., "Sequence Variants Within Exon 1 of MECP2 Occur in Females With Mental Retardation," *Am J Med Genet* (*Neuropsychiatr Genet*), 144: 355-360 (2007)). The role of this repeat is unknown, but it could play a role in the regulation of gene transcription, given the multiple binding sites for the SP1 transcription factor. This patient's parents both tested negative for this mutation, indicating this is a de novo, most likely pathogenic mutation. This also emphasizes the functional importance of the N-terminal portion of MeCP2_e1. There are a number of lines of evidence pointing to the likelihood that the MeCP2_e1 isoform is more relevant to RTT etiology than MeCP2_e2: a) no exon 2 missense mutations (which should only affect MeCP2_e2) have been identified to date; b) MeCP2_e1 is the predominant isoform expressed in neuronal tissues Kriaucionis, S, and Bird, A., "The major form of MECP2 has a novel N-terminus generated by alternative splicing," *Nucleic Acids Res,* 32: 1818-1823 (2004); Mnatzakanian, G. et al., "A previously unidentified MECP2 open reading frame defines a new protein isoform relevant to Rett syndrome," *Nat. Genet.,* 36: 339-341 (2004)); c) MeCP2_e1 appears to be the ancestral form of the gene-MeCP2_e2 is only found among the higher vertebrates (Mnatzakanian, G. et al., "A previously unidentified MECP2 open reading frame defines a new protein isoform relevant to Rett syndrome," *Nat. Genet.,* 36: 339-341 (2004) and Harvey, C. G. et al., "Sequence Variants Within Exon 1 of MECP2 Occur in Females With Mental Retardation," *Am J Med Genet* (*Neuropsychiatr Genet*), 144: 355-360 (2007). On the other hand, analysis of the MECP2 exon 1 11 bp deletion (c.47_57del11nt (p.Gly16Glufs)) identified in a number of studies (Mnatzakanian, G. et al., "A previously unidentified MECP2 open reading frame defines a new protein isoform relevant to Rett syndrome," *Nat. Genet.,* 36: 339-341 (2004); Amir, R. E. et al., "Mutations in exon 1 of MECP2 are a rare cause of Rett syndrome," *J Med. Genet.,* 42: e15 (2005); Saxena, A. et al., "Lost in translation: translational interference from a recurrent mutation in exon 1 of MECP2," *J Med Genet.,* 43: 470-477 (2006); and Ravn, K. et al., "Mutations found within exon 1 of MECP2 in Danish patients with Rett syndrome," *Clin Genet.,* 67: 532-533 (2005)) has suggested that both isoforms of MeCP2 are disrupted in these patients, and thus could not exclude a role for MeCP2 e2 in RTT etiology (Saxena, A. et al., "Lost in translation: translational interference from a recurrent mutation in exon 1 of MECP2," *J Med. Genet.,* 43: 470-477 (2006)). However, the missense and start codon mutations, where only MeCP2_e1 is likely disrupted, cast further doubt on a role for MeCP2_e2 in the disorder.

Previous studies have concluded that sequencing exon 1 contributes little to the mutation detection rate in RTT, even in pre-selected populations such as classical RTT patients who had already tested negative for mutations in exons 2-4 of the gene (Amir, R. E. et al., "Mutations in exon 1 of MECP2 are a rare cause of Rett syndrome," *J Med Genet.,* 42: e15 (2005); Evans, J. C. et al., "Variation in exon 1 coding region and promoter of MECP2 in Rett syndrome and controls," *Eur J Hum Genet.,* 13: 124-126 (2005); and Quenard, A. et al., "Deleterious mutation in exon 1 of MECP2 in Rett syndrome," *Eur J Med. Genet.,* 49: 313-322 (2006)). However, the results of the study described herein, which spanned two years with a total of 51 female patients tested, a minority of whom met the clinical criteria for classical RTT (9) or variant RTT (2), were quite different. Other clinical presentations such as autism or developmental delay were much more frequent in this testing population, which would be less likely to be associated with a MECP2 mutation. Seven other studies examining the exon 1 mutation frequency in Rett females have been published to date (see Table 3). All of these studies were restricted to patients meeting criteria for classic or variant RTT and except for one study (Quenard, A. et al., "Deleterious mutation in exon 1 of MECP2 in Rett syndrome," *Eur J Med. Genet.,* 49: 313-322 (2006)), all were looking at patients who had previously tested negative for mutations in exons 2-4. The detection rates for mutations within exon 1 range from 0% to 25% (See Table 3) in these studies, with several groups concluding that exon 1 mutations are a rare cause of RTT (Amir, R. E. et al., "Mutations in exon 1 of MECP2 are a rare cause of Rett syndrome," *J Med. Genet.,* 42: e15 (2005); Evans, J. C. et al., "Variation in exon 1 coding region and promoter of MECP2 in Rett syndrome and controls," *Eur J Hum Genet.,* 13: 124-126 (2005); and Quenard, A. et al., "Deleterious mutation in exon 1 of MECP2 in Rett syndrome," *Eur J Med. Genet.,* 49: 313-322 (2006)). In this study of 51 unselected patients, 4 had exon 1 mutations (7.8%). For the sake of comparison, if the numbers are restricted to only those patients who fit the classic or atypical RTT criteria, then the exon 1 mutation frequency is 36%. The average detection rate from the reports listed in Table 3 is 8.1% (median 5%). Taken together, these data indicate that exon 1 mutations detectable by sequencing are slightly more common than previously reported (Amir, R. E. et al., "Mutations in exon 1 of MECP2 are a rare cause of Rett syndrome," *J Med. Genet.,* 42: e15 (2005); Evans, J. C. et al., "Variation in exon 1 coding region and promoter of MECP2 in Rett syndrome and controls," *Eur J Hum Genet.,* 13: 124-126 (2005); and Quenard, A. et al., "Deleterious mutation in exon 1 of MECP2 in Rett syndrome," *Eur J Med. Genet.,* 49: 313-322 (2006)).

Although genotype-phenotype correlations are difficult to make in RTT because of differences in X-chromosome inactivation (XCI), several authors have observed that patients with exon 1 mutations result in a severe RTT phenotype (Amir, R. E. et al., "Mutations in exon 1 of MECP2 are a rare cause of Rett syndrome," *J Med. Genet.,* 42: e15 (2005); Bartholdi, D. et al., "Clinical profiles of four patients with Rett syndrome carrying a novel exon 1 mutation or genomic rearrangement in the MECP2 gene," *Clin Genet.,* 69: 319-326 (2006); and Chunshu, Y. et al., "A patient with classic Rett syndrome with a novel mutation in MECP2 exon 1," *Clin Genet.,* 70: 530-531 (2006)). This could be because exon 1 mutations cause premature truncation of the more relevant, brain-dominant isoform (Kriaucionis, S, and Bird, A., "The major form of MECP2 has a novel N-terminus generated by alternative splicing," *Nucleic Acids Res,* 32: 1818-1823 (2004) and Mnatzakanian, G. et al., "A previously unidentified MECP2 open reading frame defines a new protein isoform relevant to Rett syndrome," *Nat Genet.,* 36: 339-341 (2004)).

Out of the 14 patients harboring mutations within exon 1, all but two had classic/severe RTT. The two patients with atypically mild RTT had the same c.47__57del11nt mutation, which has also been reported in classic RTT patients (Table 2), differences for which could be attributed to skewed XCI. All four of the patients in this study had classic RTT, with one dying at an early age from pneumonia at the age of 16. Although the numbers are too small to be of any statistical significance, it is worth noting that 4 of the 14 patients listed in Table 2 died by the age of 25 (median age 17.5). RTT patients do have a decreased survival compared to the general population, but survival to 20 years was 94% in a preliminary study of patients from Texas (del Junco, D. et al., "Survival in a large cohort of US girls and women with Rett syndrome," *J Child Neurol.,* 8:101-102 (1993), Abstract.) and 85.3% in a large Australian cohort of 276 RTT patients (Laurvick, C. L. et al., "Rett syndrome in Australia: a review of the epidemiology," *J Pediatr,* 148: 347-352 (2006)).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

MECP2E1 mutations or variants identified to date.

| Nucleotide change | Position relative to NM_004992 (SEQ ID No. 1) | Amino acid change | Effect of change | Associated phenotype | Number of Patients with mutation |
|---|---|---|---|---|---|
| 11 bp deletion | Between 38 to 54 | Frameshift leads to nonsense mutation, premature truncation of protein after amino acid 36 | MECP2E1 disrupted, MECP2E2 not disrupted | Rett | 1 |
| Exon 1 deletion | 1-69 | No MECP2E1 translation | MECP2E1 and MECP2E2 disrupted | Rett | 1 |
| 1A->T | 8 | 1Met->Leu | MECP2E1 disrupted, MECP2E2 possibly diminished | Rett | 1 |
| del [TG] | 69 to 70 | Destroys exon 1/intron 1 splice site, resulting in read through and nonsense translation, with truncation after amino acid 97 | MECP2E1 disrupted, MECP2E2 probably not disrupted | Rett | 1 |
| ins [GCCGCCGCC] | Between nt 11 and 29 | ins[Ala]3 within N terminal polyalanine stretch of MECP2E1 | May affect function and or translation of MECP2E1, but not MECP2E2 | Developmental Delay | 2 |

TABLE 1-continued

| MECP2E1 mutations or variants identified to date. | | | | | |
|---|---|---|---|---|---|
| Nucleotide change | Position relative to NM_004992 (SEQ ID No. 1) | Amino acid change | Effect of change | Associated phenotype | Number of Patients with mutation |
| del [GCC] | Between nt 11 and 29 | del Ala within N terminal polyalanine stretch of MECP2E1 | May affect function and or translation of MECP2E1, but not MECP2E2 | Developmental Delay | 1 |
| ins [GGA] | Between 38 to 54 | ins Gly | May affect function and or translation of MECP2E1, but not MECP2E2 | Developmental Delay | 5 |
| −45 del [GC] | −38 to −39 relative to BX538060 | In 5'UTR, 45 nt upstream of START codon- potential SP1 transcription factor binding site | May affect transcription or translation of MECP2E1 | Developmental Delay | 1 |
| −26 del [AG] | −19 to −20 relative to BX538060 | In 5'UTR, 26 nt upstream of START codon | May affect transcription or translation of MECP2E1 | Developmental Delay | 1 |

"del" indicates a deletion; "ins" indicates an insertion

TABLE 2

| Summary of reported exon 1 sequence mutations in MECP2 to date. | | | | |
|---|---|---|---|---|
| Mutation | Patient Age | Age at Death (Cause) | XCI | RTT Phenotype |
| c.1A > T (p.Met1?) | 20 | n/a | 63:37 | classic |
| c.1A > G (p.Met1?) | 28 | n/a | 90:10 | classic |
| c.5C > T (p.A2V) | | 16 (pneumonia) | Not done | classic |
| c.23_27dup5nt (p.Ser10Argfs) | | 25 (not given) | — | classic |
| c.30delCinsGA (p.Ser10Argfs) | | 19 (pneumonia) | 70:30 | classic |
| c.47_57del11nt (p.Gly16Glufs) | 27 | n/a | — | classic |
| c.47_57del11nt (p.Gly16Glufs) | 37 | n/a | — | classic |
| c.47_57del11nt (p.Gly16Glufs) | ? | n/a | 44:56 | atypical (mild) |
| c.47_57del11nt (p.Gly16Glufs) | 13 | n/a | 73:27 | atypical (mild) |
| c.48_55dup (p.Glu19Alafs) | 5 | n/a | Random | classic |
| c.59_60delGA (p.Arg20Thrfs) | 5 | n/a | 48:52 | classic |
| c.62 + 1delGT | 8 | n/a | 68:32 | classic |
| c.62 + 1delGT | 7 | n/a | 78:22 | classic |
| c.62 + 2_62 + 3del | | 6½ (not given) | Random | atypical (severe) |

TABLE 3

| Literature reports of exon 1 mutation frequency in females with RTT and variant RTT phenotype. | | | |
|---|---|---|---|
| Frequency of Mutations in Exon 1 | Phenotype | Previously Negative for Exons 2-4 | Large Gene Rearrangements Including Exon 1 |
| 1/19; 5.2% | Typical RTT | Yes | 1 patient, exon 1 |
| 2/63; 3.2% | 38 classic RTT, 25 atypical RTT | Yes | Not tested |

TABLE 3-continued

| Literature reports of exon 1 mutation frequency in females with RTT and variant RTT phenotype. | | | |
|---|---|---|---|
| Frequency of Mutations in Exon 1 | Phenotype | Previously Negative for Exons 2-4 | Large Gene Rearrangements Including Exon 1 |
| 2/212; .9% | 211 typical RTT, 1 atypical (severe) RTT | No | 4 patients, large deletions* |
| 2/10; 20% | Typical RTT | Yes | None |
| 1/20; 5% | 12 classic RTT, 8 variant RTT, | Yes | 1 patient, exons 1-2 |
| 1/20; 5% | Classic and atypical RTT | Yes | Not tested |
| 0/97; 0% | 37 classic RTT and 60 atypical | Yes | None (Not all were tested) |
| 1/4; 25% | Classic RTT | Not specified | n/a |
| 4/51; 7.8% | 9 classical RTT, 2 variant RTT; (the rest have autism, MR, microcephaly, etc.) | 21 Patients | Not tested |
| Total: 14/496; 2.8% | | | 6 Deletions |

*One deletion including promoter and exon 1, one including exons 1-2, one including promoter and exons 1-2, and one complete gene deletion

We claim:

1. A method of detecting Rett syndrome that is associated with a point mutation in the human MECP2 gene, comprising detecting the presence or absence of a point mutation which disrupts the initiation codon in exon 1 of a nucleic acid sequence encoding the MeCP2E1 protein having the amino acid sequence of SEQ ID NO.: 4 in a sample obtained from a human by (i) amplifying the sample nucleic acid sequence with primers that amplify an adenine to guanine change at nucleotide position 8 of SEQ ID NO:1 and comparing the amplified sample nucleic acid sequence to a control nucleic acid sequence or (ii) detecting with a probe an adenine to guanine change at nucleotide position 8 of SEQ ID NO:1, wherein the presence of the mutation in the sample nucleic acid sequence indicates that the human has Rett syndrome.

2. The method according to claim 1 comprising:

a) amplifying the nucleic acid sequence in the sample with primers X1F (5'-CCATCACAGCCAATGACG-3') (SEQ ID No. 19) and X1R (5'-AGGGGGAGGGTAGAGAGGAG-3') (SEQ ID No. 20) in a polymerase chain reaction;
b) amplifying the nucleic acid sequence from the control with the same primers in step a);
c) sequencing the amplified sequences; and
d) comparing the amplified sample sequence to the amplified control sequence.

3. The method according to claim 1, wherein the MECP2 gene comprises the nucleic acid sequence of SEQ ID NO:1.

4. The method according to claim 3, wherein the presence of the mutation is in the MECP2E1 transcript of the MECP2 gene comprising SEQ ID NO.:1, wherein the MECP2E1 transcript comprises SEQ ID NO:3, and wherein the mutation is detected by performing multiplex ligation-dependent probe amplification in all four exons of the MECP2 gene sequence of SEQ ID NO.:1.

5. The method of claim 1, wherein the nucleic acid sample is extracted from a cell sample prior to analysis.

6. The method of claim 1 wherein the nucleic acids in the sample are amplified prior to analysis.

7. A method of detecting Rett Syndrome that is associated with a point mutation in the human MECP2E1 transcript of the human MECP2 gene, comprising: analyzing a nucleic acid sequence encoding a MeCP2E1 protein obtained from a human sample for the presence or absence of a point mutation in exon 1 of the MECP2E1 transcript of the MECP2 gene comprising SEQ ID NO:1 by (i) amplifying the sample nucleic acid sequence with primers that amplify an adenine to guanine change at nucleotide position 8 of SEQ ID NO:1 and comparing the amplified sample nucleic acid sequence to a control nucleic acid sequence or (ii) detecting with a probe an adenine to guanine change at nucleotide position 8 of SEQ ID NO:1, wherein the presence of the mutation in the sample nucleic acid sequence indicates that the human has Rett syndrome.

8. The method of claim 7 wherein the nucleic acid sequence is extracted from a cell sample prior to analysis.

9. The method of claim 7 wherein the nucleic acids in the samples are amplified prior to analysis.

10. The method according to claim 7 comprising:

a) amplifying the nucleic acid sequence in the sample with primers X1F (5'-CCATCACAGCCAATGACG-3') (SEQ ID No. 19) and X1R (5'-AGGGGGAGGGTAGAGAGGAG-3') (SEQ ID No. 20) in a polymerase chain reaction;
b) amplifying the nucleic acid sequence from the control with the same primers in step a);
c) sequencing the amplified sequences; and
d) comparing the amplified sample sequence to the amplified control sequence.

11. The method according to claim 1, wherein the presence of the mutation is detected by using an assay selected from the group consisting of multiplex ligation-dependent probe amplification, direct sequencing, polymerase chain reaction, reverse transcription-polymerase chain reaction, denaturing high performance liquid chromatography, electrophoretic mobility, nucleic acid hybridization, and fluorescent in situ hybridization.

12. The method according to claim 7, wherein the presence of the mutation is detected by using an assay selected from the group consisting of multiplex ligation-dependent probe amplification, direct sequencing, polymerase chain reaction, reverse transcription-polymerase chain reaction, denaturing high performance liquid chromatography, electrophoretic mobility, nucleic acid hybridization, and fluorescent in situ hybridization.

* * * * *